United States Patent
Poitout et al.

(10) Patent No.: US 7,495,110 B2
(45) Date of Patent: Feb. 24, 2009

(54) BENZIMIDAZOLE DERIVATIVES AND THEIR USE AS GNRH ANTAGONISTS

(75) Inventors: Lydie Poitout, Le Kremlin Bicetre (FR); Valérie Brault, Gif-sur-Yvette (FR); Eric Ferrandis, Saint-Remy-les-Chevreuse (FR); Christophe Thurieau, Paris (FR)

(73) Assignee: Societe de Conseils de Recherches et d'Applications Scientifiques (S.C.R.A.S.), Paris (FR)

( * ) Notice: Subject to any disclaimer, the term of this patent is extended or adjusted under 35 U.S.C. 154(b) by 215 days.

(21) Appl. No.: 10/499,384

(22) PCT Filed: Dec. 20, 2002

(86) PCT No.: PCT/FR02/04477

§ 371 (c)(1), (2), (4) Date: Jun. 16, 2004

(87) PCT Pub. No.: WO03/053939

PCT Pub. Date: Jul. 3, 2003

(65) Prior Publication Data

US 2005/0049290 A1 Mar. 3, 2005

(30) Foreign Application Priority Data

Dec. 21, 2001 (FR) .................. 01 16647

(51) Int. Cl.
- *A61K 31/4184* (2006.01)
- *C07D 235/28* (2006.01)
- *C07D 235/30* (2006.01)

(52) U.S. Cl. .................. 548/307.1; 548/307.4
(58) Field of Classification Search ............. 548/307.1, 548/307.4
See application file for complete search history.

(56) References Cited

U.S. PATENT DOCUMENTS 6,825,219 B2 * 11/2004 Cywin et al. ............... 514/338
7,132,438 B2 * 11/2006 Frenkel et al. ............. 514/388

FOREIGN PATENT DOCUMENTS

WO      WO 97/21435      6/1997

OTHER PUBLICATIONS

Golub et al., Science, vol. 286, Oct. 15, 1999, pp. 531-537.*
Database WPI, Section Ch, Week 200030, Derwent Publications Ltd., London, GB; AN 2000-342515 XP-002210484 & JP 2000 095767, (Takeda Chem Ind Ltd), Apr. 4, 2000 AB.

* cited by examiner

*Primary Examiner*—Laura L. Stockton
(74) *Attorney, Agent, or Firm*—Charles A. Muserlian

(57) ABSTRACT

A subject of the present application is new benzimidazole derivatives of formula

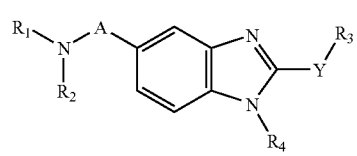

in which A, Y, $R_1$, $R_2$, $R_3$ and $R_4$ represent different variable groups. These products have an antagonist activity of GnRH (Gonadotropin-Releasing Hormone). The invention also relates to pharmaceutical compositions containing said products and their use for the preparation of a medicament.

17 Claims, No Drawings

BENZIMIDAZOLE DERIVATIVES AND THEIR USE AS GNRH ANTAGONISTS

A subject of the present application is new benzimidazole derivatives (amino- and thio-benzimidazoles. These products possess an agonist activity of GnRH (Gonadotropin-Releasing Hormone). The invention also relates to pharmaceutical compositions containing said products and their use for the preparation of a medicament.

GnRH (Gonadotropin-Releasing Hormone), also called LHRH (Luteinizing-Hormone-Releasing Hormone) is a hypothalamic decapeptide (pGlu-His-Trp-Ser-Tyr-Gly-Leu-Arg-Pro-Gly-$NH_2$) which regulates the reproduction system in vertebrates. It is released into the capillaries of the hypothalamus-hypophyseal portal system of the median eminence and of the infundibular stalk. By this network it reaches the anterior pituitary lobe and reaches, via a second capillary network, the gonadotropic target cell. GnRH acts at the level of the membrane of the target cells, via receptors with seven transmembrane segments coupled to phospholipase C via G proteins leading to an increase of intracellular calcium flux. Its action induces biosynthesis and the release of the gonadotropic hormones FSH (follicle-stimulating hormone) and LH (luteinizing hormone). GnRH agonists and antagonists have proven to be effective in women in the treatment of endometriosis, fibroma, polycystic ovary syndrome, cancer of the breast, ovary and endometrium, gonadotropic hypophyseal desensitization during medically assisted procreation protocols; in man, in the treatment of benign prostatic hyperplasia and cancer of the prostate; and in the treatment of male or female precocious puberty.

The GnRH antagonists currently used are peptide compounds which generally must be administered by intravenous or sub-cutaneous route because of their poor oral bioavailability. The non-peptide antagonists of GnRH, which present the advantage of being able to be administered by oral route, are the subject of numerous research efforts. For example, non-peptide GnRH antagonist compounds were described in *J. Med. Chem,* 41, 4190-4195 (1998) and *Bioorg. Med. Chem. Lett,* 11, 2597-2602 (2001).

The present invention relates to a new family of powerful non-peptide GnRH antagonist compounds.

A subject of the invention is therefore a compound of general formula (1)

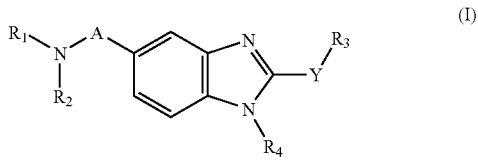

(I)

in racemic, enantiomeric form or any combination of these forms and in which:

A represents —$CH_2$— or —C(O)—;

Y represents —S— or —NH—;

$R_1$ and $R_2$ represent, independently, the hydrogen atom, a ($C_1$-$C_8$)alkyl, a ($C_5$-$C_9$)bicycloalkyl optionally substituted by one or more identical or different ($C_1$-$C_6$)alkyl radicals, or a radical of formula —$(CH_2)_n$—X in which X represents amino, ($C_1$-$C_6$)alkylamino, di(($C_1$-$C_6$)alkyl) amino, ($C_3$-$C_7$)cycloalkyl, adamantyl, heterocycloalkyl, aryl, aryl-carbonyl or heteroaryl, or a radical of formula

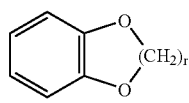

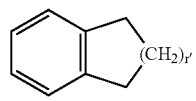

r = 1, 2 r' = 1, 2 the ($C_3$-$C_7$)cycloalkyl, heterocycloalkyl, aryl and heteroaryl radicals being optionally substituted by one or more identical or different substituents chosen from: —$(CH_2)_{n'}$—X'—Y', halo, oxo, nitro, cyano, amino, ($C_1$-$C_6$)alkylamino and di(($C_1$-$C_8$)alkyl)amino, hydroxy, $N_3$;

X' represents —O—, —S—, —C(O)—, —C(O)—O—, —NH—C(O)—, —NH—$SO_2$— or a covalent bond;

Y' represents a ($C_1$-$C_6$)alkyl radical optionally substituted by one or more identical or different halo radicals; heteroaryl or aryl or heterocycloalkyl optionally substituted by one or more identical or different substituents chosen from: ($C_1$-$C_6$)alkyl, ($C_1$-$C_6$)alkoxy, halo, nitro, cyano, amino, $CF_3$, $OCF_3$, hydroxy, $N_3$, ($C_1$-$C_6$)alkylamino and di(($C_1$-$C_8$)alkyl)amino;

n represents an integer from 0 to 6 and n' an integer from 0 to 2;

or $R_1$ and $R_2$ form together, with the nitrogen atom to which they are attached, a heterocycloalkyl, a heterobicycloalkyl or a radical of formula:

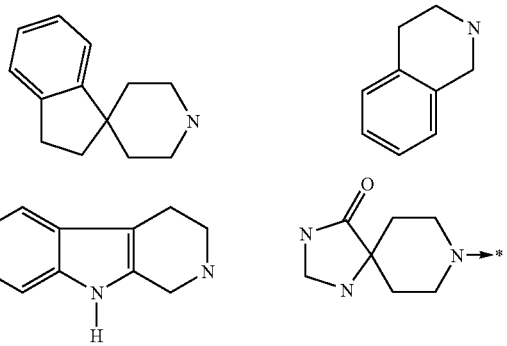

the radical formed by $R_1$ and $R_2$ together being optionally substituted by one or more identical or different substituents chosen from:

—$(CH_2)_{n''}$—X''—Y'', oxo, hydroxy, halo, nitro, cyano;

X'' represents —O—, —C(O)—, —C(O)—O— or a covalent bond;

Y'', represents a ($C_1$-$C_6$)alkyl, amino, ($C_1$-$C_6$)alkylamino, di(($C_1$-$C_6$)alkyl)amino, ($C_3$-$C_7$)cycloalkyl, heterocycloalkyl, arylalkyl radical, or aryl or heteroaryl radical optionally substituted by one or more identical or different substituents chosen from: ($C_1$-$C_6$)alkyl, ($C_1$-$C_6$)alkoxy, ($C_1$-$C_6$)alkyl-carbonyl, halo, hydroxy, nitro, cyano, $CF_3$, $OCF_3$, amino, ($C_1$-$C_6$)alkylamino and di(($C_1$-$C_6$)alkyl)amino); or a radical of formula

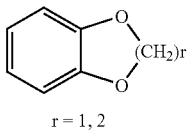

r = 1, 2

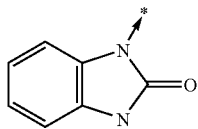

n" represents an integer from 0 to 4;
$R_3$ represents —$(CH_2)_p$—$W_3$—$(CH_2)_{p'}$-$Z_3$
$W_3$ represents a covalent bond, —CH(OH)— or —C(O)—;
$Z_3$ represents a ($C_1$-$C_6$)alkyl, adamantyl, aryl radical, a heteroaryl, or a radical of formula

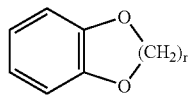

r = 1, 2

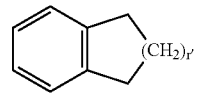

r' = 1, 2

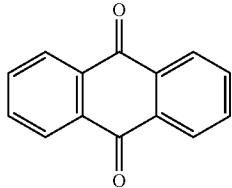

the aryl radical being optionally substituted by one or more identical or different substituents chosen from: —$(CH_2)_{p''}$—$V_3$—$Y_3$, halo, nitro, cyano, $N_3$, hydroxy;
$V_3$ represents —O—, —S—, —C(O)—, —C(O)—O—, —$SO_2$— or a covalent bond;
$Y_3$ represents a ($C_1$-$C_6$)alkyl radical optionally substituted by one or more identical or different halo radicals, amino, ($C_1$-$C_6$)alkylamino, di(($C_1$-$C_6$)alkyl)amino, phenylcarbonylmethyl, heterocycloalkyl or aryl radicals;
p, p' and p" represent, independently, an integer from 0 to 4;
$R_4$ represents a radical of formula-$(CH_2)_s$—$R''_4$
$R''_4$ represents a heterocycloalkyl containing at least one nitrogen atom and optionally substituted by ($C_1$-$C_6$) alkyl or aralkyl; a heteroaryl containing at least one nitrogen atom and optionally substituted by ($C_1$-$C_6$) alkyl; or a radical of formula —$NW_4W'_4$
$W_4$ represents the hydrogen atom, ($C_1$-$C_8$)alkyl or ($C_3$-$C_7$) cycloalkyl;
$W'_4$ represents a radical of formula —$(CH_2)_s$-$Q_4$-$Z_4$;
$Q_4$ represents a covalent bond, —$CH_2$—CH(OH)—[$CH_2$]$_t$—[O]$_{t'}$—[$CH_2$]$_{t''}$-or —C(O)—O—;
t, t' and t" represent, independently, 0 or 1;
$Z_4$ represents the hydrogen atom, ($C_1$-$C_8$)alkyl optionally substituted by one or more identical or different substituents chosen from: ($C_1$-$C_6$)alkoxy, ($C_1$-$C_6$)alkylthio, ($C_1$-$C_6$)alkyldithio and hydroxy; ($C_2$-$C_6$)alkenyl; ($C_2$-$C_6$)alkynyl; ($C_3$-$C_7$)cycloalkyl optionally substituted by one or more identical or different substituents chosen from: ($C_1$-$C_6$)alkyl, ($C_1$-$C_6$)alkoxy-carbonyl and ($C_1$-$C_6$)hydroxyalkyl; cyclohexene; adamantyl; heteroaryl; aryl optionally substituted by one or more identical or different radicals chosen from formula —$(CH_2)_{q''}$—$V_4$—$Y_4$, hydroxy, halo, nitro, cyano;

$V_4$ represents —O—, —S—, —NH—C(O)— or a covalent bond;
$Y_4$ represents a ($C_1$-$C_6$)alkyl radical optionally substituted by di(($C_1$-$C_6$)alkyl)amino or one or more identical or different halo radicals; amino; ($C_1$-$C_6$)alkylamino; di(($C_1$-$C_6$)alkyl)amino; aralkyl; heterocycloalkyl radicals;
q" represents an integer from 0 to 4;
or $Z_4$ represents a radical of formula

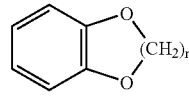

r = 1,2 s and s' represent, independently, an integer from 0 to 6;
or a pharmaceutically acceptable salt of the latter.

In the definitions indicated above, the expression halo represents the fluoro, chloro, bromo or iodo, preferably chloro, fluoro or bromo radical. The expression alkyl (unless specified otherwise), preferably represents a linear or branched alkyl radical having 1 to 6 carbon atoms, such as the methyl, ethyl, propyl, isopropyl, butyl, isobutyl, sec-butyl and tert-butyl, pentyl or amyl, isopentyl, neopentyl, 2,2-dimethyl-propyl, hexyl, isohexyl or 1,2,2,-trimethyl-propyl radicals. The term ($C_1$-$C_8$)alkyl designates a linear or branched alkyl radical having 1 to 8 carbon atoms, such as the radicals containing from 1 to 6 carbon atoms as defined above but also heptyl, octyl, 1,1,2,2-tetramethyl-propyl, 1,1,3,3-tetramethyl-butyl. The term alkyl-carbonyl preferably designates the radicals in which the alkyl radical is as defined above such as for example methylcarbonyl and ethylcarbonyl. The term hydroxyalkyl designates the radicals in which the alkyl radical is as defined above such as for example hydroxymethyl, hydroxyethyl.

By alkenyl, unless specified otherwise, is meant a linear or branched alkyl radical containing 1 to 6 carbon-atoms and having at least one unsaturation (double bond), such as for example vinyl, allyl, propenyl, butenyl or pentenyl. By alkynyl, unless specified otherwise, is meant a linear or branched alkyl radical containing 1 to 6 carbon atoms and having at least one double unsaturation (triple bond) such as for example an ethynyl, propargyl, butynyl or pentynyl radical.

The term alkoxy designates the radicals in which the alkyl radical is as defined above such as for example the methoxy, ethoxy, propyloxy or isopropyloxy radicals but also linear, secondary or tertiary butoxy, pentyloxy. The term alkoxy-carbonyl preferably designates the radicals in which the alkoxy radical is as defined above such as for example methoxycarbonyl, ethoxycarbonyl. The term alkylthio designates the radicals in which the alkyl radical is as defined above such as for example methylthio, ethylthio. The term alkyldithio preferably designates the radicals in which the alkyl radical is as defined above such as for example methyldithio ($CH_3$—S—S—), ethyldithio or propyldithio.

The term ($C_3$-$C_7$)cycloalkyl designates a saturated carbon monocyclic system comprising from 3 to 7 carbon atoms, and preferably the cyclopropyl, cyclobutyl, cyclopentyl, cyclohexyl or cycloheptyl rings. The expression heterocycloalkyl designates a condensed monocyclic or bicyclic saturated system containing from 2 to 7 carbon atoms and at least one heteroatom. This radical can contain several identical or different heteroatoms. Preferably, the heteroatoms are chosen from oxygen, sulphur or nitrogen. As an example of heterocycloalkyl, the rings containing at least one nitrogen atom such as pyrrolidine, imidazolidine, pyrrazolidine, isothiazolidine, thiazolidine, isoxazolidine, oxazolidine, piperidine, piperazine, azepane, diazepane, morpholine, decahydroisoquinoline but also the rings not containing a nitrogen atom such as tetrahydrofuran or tetrahydrothiophene can be mentioned.

The term ($C_5$-$C_9$)bicycloalkyl designates a non-condensed saturated hydrocarbon bycyclic system containing from 5 to 9 carbon atoms, such as bicyclo-heptane such as for example bicylo[2,2,1]heptane, or bicyclo-octane such as for example bicyclo[2,2,2]octane or bicyclo[3,2,1]octane. The term heterobicycloalkyl designates a non-condensed saturated hydrocarbon bycyclic system containing 5 to 8 carbon atoms and at least one heteroatom chosen from nitrogen, oxygen and sulphur. As an example of a heterobicycloalkyl, aza-bicycloheptane and aza-bicyclooctane such as 7-aza-bicyclo[2,2,1]heptane, 2-aza-bicyclo[2,2,2]octane or 6-aza-bicyclo[3,2,1]octane can be mentioned.

The expression aryl represents an aromatic radical, constituted by a condensed ring or rings, such as for example the phenyl, naphthyl or fluorenyl radical. The expression heteroaryl designates an aromatic radical, constituted by a condensed ring or rings, with at least one ring containing one or more identical or different heteroatoms chosen from sulphur, nitrogen or oxygen. As an example of a heteroaryl radical, the radicals containing at least one nitrogen atom such as pyrrolyl, imidazolyl, pyrazolyl, isothiazolyl, thiazolyl, isoxazolyl, oxazolyl, triazolyl, thiadiazolyl, pyridyl, pyrazinyl, pyrimidyl, quinolyl, isoquinolyl, quinoxalinyl, indolyl, benzoxadiazoyl, carbazolyl but also the radicals not containing a nitrogen atom such as thienyl, benzothienyl, furyl, benzofuryl or pyranyl can be mentioned.

The term aralkyl (arylalkyl) preferably designates the radicals in which the aryl and alkyl radical are as defined above; as an example of arylalkyl, benzyl, phenethyl, phenylpropyl and phenylbutyl can be mentioned. The term aryl-carbonyl preferably designates the radicals in which the aryl radical is as defined above, such as for example phenylcarbonyl.

The terms alkylamino and dialkylamino preferably designate the radicals in which the alkyl radicals are as defined above, such as for example methylamino, ethylamino, dimethylamino, diethylamino or (methyl)(ethyl)amino.

Also in the present application, the $(CH_2)_i$ radical (i an integer being able to represent n, n', n", p, p', p", s, s', s" and q"" as defined above), represents a linear or branched hydrocarbon chain, of i carbon atoms.

A subject of the invention is also a compound of general formula (I')

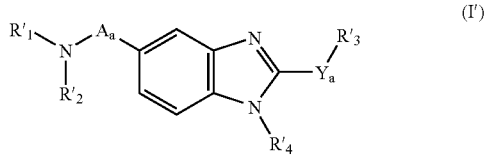

in racemic, enantiomeric form or all combinations of these forms and in which:

$A_a$ represents —$CH_2$— or —C(O)—;

$Y_a$ represents —S— or —NH—;

$R'_1$ and $R'_2$ represent, independently, the hydrogen atom, a ($C_1$-$C_8$)alkyl, a ($C_5$-$C_9$)bicycloalkyl radical optionally substituted by one or more identical or different ($C_1$-$C_6$) alkyl radicals, or a radical of formula —$(CH_2)_n$—X in which X represents, amino, ($C_1$-$C_6$)alkylamino, di(($C_1$-$C_6$)alkyl)amino, ($C_3$-$C_7$)cycloalkyl, adamantyl, heterocycloalkyl, aryl, aryl-carbonyl or heteroaryl, or a radical of formula

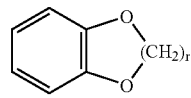 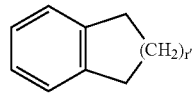

r = 1, 2                r' = 1, 2 the ($C_3$-$C_7$)cycloalkyl, heterocycloalkyl, aryl and heteroaryl radicals being optionally substituted by one or more identical or different substituents chosen from: —$(CH_2)_{n'}$—X'—Y', halo, oxo, nitro, cyano, amino, ($C_1$-$C_6$)alkylamino and di(($C_1$-$C_8$)alkyl)amino, hydroxy, $N_3$;

X' represents —O—, —S—, —C(O)—, —C(O)—O—, —NH—C(O)—, —NH—$SO_2$— or a covalent bond;

Y' represents a ($C_1$-$C_6$)alkyl radical optionally substituted by one or more identical or different halo; heteroaryl or aryl or heterocycloalkyl radicals optionally substituted by one or more identical or different substituents chosen from: ($C_1$-$C_6$)alkyl, ($C_1$-$C_6$)alkoxy, halo, nitro, cyano, amino, $CF_3$, $OCF_3$, hydroxy, $N_3$, ($C_1$-$C_6$)alkylamino and di(($C_1$-$C_8$)alkyl)amino;

n represents an integer from 0 to 6 and n' an integer from 0 to 2;

or $R'_1$ and $R'_2$ form together, with the nitrogen atom to which they are attached, a heterocycloalkyl, a heterobicycloalkyl or a radical of formula:

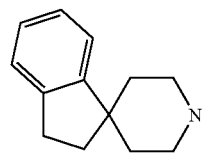 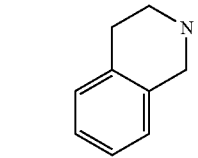

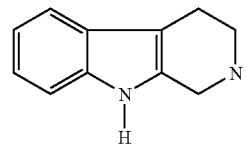 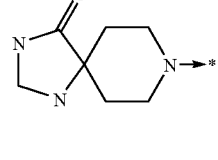

the radical which $R'_1$ and $R'_2$ form together being optionally substituted by one or more identical or different substituents chosen from:

—$(CH_2)_{n''}$—X"—Y", oxo, hydroxy, halo, nitro, cyano;

X" represents —O—, —C(O)—, —C(O)—O— or a covalent bond;

Y" represents a ($C_1$-$C_6$)alkyl, amino, ($C_1$-$C_6$)alkylamino, di(($C_1$-$C_6$)alkyl)amino, ($C_3$-$C_7$)cycloalkyl, heterocycloalkyl, arylalkyl, or aryl or heteroaryl radical optionally substituted by one or more identical or different substituents chosen from: ($C_1$-$C_6$)alkyl, ($C_1$-$C_6$)alkoxy, ($C_1$-$C_6$)alkyl-carbonyl, halo, hydroxy, nitro, cyano, $CF_3$, $OCF_3$, amino, ($C_1$-$C_6$)alkylamino and di(($C_1$-$C_6$)alkyl)amino); or a radical of formula

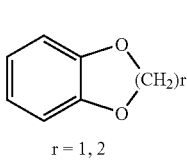 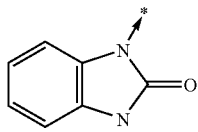

r = 1, 2 n" represents an integer from 0 to 4;
R'$_3$ represents —(CH$_2$)$_p$—W$_3$—(CH$_2$)$_{p'}$-Z$_3$
W$_3$ represents a covalent bond, —CH(OH)— or —C(O)—;
Z$_3$ represents a (C$_1$-C$_6$)alkyl, adamantyl, aryl, a heteroaryl radical, or a radical of formula

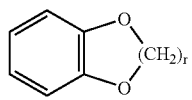 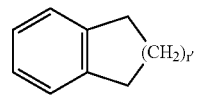

r = 1, 2    r' = 1, 2 the aryl radical being optionally substituted by one or more identical or different substituents chosen from: —(CH$_2$)$_{p''}$—V$_3$—Y$_3$, halo, nitro, cyano, N$_3$, hydroxy;
V$_3$ represents —O—, —S—, —C(O)—, —C(O)—O—, —SO$_2$— or a covalent bond;
Y$_3$ represents a (C$_1$-C$_6$)alkyl radical optionally substituted by one or more identical or different halo, amino, (C$_1$-C$_6$)alkylamino, di((C$_1$-C$_6$)alkyl)amino, phenylcarbonylmethyl, heterocycloalkyl or aryl radicals;
p, p' and p" represent, independently, an integer from 0 to 4;
R'$_4$ represents a radical of formula —(CH$_2$)$_s$—R"$_4$
R"$_4$ represents a heterocycloalkyl containing at least one nitrogen atom and optionally substituted by (C$_1$-C$_6$) alkyl or aralkyl; a heteroaryl containing at least one nitrogen atom and optionally substituted by (C$_1$-C$_6$) alkyl; or a radical of formula —NW$_4$W'$_4$
W$_4$ represents the hydrogen atom, (C$_1$-C$_8$)alkyl or (C$_3$-C$_7$) cycloalkyl;
W'$_4$ represents a radical of formula —(CH$_2$)$_{s'}$-Q$_4$-Z$_4$;
Q$_4$ represents a covalent bond, —CH$_2$—CH(OH)—[CH$_2$]$_t$-[O]$_{t'}$-[CH$_2$]$_{t''}$-or —C(O)—O—;
t, t' and t" represent, independently, 0 or 1;
Z$_4$ represents the hydrogen atom, (C$_1$-C$_8$)alkyl, (C$_3$-C$_7$) cycloalkyl; heteroaryl; aryl optionally substituted by one or more identical or different radicals chosen from formula —(CH$_2$)$_{q''}$—V$_4$—Y$_4$, hydroxy, halo, nitro, cyano;
V$_4$ represents —O—, —S—, —NH—C(O)— or a covalent bond;
Y$_4$ represents a (C$_1$-C$_6$)alkyl radical optionally substituted by di((C$_1$-C$_6$)alkyl)amino or one or more identical or different halo; amino; (C$_1$-C$_6$)alkylamino; di((C$_1$-C$_6$)alkyl)amino; aralkyl; heterocycloalkyl radicals;

q" represents an integer from 0 to 4;
or Z$_4$ represents a radical of formula

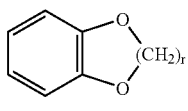

r = 1,2 s and s' represent, independently, an integer from 0 to 6;
or a pharmaceutically acceptable salt of the latter.

A more particular subject of the present invention is a compound of formula I or I' as defined above or a pharmaceutically acceptable salt of the latter, and in which A represents —C(O)—.

A more particular subject of the present invention is a compound of formula I as defined above or a pharmaceutically acceptable salt of the latter, and in which
the cycloalkyl that represents X is cyclohexyl or cycloheptyl,
the heterocycloalkyl that represents X is chosen from: piperidine, pyrrolidine, thiazolidine, morpholine and tetrahydrothiophene;
the aryl that represents X is the phenyl, naphthyl or fluorenyl radical;
the aryl of the aryl-carbonyl radical that represents X, is the phenyl radical;
the heteroaryl that represents X is chosen from: pyridine, imidazole, thiophene, indole, carbazole and isoquinoline;
the heteroaryl that represents Y' is chosen from oxazole and imidazole;
the aryl that represents Y' is the phenyl radical;
the heterocycloalkyl that represents Y' is piperazine;
the heterocycloalkyl that R$_1$ and R$_2$ form together with the nitrogen atom to which they are attached, is chosen from: piperidine, piperazine, diazepane, thiazolidine and morpholine;
the cycloalkyl that represents Y" is cyclopentyl or cyclohexyl;
the heterocycloalkyl that represents Y" is chosen from: piperidine, pyrrolidine and morpholine;
the arylalkyl and the aryl that represents Y" are respectively the benzyl radical and the phenyl radical;
the heteroaryl that represents Y" is chosen from: pyridine, pyrazine, furane and thiophene.

A more particular subject of the present invention is also a compound of formula I as defined above or a pharmaceutically acceptable salt of the latter, and in which
the aryl that represents Z$_3$ is the phenyl or naphthyl radical;
the heteroaryl that represents Z$_3$ is chosen from benzo[b]thiophene and benzo[b]furanne;
the heterocycloalkyl and the aryl that represents Y$_3$ are respectively the pyrrolidine and p henyl radicals.

A more particular subject of the present invention is also a compound of formula I as defined above or a pharmaceutically acceptable salt of the latter, and in which
the heterocycloalkyl that represents R"$_4$ is chosen from: piperazine, piperidine, morpholine and pyrrolidine;
the aralkyl which optionally substitutes the heterocycloalkyl that represents R"$_4$ is the benzyl radical;
the heteroaryl that represents R"$_4$ is imidazole;
the (C$_3$-C$_7$)cycloalkyl that represents Z$_4$ is cyclopropyl, cyclobutyl, cyclopentyl, cyclohexyl or cycloheptyl;

the heteroaryl that represents $Z_4$ is chosen from: pyridine, thiophene, indole and furane;
the aryl that represents $Z_4$ and is phenyl or naphthyl;
the aralkyl that represents $Y_4$ is benzyl;
the heterocycloalkyl that represents $Y_4$ is pyrrolidine;
the aralkyl which is substituted on the heterocycloalkyl that form together $W_4$ and $W'_4$ is the benzyl radical.

Preferentially, a subject of the invention is a compound of formula I as defined above or a pharmaceutically acceptable salt of the latter and in which A represents —C(O)— and $R_1$ and $R_2$ represent, independently, the hydrogen atom, a $((C_1-C_8)$alkyl radical or a radical of formula —$(CH_2)_n$—X in which X represents, amino, di(alkyl)amino, adamentyl, cyclohexyl, cycloheptyl, piperidine, morpholine, pyrrolidine, phenyl, pyridine, imidazole, thiophene, indole, carbazole being optionally substituted $(C_1-C_6)$alkyl, or a radical of formula

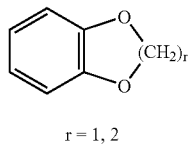 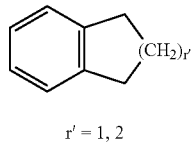

r = 1, 2                r' = 1, 2 the piperidine, pyrrolidine and phenyl radicals being optionally substituted by one or more identical or different substituents chosen from: —$(CH_2)_{n'}$—X'—Y', halo, oxo, amino and di($(C_1-C_8)$alkyl)amino;

X' represents —O—, —S—, —C(O)—O—, —NH—C(O)—, —NH—SO$_2$— or a covalent bond;

Y' represents a $(C_1-C_6)$alkyl, oxazole, phenyl radical optionally substituted by $(C_1-C_4)$alkyl or piperazine optionally substituted by $(C_1-C_4)$alkyl;

or $R_1$ and $R_2$ form together, with the nitrogen atom to which they are attached, piperidine, piperazine and diazepane, thiazolidine, morpholine, or a cyclic radical of formula:

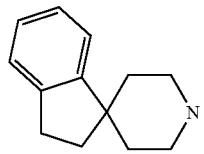 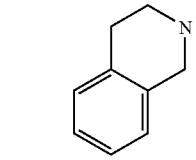

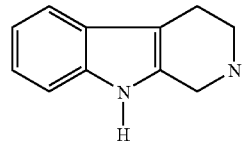 

the radical that $R_1$ and $R_2$ form together being optionally substituted by one or more identical or different substituents chosen from:
—$(CH_2)_{n''}$—X"—Y";
X" represents —C(O)—, —C(O)—O— or a covalent bond;
Y" represents a $(C_1-C_6)$alkyl; di(alkyl)amino, cyclopentyl, cyclohexyl, piperidine, pyrrolidine, morpholine, benzyl, pyridine, pyrazine, furane, thiophene, or phenyl radical optionally substituted by one or more identical or different substituents chosen from $(C_1-C_6)$ alkyl, $(C_1-C_6)$alkoxy, $(C_1-C_6)$alkyl-carbonyl and halo; or Y" represents a radical of formula

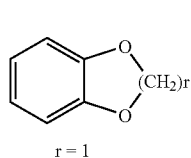 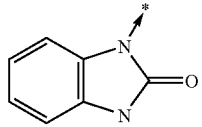

r = 1

Preferentially a subject of the invention is a compound of formula I as defined above or a pharmaceutically acceptable salt of the latter and in which A represents —C(O)— and $R_3$ represents —$(CH_2)_p$—$W_3$—$(CH_2)_{p'}$-$Z_3$ $W_3$ represents a covalent bond, —CH(OH)— or —C(O)—;

$Z_3$ represents a $(C_1-C_6)$alkyl, phenyl, naphthyl, benzo[b]thiophene, benzo[b]furannyl radical, or a radical of formula

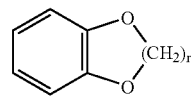 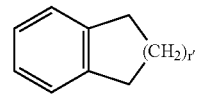

r = 1, 2                r' = 1

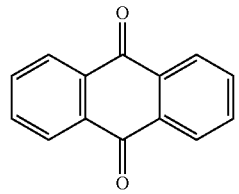

the radical phenyl being optionally substituted by one or more identical or different substituents chosen from: —$(CH_2)_{p''}$—$V_3$—$Y_3$, halo, nitro, cyano;

$V_3$ represents —O—, —S—, —C(O)—, —C(O)—O—, —SO$_2$— or a covalent bond;

$Y_3$ represents a $(C_1-C_6)$alkyl radical optionally substituted by one or more identical or different halo; amino; di($(C_1-C_6)$alkyl)amino; phenylcarbonylmethyl; pyrrolidine or phenyl radicals;

p, p' and p" represent, independently, an integer from 0 to 2.

Preferentially a subject of the invention is a compound of formula I' as defined above or a pharmaceutically acceptable salt of the latter and in which $A_a$ represents —C(O)— and the radicals $R'_1$, $R'_2$, $R'_3$ and $R'_4$ have respectively the definitions of the $R_1$, $R_2$, $R_3$ and $R_4$ radicals as defined above.

Preferentially a subject of the invention is a compound of formula I as defined above or a pharmaceutically acceptable salt of the latter and in which A represents —C(O)— and $R_4$ represents a radical of formula —$(CH_2)_s$—$R''_4$ $R''_4$ represents the piperidine ring optionally substituted by benzyl, piperazine optionally substituted by benzyl, or a radical of formula —$NW_4W'_4$ $W_4$ represents the hydrogen atom or $(C_1-C_8)$alkyl;

$W'_4$ represents a radical of formula —$(CH_2)_s$-$Q_4$-$Z_4$;

$Q_4$ represents a covalent bond, —$CH_2$—CH(OH)—, —$CH_2$—CH(OH)—$CH_2$—O—, —$CH_2$—CH(OH)—$CH_2$—, —$CH_2$—CH(OH)—$CH_2$—O—$CH_2$— or —C(O)—O—;

$Z_4$ represents the hydrogen atom, $(C_1-C_8)$alkyl optionally substituted by $(C_1-C_6)$alkoxy, $(C_1-C_6)$alkylthio, $(C_1-C_6)$ alkyldithio or one or two hydroxy; $(C_2-C_6)$alkenyl; $(C_2-C_6)$alkynyl; cyclopropyl radicals optionally substituted by alkoxycarbonyl; cyclobutyl, cyclopentyl optionally substituted by hydroxyalkyl; cyclohexyl optionally substituted by one or more alkyl; cycloheptyl, cyclohexene, adamantyl, pyridine, thiophene, indole, furane, naphthyl; phenyl radicals optionally substituted by one or more identical or different radicals chosen from: —$(CH_2)_{q''}$—$X_4$—$Y_4$, hydroxy, halo and cyano;

$X_4$ represents —O— or a covalent bond;

$Y_4$ represents a $(C_1-C_6)$alkyl, di$((C_1-C_6)$alkyl)amino or pyrrolidine radical.

Very preferentially a subject of the invention is also a compound of formula I as defined above in which A represents —C(O)—, Y represents —NH— and $R_1$ and $R_2$ represent, independently, a $(C_1-C_8)$alkyl radical;

$R_3$ represents —$(CH_2)_p$—$W_3$—$(CH_2)_{p'}$-$Z_3$ $W_3$ represents a covalent bond; $Z_3$ represents the phenyl radical substituted by one or more identical or different substituents chosen from: —$(CH_2)_{p''}$—$V_3$—$Y_3$ and halo; $V_3$ represents —O— or —S—; and $Y_3$ represents a $(C_1-C_6)$alkyl radical; p, p' and p'' represent 0;

$R_4$ represents a radical of formula —$(CH_2)_s$—$R''_4$ $R''_4$ represents a radical of formula —$NW_4W'_4$ $W_4$ represents the hydrogen atom or $(C_1-C_8)$alkyl;

$W'_4$ represents a radical of formula —$(CH_2)_{s'}$-$Q_4$-$Z_4$;

$Q_4$ represents a covalent bond;

$Z_4$ represents the hydrogen atom, $(C_1-C_8)$alkyl optionally substituted by hydroxy, $(C_3-C_7)$cycloalkyl, heteroaryl, aryl optionally substituted by one or more identical or different radicals chosen from formula —$(CH_2)_{q''}$—$V_4$—$Y_4$;

$V_4$ represents —O— or a covalent bond;

$Y_4$ represents a $(C_1-C_6)$alkyl or di$((C_1-C_6)$alkyl)amino radical;

q" represents 0; s represents an integer from 2 to 4, and s' an integer from 1 to 2.

and very preferentially $(C_3-C_7)$cycloalkyl is chosen from cyclopentyl and cyclohexyl, the heteroaryl represents pyridine and the aryl represents phenyl; or a pharmaceutically acceptable salt of the latter.

Preferentially, a subject of the invention is the invention is a compound of formula I' as defined above or a pharmaceutically acceptable salt of the latter and in which $A_a$ represents —C(O)—, $Y_a$—NH—, the $R'_1$, $R'_2$ and $R'_3$ radicals have respectively the definitions of the $R_1$, $R_2$ and $R_3$ radicals as defined above, and $R'_4$ represents a radical of formula —$(CH_2)_s$—$R''_4$ $R''_4$ represents a radical of formula —$NW_4W'_4$ $W_4$ represents the hydrogen atom or $(C_1-C_8)$alkyl;

$W'_4$ represents a radical of formula —$(CH_2)_{s'}$-$Q_4$-$Z_4$;

$Q_4$ represents a covalent bond;

$Z_4$ represents the hydrogen atom, $(C_1-C_8)$alkyl, $(C_3-C_7)$cycloalkyl, heteroaryl, aryl optionally substituted by one or more identical or different radicals chosen from formula —$(CH_2)_{q''}$—$V_4$—$Y_4$;

$V_4$ represents —O— or a covalent bond;

$Y_4$ represents a $(C_1-C_6)$alkyl or di$((C_1-C_6)$alkyl)amino radical;

q" represents 0; s represents an integer from 2 to 4, and s' an integer from 1 to 2.

and very preferentially the $(C_3-C_7)$cycloalkyl is chosen from cyclopentyl and cyclohexyl, the heteroaryl represents pyridine and the aryl phenyl; or a pharmaceutically acceptable salt of the latter.

Very preferentially, a subject of the invention is also a compound of formula I as defined above in which A represents —C(O)—, Y represents the sulphur atom and $R_1$ and $R_2$ represent, independently, a $(C_1-C_8)$alkyl radical;

$R_3$ represents —$(CH_2)_p$—$W_3$—$(CH_2)_{p'}$-$Z_3$ $W_3$ represents a covalent bond or —C(O)—; $Z_3$ represents the phenyl radical substituted by one or more identical or different substituents chosen from: —$(CH_2)_{p''}$—$V_3$—$Y_3$ and halo; $V_3$ represents —O— or a covalent bond; and $Y_3$ represents a $(C_1-C_6)$alkyl or di$((C_1-C_6)$alkyl)amino radical; p represents 1, and p' and p'' represent 0;

$R_4$ represents a radical of formula —$(CH_2)_s$—$R''_4$ $R''_4$ represents a radical of formula —$NW_4W'_4$ $W_4$ represents the hydrogen atom or $(C_1-C_8)$alkyl;

$W'_4$ represents a radical of formula —$(CH_2)_{s'}$-$Q_4$-$Z_4$;

$Q_4$ represents a covalent bond;

$Z_4$ represents the hydrogen atom, $(C_1-C_8)$alkyl, heteroaryl, aryl s represents an integer from 2 to 4, and s' an integer from 1 to 2, and very preferentially the heteroaryl represents pyridine and the aryl phenyl; or a pharmaceutically acceptable salt of the latter.

Preferentially, a subject of the invention is a compound of formula I' as defined above or a pharmaceutically acceptable salt of the latter and in which $A_a$ represents —C(O)—, $Y_a$ a sulphur atom and the $R'_1$, $R'_2$, $R'_3$ and $R'_4$ radicals have respectively the definitions of the $R_1$, $R_2$, $R_3$ and $R_4$ radicals as defined above when A represents —C(O)— and Y a sulphur atom.

Preferentially, a subject of the invention is also a compound of formula I as defined above in which A represents —$CH_2$—, Y—NH— and $R_1$ and $R_2$ represent, independently, a $((C_1-C_6)$alkyl radical; $R_3$ represents a phenyl substituted by one or more identical or different $(C_1-C_6)$alkoxy substituents; $R_4$ represents a radical of formula —$(CH_2)$, —$R''_4$; $R''_4$ represents a radical of formula —$NW_4W'_4$; $W_4$ represents $(C_1-C_8)$ alkyl; $W'_4$ represents a radical of formula —$(CH_2)_{s'}$-$Q_4$-$Z_4$; $Q_4$ represents a covalent bond and $Z_4$ represents pyridine; or a pharmaceutically acceptable salt of the latter.

Preferentially, a subject of the invention is a compound of formula I' as defined above or a pharmaceutically acceptable salt of the latter and in which $A_a$ represents —$CH_2$—, $Y_a$—NH— and the $R'_1$, $R'_2$, $R'_3$ and $R'_4$ radicals have respectively the definitions of the $R_1$, $R_2$ $R_3$ and $R_4$ radicals as defined above when A represents —$CH_2$— and Y—NH—.

In the present application, the symbol ->* corresponds to the point of attachment of the radical. When the attachment site is not specified on the radical, this means that the attachment is carried out on one of the available sites for such attachment of this radical.

According to the definitions of the variable groups A, Y, $R_1$, $R_2$, $R_3$ and $R_4$, the compounds according to the invention can be prepared in liquid phase according to the different procedures A to H described below.

A. Preparation According to Reaction Diagram A:

The compounds of formula I according to the invention in which Y represents —NH— and A represents —C(O)—, can be prepared according to the following Diagram A:

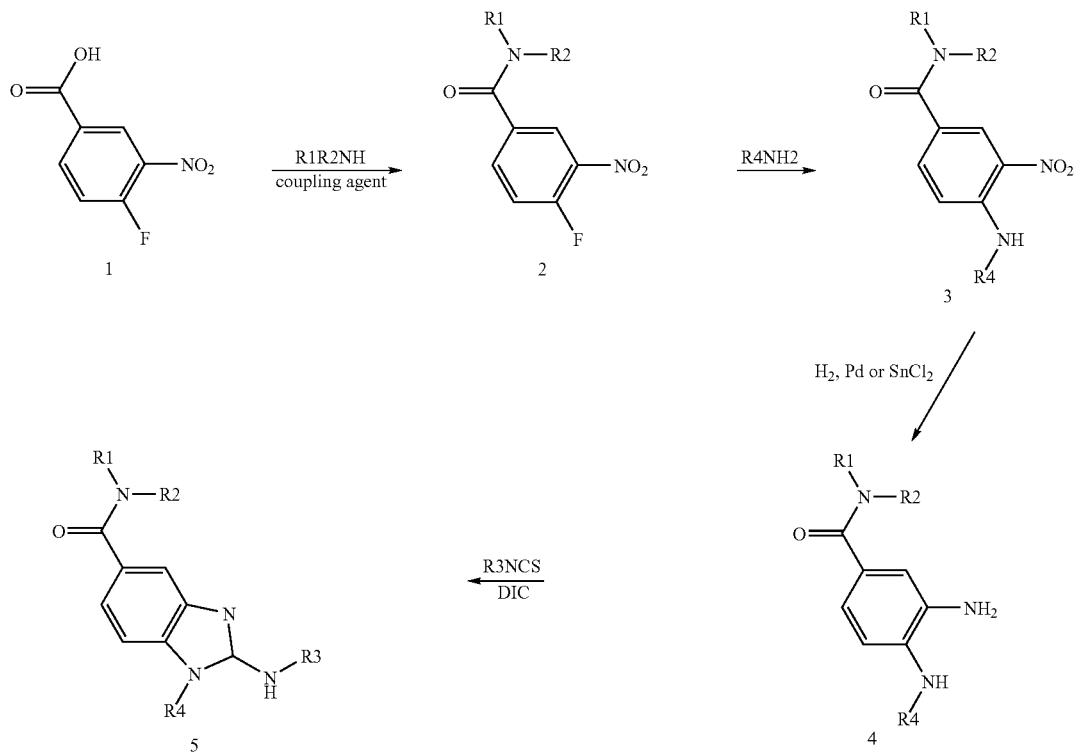

As described in Diagram A, 4-fluoro-3-nitrobenzoic acid (1) can be coupled with a primary or secondary amine in the presence of a coupling agent such as diisopropylcarbodiimide, dicyclohexylcarbodiimide, with or without 1-hydroxybenzotriazole (HOBt), in an inert organic solvent such as methylene chloride, tetrahydrofuran or dimethylformamide at ambient temperature for 3 to 24 hours in order to produce the corresponding amide (2). Treatment of the fluorinated derivative (2) with a primary amine in the presence of an inorganic base such as cesium or potassium carbonate in an inert organic solvent such as dimethylformamide or acetonitrile at a temperature of 20-70° C. for 2 to 16 hours leads to derivative (3). The nitro function of the compound (3) is reduced by treatment with tin chloride dihydrate in an inert solvent such as ethyl acetate or dimethylformamide at a temperature of 60-80° C. for 3 to 15 hours, or by catalytic hydrogenation in the presence of 10% palladium on carbon in an inert solvent such as methanol, ethanol, ethyl acetate or a mixture of these solvents, at a temperature of 18-25° C., for 2 to 8 hours in order to produce dianiline (4). Derivative (4) is then treated with an isothiocyanate in the presence of a resin-supported or non resin-supported coupling agent such as diisopropylcarbodiimide or dicyclohexylcarbodiimide or N-methylcyclohexylcarbodiimide N-methyl polystyrene resin in an inert solvent such as tetrahydrofuran, methylene chloride, or chloroform at a temperature of 20-70° C. for 2 to 72 hours in order to produce derivative (5). Alternatively, derivative (4) can be treated with an isothiocyanate in an inert solvent such as tetrahydrofuran, methylene chloride or chloroform then the resulting thiourea can be treated with methyl iodide in a polar solvent such as ethanol for 3 to 24 hours at a temperature of 20-70° C. in order to produce (5).

EXAMPLE A1

N,N-diisobutyl-1-{3-[methyl(2-pyridin-2-ylethyl)amino]propyl}-2-[(3,4,5-trimethoxyphenyl)amino]-1H-benzimidazole-5-carboxamide hydrochloride

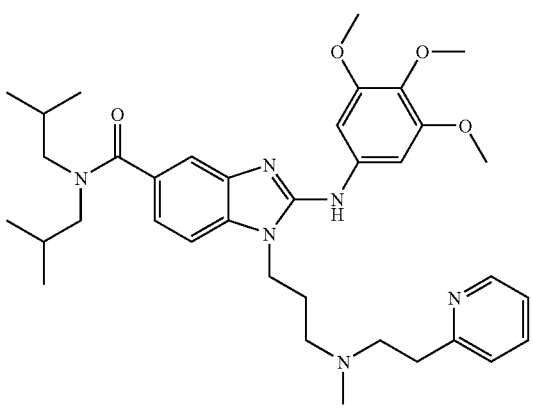

Stage 1: 4-fluoro-N,N-diisobutyl-3-nitrobenzamide

Diisopropylcarbodiimide (13.8 ml, 1.2 eq) is added to 4-fluoro-3-nitrobenzoic acid (15 g, 1 eq) in solution in THF (150 ml). The mixture is stirred for 3 hours at a temperature of approximately 20° C. then diisobutylamine (12.9 ml, 1 eq) is added. After stirring for 15 hours at approximately 20° C., the reaction mixture is evaporated under reduced pressure at 40° C. The residue is taken up in dichloromethane (200 ml) and water (70 ml). After decantation and extraction, the combined organic phases are washed with salt water, followed by drying over Na$_2$SO$_4$ then evaporating under reduced pressure at 40° C. Purification of the compound by flash chromatography on silica gel (eluent: heptane/ethyl acetate 8:2) produces the expected compound in the form of a yellow solid (13.8 g; 63% yield).

MS/LC: MW calculated=296.3; m/z=297.2 (MH+)–Melting point=47° C.

Stage 2: N,N-diisobutyl-4-({3-[methyl(2-pyridin-2-ylethyl) amino]propyl}amino)-3-nitrobenzamide A mixture of 4-fluoro-N,N-diisobutyl-3-nitrobenzamide (2.07 g, 1 eq), N-(2-pyridin-2-ylethyl)propane-1,3-diamine (1.6 g, 1.2 eq) and cesium carbonate (4.5 g, 2 eq) in acetonitrile (70 ml) is heated under reflux for 3 hours then concentrated under reduced pressure at 40° C. The residue is taken up in dichloromethane (100 ml) and water (40 ml). After decantation and extraction, the combined organic phases are washed with salt water, dried over Na$_2$SO$_4$ then evaporated under reduced pressure at 40° C. Purification of the residue by flash chromatography on silica gel (eluent: dichloromethane 100 to dichloromethane/methanol 8:2) produces the expected compound in the form of a yellow oil (3.1 g; 92% yield).

MS/LC: MW calculated=469.6; m/z=470.3 (MH+)

NMR ($^1$H, 400 MHz, DMSO-d$_6$): δ0.79 (m, 12H), 1.75 (m, 2H), 1.90 (m, 2H), 2.23 (s, 3H), 2.48 (t, 3H, $^3$J=6 Hz), 2.71 (t, 2H, $^3$J=7 Hz), 2.87 (t, 2H, $^3$J=7 Hz), 3.19 (d,4H, $^3$J=7 Hz), 3.33 (m, 2H), 7.01 (d, 1H), 7.10 (m, 1H), 7.23 (d, 1H), 7.50 (m, 1H), 7.60 (m, 1H), 7.99 (s, 1H), 8.41 (m, 1H), 8.59 (t, 1H, $^3$J=5 Hz).

Stage 3: 3-amino-N,N-diisobutyl-4-({3-[methyl(2-pyridin-2-ylethyl)amino]propyl}amino)benzamide N,N-diisobutyl-4-({3-[methyl(2-pyridin-2-ylethyl) amino]propyl}amino)-3-nitrobenzamide (2.9 g) in solution in an ethyl acetate/ethanol mixture (100 ml), and 10% palladium on carbon (290 mg) are added together in an autoclave. After stirring for 7 hours under a hydrogen atmosphere (3 bars), the catalyst is eliminated by filtration on Celite and the filtrate is concentrated under reduced pressure at 40° C. in order to produce the expected compound in the form of an oil (2.5 g, 92% yield).

MS/LC: MW calculated=439.6; m/z=440.3 (MH+)

NMR ($^1$H, 400 MHz, DMSO-d$_6$): δ 0.77 (m, 12H), 1.71 (m, 2H), 1.90 (m, 2H), 2.22 (s, 3H), 2.47 (m, 3H), 2.70 (t, 2H, $^3$J=7 Hz), 2.87 (t, 2H, $^3$J=7 Hz), 3.0 (m, 2H), 3.17 (d, 4H, $^3$J=7.5 Hz), 4.62 (s, 2H), 4.71 (s, 1H), 6.33 (d, 1H), 6.50 (d, 1H), 6.57 (s, 1H), 7.15 (m, 1H), 7.25 (d, 1H), 7.63 (m, 1H), 8.45 (m, 1H).

Stage 4: N,N-diisobutyl-1-{3-[methyl(2-pyridin-2-ylethyl) amino]propyl}-2-[(3,4,5-trimethoxyphenyl)amino]-1H-benzimidazole-5-carboxamide hydrochloride 3,4,5 trimethoxyphenylisothiocyanate (27 mg, 1.2 eq) and N-methylcyclohexylcarbodiimide-N-methyl-polystyrene resin (acquired from Novabiochem; load 1.69 mmol/g, 236 mg, 4 eq) are added successively to a solution of 3-amino-N, N-diisobutyl-4-({3-[methyl(2-pyridin-2-ylethyl)amino] propyl}amino)benzamide (48 mg, 1 eq) in tetrahydrofuran (2 ml). The mixture is heated under reflux for 18 hours then cooled down to ambient temperature and aminomethyl polystyrene resin (acquired from Novabiochem, 2 eq) is added. After stirring for 4 hours at ambient temperature, the mixture is filtered on frit and the filtrate is concentrated under reduced pressure at 40° C. The residue obtained is dissolved in ethyl ether and a solution of 1N HCl in ethyl ether is added dropwise in order to produce the expected compound in the form of the hydrochloride salt (80 mg, 89% yield).

MS/LC: MW calculated=630.8; m/z=631.4 (MH+)

NMR ($^1$H, 400 MHz, DMSO-d$_6$): δ0.66 (m, 6H), 0.91 (m, 6H), 1.71-2.03 (m, 2H), 2.49 (m, 2H), 2.86 (s, 3H), 3.01-3.72 (m, 10H), 3.81 (s, 3H), 3.88 (s, 6H), 4.58 (t, 2H, $^3$J=7 Hz), 6.93 (s, 2H), 7.30 (m, 2H), 7.60 (m, 1H), 7.70 (m, 1H), 7.82 (d, 1H), 8.12 (m, 1H), 8.67 (d, 1H), 11.2 (s, 1H), 11.7 (s, 1H), 13.0 (s, 1H).

EXAMPLE A2

1-{3-[benzyl(methyl)amino]propyl}-2-[(3,5-dimethoxyphenyl)amino]-N,N-diisobutyl-1H-benzimidazole-5-carboxamide hydrochloride

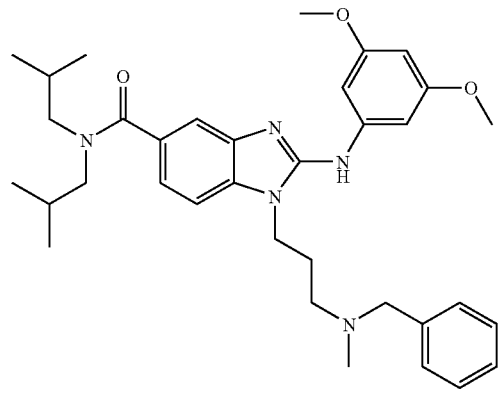

Stage 1: 3-amino-4-({3-[benzyl(methyl)amino] propyl}amino)-N,N-diisobutyl benzamide Tin chloride dihydrate (3.58 g, 5eq) is added to a solution of 4-({3-[benzyl(methyl)amino]propyl}amino)-N,N-diisobutyl-3-nitrobenzamide (1.44 g, prepared according to the procedure described for Example A1), in ethyl acetate (40 ml). The mixture is heated under reflux for 7 hours then cooled down to a temperature of approximately 20° C. and poured into a saturated solution of NaHCO$_3$. After decanting and extracting with ethyl acetate, the organic phases are combined, washed with salt water, dried over sodium sulphate and concentrated under reduced pressure at 40° C. Purification by flash chromatography on silica gel (eluent dichloromethane/ methanol 95:5) produces the compound in the form of a foam (1.06 g, 78% yield).

MS/LC: MW calculated=424.3; m/z=425.3 (MH+)

NMR ($^1$H, 400 MHz, DMSO-d$_6$): δ 0.77 (m, 12H), 1.78 (m, 2H), 1.90 (m, 2H), 2.12 (s, 3H), 2.49 (m, 3H), 3.06 (t, 2H, $^3$J=7 Hz), 3.17 (d, 4H, $^3$J=7.5 Hz), 3.48 (s, 2H), 4.61 (s, 2H), 4.72 (s, 1H), 6.38 (d, 1H), 6.51 (m, 1H), 6.59 (s, 1H), 7.19-7.30 (m, 5H).

Stage 2: 1-{3-[benzyl(methyl)amino]propyl}-2-[(3,5-dimethoxy phenyl)amino]-N,N-diisobutyl-1H-benzimidazole-5-carboxamide hydrochloride 3,4 dimethoxyphenylisothiocyanate (35 mg, 1.2 eq) and N-methylcyclohexylcarbodiimide-N-methyl-polystyrene resin (acquired from Novabiochem; charge 1.69 mmol/g, 355 mg, 4 eq) are added successively to a solution of 3-amino-4-({3-[benzyl(methyl)amino]propyl}amino)-N,N-diisobutyl-benzamide (65 mg, 1 eq) in tetrahydrofuran (2 ml). The mixture is heated under reflux for 18 hours then cooled down to ambient temperature and aminomethyl polystyrene resin (acquired from Novabiochem, 2 eq) is added. After stirring for 4 hours at ambient temperature, the mixture is filtered on frit and the filtrate is concentrated under reduced pressure at 40° C. The residue obtained is dissolved in ethyl ether and a 1N solution of HCl in ethyl ether is added dropwise in order to produce the expected compound in the form of the hydrochloride salt (81 mg, 92% yield).

MS/LC: MW calculated=585.3; m/z=586.5 (MH+)

NMR ($^1$H, 400 MHz, DMSO-$d_6$): δ 0.85 (m, 6H), 0.92 (m, 6H), 1.85 (m, 1H), 2.05 (m, 1H), 2.28 (m, 2H), 2.86 (s, 3H), 3.08-3.3 (m, 6H), 3.78 (s, 6H), 4.20-4.40 (m, 2H), 4.50 (m, 2H), 6.42 (s, 1H), 6.90 (m, 2H), 7.22 (m, 1H), 7.22-7.64 (m, 8H), 10.98 (m, 1H).

The following compounds were prepared according to reaction diagram A and in a similar manner to the procedure described for the synthesis of N,N-diisobutyl-1-{3-[methyl (2-pyridin-2-ylethyl)amino]propyl}-2-[(3,4,5-trimethoxyphenyl)amino]-1H-benzimidazole-5-carboxamide or 1-{3-[benzyl(methyl)amino]propyl}-2-[(3,5-dimethoxyphenyl) amino]-N,N-diisobutyl-1H-benzimidazole-5-carboxamide:

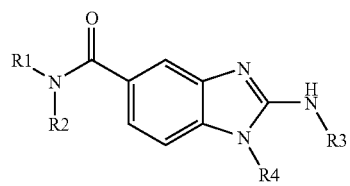

In the above formula, $R_1R_2N$ represents one of the radicals below:

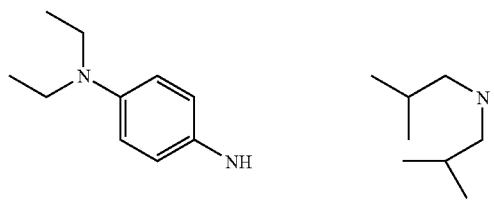

$R_3$ represents one of the radicals below

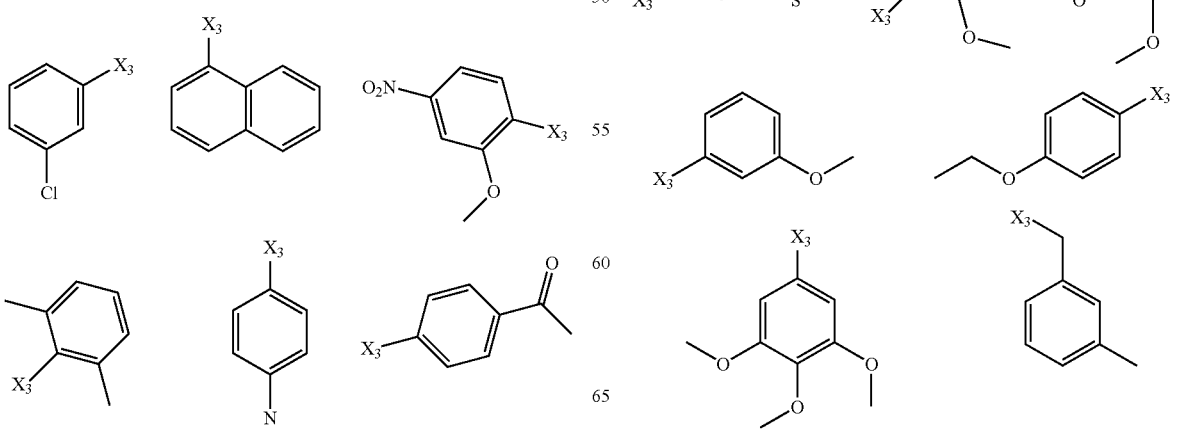

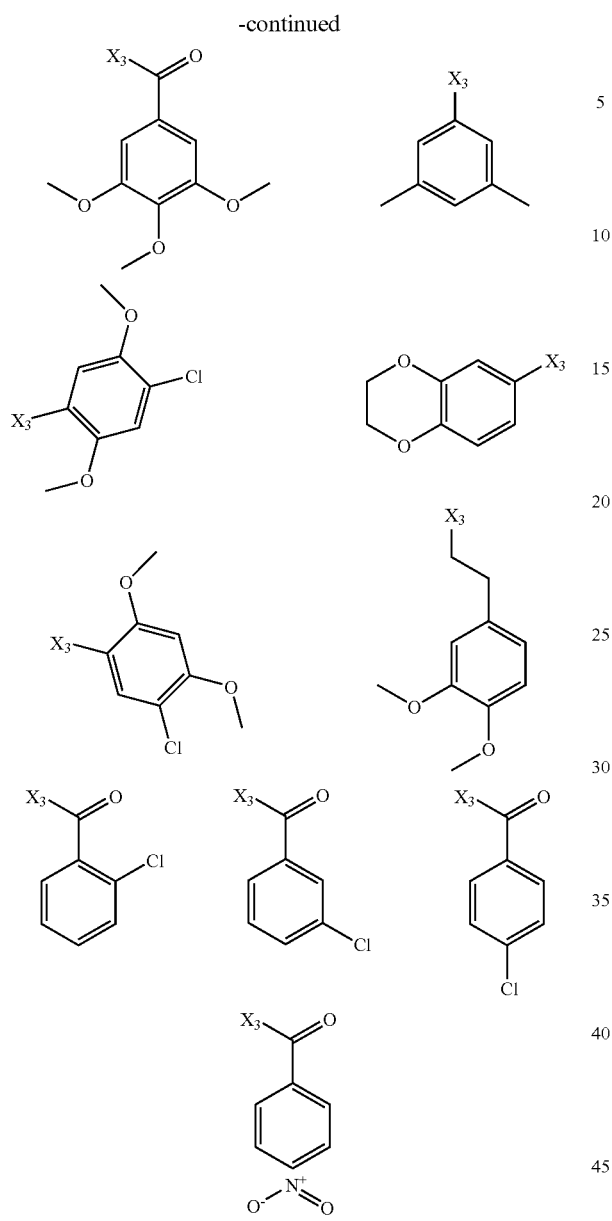
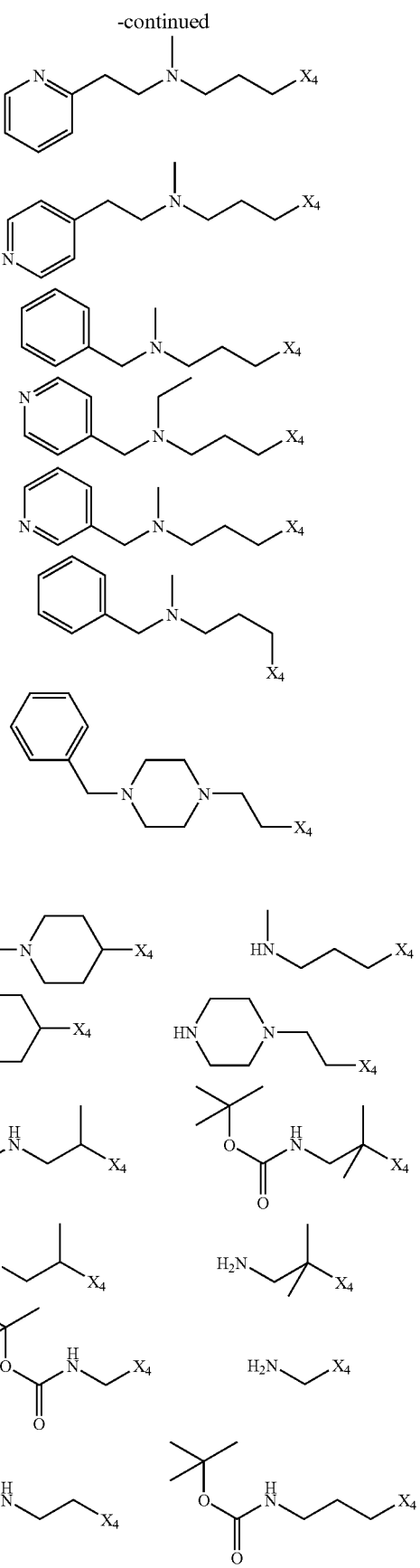

and R₄ represents one of the radicals below (when R₄ represents a radical comprising a secondary amine termination, for example propylaminomethyl, the compounds were obtained by catalytic hydrogenation in the presence of palladium on carbon of the corresponding N-benzyl derivatives; and when R₄ represents a radical comprising a primary amine termination, for example ethylamino, the compounds were obtained by acid treatment of the corresponding derivatives protected by a tertbutoxycarbonyl group).

-continued

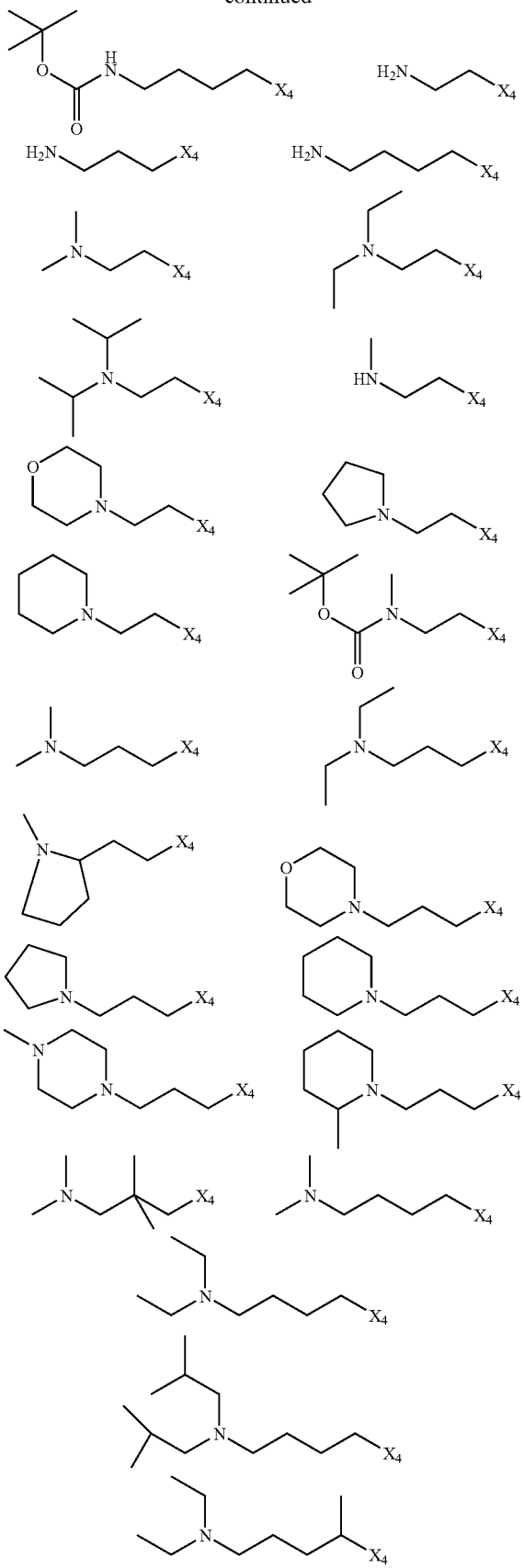
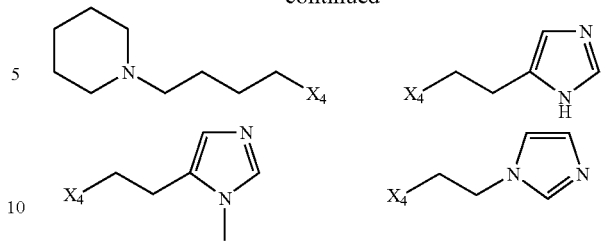

B. Preparation According to Reaction Diagram B:

The compounds of formula I according to the invention in which Y represents —S— and A represents —C(O)—, can be prepared according to the following Diagram B:

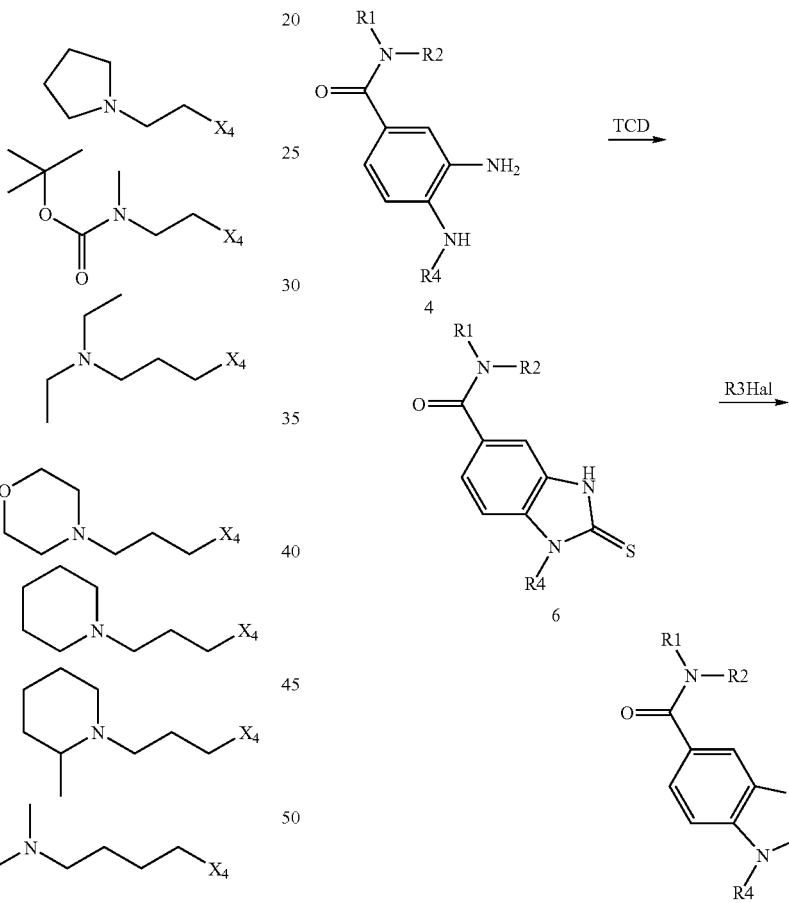

As described in Diagram B, the dianiline (4) can be treated with thiocarbonyldiimidazole (TCD) or thiophosgene in an inert organic solvent such as tetrahydrofuran, methylene chloride or chloroform at ambient temperature for 2 to 17 hours in order to produce derivative (6). Compound (6) is then alkylated by reaction with a halogen derivative such as an alkyl or benzyl iodide, bromide or chloride or a bromoketone, in the presence of a tertiary base such as triethylamine or diisopropylethylamine, or in the presence of a resin-supported tertiary base such as morpholinomethyl polystyrene resin, in an inert organic solvent such as tetrahydrofuran, choroform or methylene chloride, at a temperature of 20-70° C. for 3 to 24 hours. The resulting thiobenzimidazole (7) can be isolated, either by flash chromatography on silica gel, or by adding to the reaction mixture a polymer-supported nucleophilic reagent such as for example an aminomethyl polystyrene resin, and a polymer-supported electrophilic reagent such as for example 4-bromomethylphenoxymethyl polystyrene resin, followed by filtration and evaporation of the filtrate.

EXAMPLE B1

N,N-diisobutyl-1-{3-[methyl(2-pyridin-2-ylethyl)amino]propyl}-2-{[2-oxo-2-(3,4,5-trimethoxyphenyl)ethyl]thio}-1H-benzimidazole-5-carboxamide

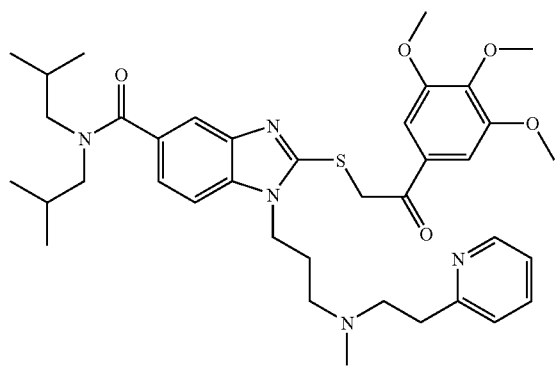

Stage 1: N,N-diisobutyl-1-{3-[methyl(2-pyridin-2-ylethyl)amino]propyl}-2-thioxo-2,3-dihydro-1H-benzimidazole-5-carboxamide A mixture of 3-amino-N,N-diisobutyl-4-({3-[methyl(2-pyridin-2-ylethyl)amino]propyl}amino)benzamide (1.52 g, 1 eq) and thiocarbonyldiimidazole (0.74 g, 1.2 eq) in THF (30 ml) is stirred at approximately 20° C. for 15 hours. After concentration under reduced pressure at 40° C., the residue obtained is taken up in dichloromethane (80 ml) and water (30 ml). After decanting and extracting, the combined organic phases are washed with salt water, dried over $Na_2SO_4$ then evaporated under reduced pressure at 40° C. Purification of the residue by flash chromatography on silica gel (eluent: 100% dichloromethane to dichloromethane/methanol 8:2) produces the expected compound in the form of a light beige foam (1.2 g; 72% yield).

MS/LC: MW calculated=481.7; m/Z=482.3 (MH+)

NMR (1H, 400 MHz, DMSO-$d_6$): δ0.64 (m, 6H), 0.91 (m, 6H), 1.79-2.03 (m, 4H), 2.18 (s, 3H), 2.37 (t, 3H, $^3J$=6.5 Hz), 2.66 (t, 2H, $^3J$=7 Hz), 2.83 (t, 2H, $^3J$=7 Hz), 3.19 (m, 2H), 3.24 (m, 2H), 4.16 (t, 2H, $^3J$=7 Hz), 7.05-7.65 (m, 6H), 8.43 (d, 1H), 12.79 (s, 1H).

Stage 2: N,N-diisobutyl-1-{3-[methyl(2-pyridin-2-ylethyl)amino]propyl}-2-{[2-oxo-2-(3,4,5-trimethoxyphenyl)ethyl]thio}-1H-benzimidazole-5-carboxamide Morpholinomethylpolystyrene resin (acquired from Novabiochem, 2 eq) and 2-bromo-1-(3,4,5-trimethoxyphenyl)ethanone are added successively to a solution of N,N-diisobutyl-1-{3-[methyl(2-pyridin-2-ylethyl)amino]propyl}-2-thioxo-2,3-dihydro-1H-benzimidazole-5-carboxamide in tetrahydrofuran. The mixture is stirred for 15 hours at approximately 20° C. then tetrahydrofuran, aminomethylpoystyrene resin (2 eq, acquired from Novabiochem) and 4-bromomethylphenoxymethyl-polystyrene resin (3 eq, acquired from Novabiochem) are added. After stirring for 6 hours, the mixture is filtered on frit. The filtrate is then concentrated to dryness under reduced pressure at 40° C. in order to produce the expected compound.

MS/LC: MW calculated=689.9; m/z=690.5 (MH+)

NMR ($^1$H, 400 MHz, DMSO-$d_6$): δ0.61 (m, 6H), 0.91 (m, 6H), 1.71-2.03 (m, 4H), 2.19 (s, 3H), 2.35 (t, 3H, $^3J$=6.5 Hz), 2.67 (t, 2H, $^3J$=7 Hz), 2.85 (t, 2H, $^3J$=7 Hz), 3.08-3.30 (m, 4H), 3.75 (s, 3H), 3.84 (s, 6H), 4.15 (t, 2H, $^3J$=7 Hz), 5.09 (s, 2H), 7.11-7.67 (m, 8H), 8.45 (d, 1H).

The following compounds were prepared according to reaction diagram B and in a similar manner to the procedure described for the synthesis of N,N-diisobutyl-1-{3-[methyl(2-pyridin-2-ylethyl)amino]propyl}-2-{[2-oxo-2-(3,4,5-trimethoxyphenyl)ethyl]thio}-1H-benzimidazole-5-carboxamide

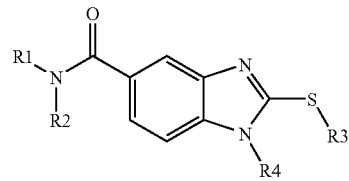

In the above formula, $R_1R_2N$ represents one of the radicals below:

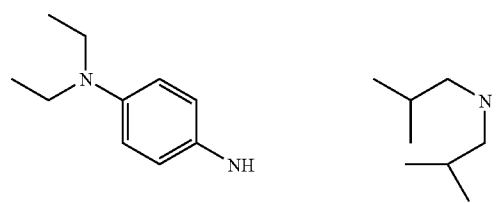

$R_3$ represents one of the radicals below

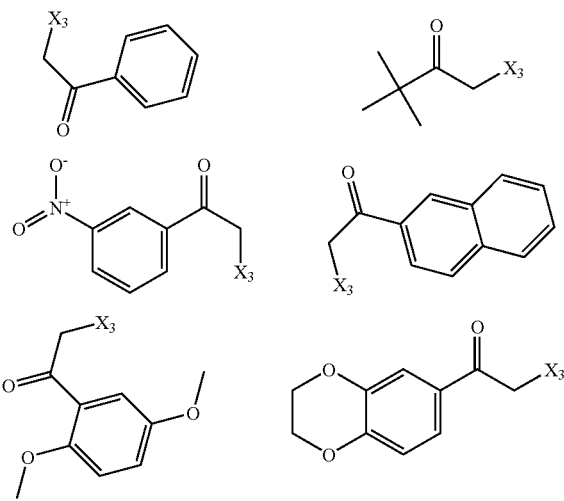

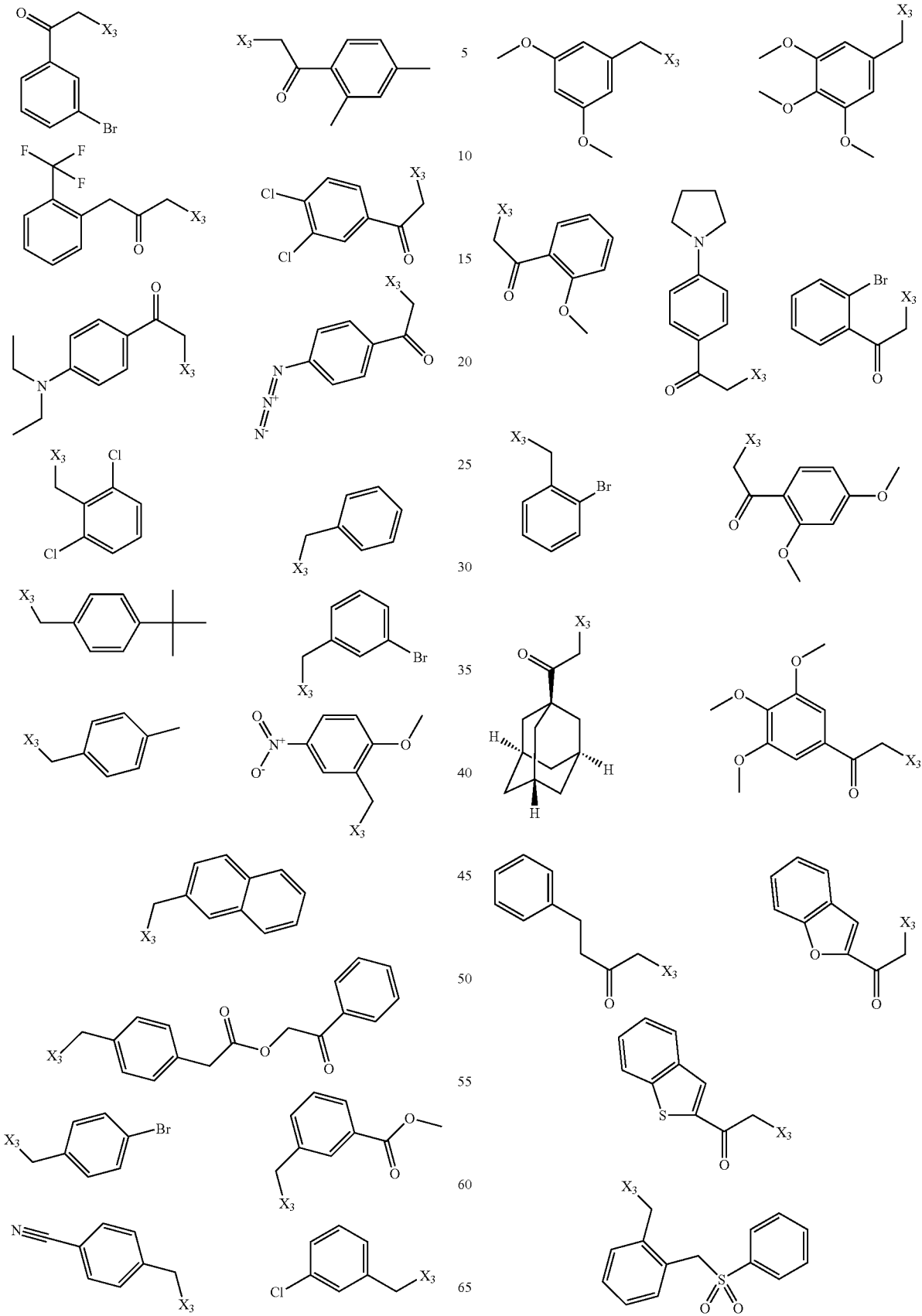

-continued
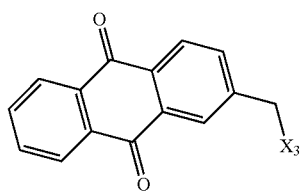 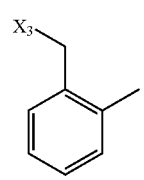
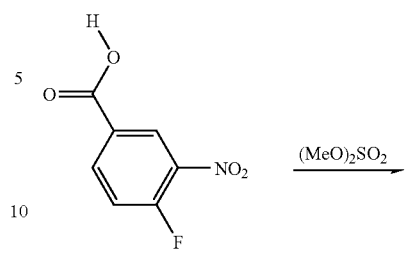
1
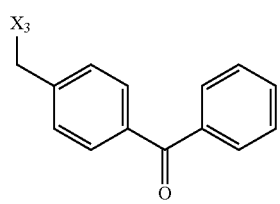
and R₄ represents one of the radicals below
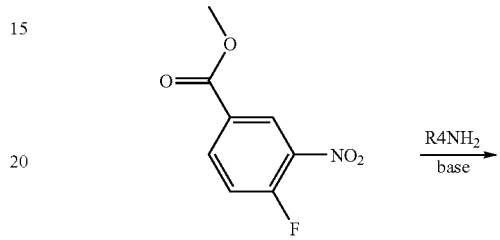
8
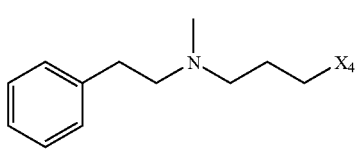
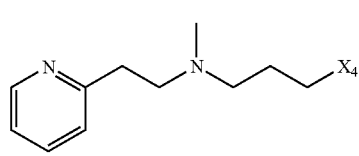
9
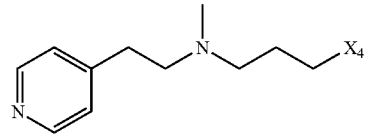
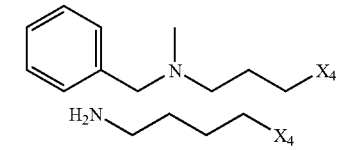 
10
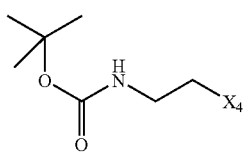 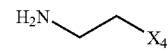
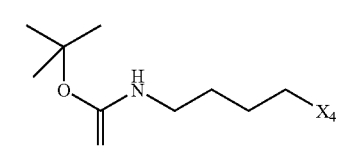
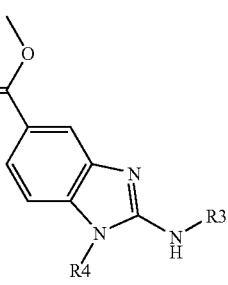
11
C. Preparation According to Reaction Diagram C:
The compounds of formula I according to the invention in which Y represents —NH— and A represents —C(O)—, can be prepared according to the following Diagram C:

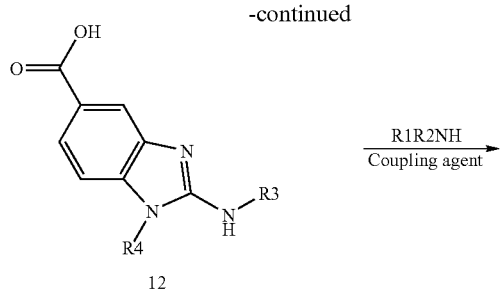

12

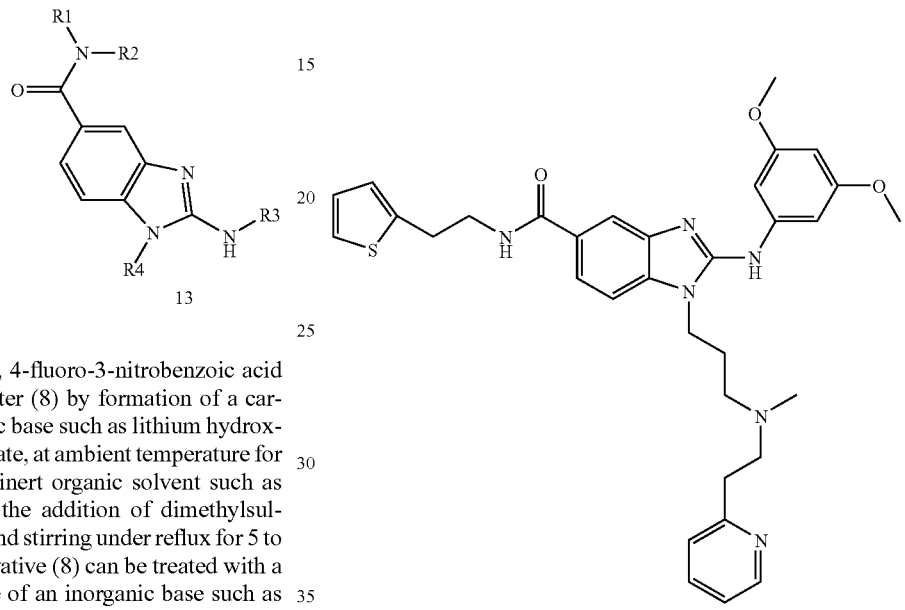

As described in Diagram C, 4-fluoro-3-nitrobenzoic acid can be converted to methyl ester (8) by formation of a carboxylate salt using an inorganic base such as lithium hydroxide dihydrate or cesium carbonate, at ambient temperature for 30 minutes to 2 hours, in an inert organic solvent such as tetrahydrofuran, followed by the addition of dimethylsulphate at ambient temperature and stirring under reflux for 5 to 15 hours. The fluorinated derivative (8) can be treated with a primary amine in the presence of an inorganic base such as cesium or potassium carbonate in an inert organic solvent such as dimethylformamide or acetonitrile at a temperature of 20-70° C. for 2 to 16 hours in order to produce derivative (9). The nitro function of compound (9) is reduced by treatment with tin chloride dihydrate in an inert solvent such as ethyl acetate or dimethylformamide, at a temperature of 60-80° C. for 3 to 15 hours, or by catalytic hydrogenation in the presence of 10% palladium on carbon in an inert solvent such as methanol, ethanol, ethyl acetate or a mixture of these solvents, at a temperature of 18-25° C., for 2 to 8 hours, in order to produce dianiline (10). Derivative (10) is then treated with an isothiocyanate in the presence of a coupling agent such as diisopropylcarbodiimide or dicyclohexylcarbodiimide in an inert solvent such as tetrahydrofuran, methylene chloride or chloroform at a temperature of 20-70° C. for 2 to 72 hours in order to produce derivative (11). Alternatively, derivative (10) can be treated with an isothiocyanate in an inert solvent such as tetrahydrofuran, methylene chloride or chloroform, then the resulting thiourea can be treated with methyl iodide in a polar solvent such as ethanol for 3 to 24 hours at a temperature of 20-70° C. in order to produce (11). The methyl ester (11) can then be saponified in the presence of an inorganic base such as lithium hydroxide dihydrate in a mixture of polar solvents such as water and tetrahydrofuran at a temperature of 20 to 70° C. for 3 to 17 hours. The resulting acid (12) can be coupled with a primary or secondary amine in the presence of a coupling agent such as diisopropylcarbodiimide, dicyclohexylcarbodiimide or carbonyldiimidazole, with or without 1-hydroxybenzotriazole (HOBt) in an inert organic solvent such as methylene chloride, tetrahydrofuran or dimethylformamide at ambient temperature for 3 to 24 hours. The corresponding amide (13) can be isolated, either by flash chromatography on silica gel, or by adding to the reaction mixture a polymer-supported nucleophilic reagent such as for example an aminomethyl polystyrene resin and a polymer-supported electrophilic reagent such as for example methylisothiocyanate polystyrene resin, followed by filtration and evaporation of the filtrate.

EXAMPLE C1

1-(2-[(3,5-dimethoxyphenyl)amino]-1-{3-[methyl(2-pyridin-2-ylethyl)amino]propyl}-1H-benzimidazol-5-yl)-3-thien-2-yl propan-1-one Stage 1: methyl 4-fluoro-3-nitrobenzoate Lithium hydroxide monohydrate (4.5 g, 1 eq) is added in small portions to a solution of 4-fluoro-3-nitrobenzoic acid (20 g, 1 eq) in tetrahydrofuran (100 ml). After stirring for 1 hour at approximately 20° C., dimethylsulphate (10.2 ml) is added dropwise to the yellow precipitate. The reaction mixture is then heated under reflux for 8 hours then concentrated under reduced pressure at 40° C. The residue is diluted in dichloromethane and $Na_2CO_3$ saturated water. After decanting and extracting, the combined organic phases are washed with salt water, dried over sodium sulphate and concentrated under reduced pressure at 40° C. The yellow solid obtained is recrystallized from a diethyl ether/petroleum ether mixture in order to produce the expected compound in the form of a light yellow powder (16.7 g, 78% yield). Melting point=59° C.

NMR ($^1$H, 400 MHz, DMSO-$d_6$): δ3.99 (s, 3H), 7.39 (m, 1H), 8.33 (s, 1H), 8.74 (s, 1H).

Stage 2: methyl 4-({3-[methyl(2-pyridin-2-ylethyl)amino]propyl}amino)-3-nitro benzoate A mixture of methyl 4-fluoro-3-nitrobenzoate (5.08 g, 1 eq), of N-(2-pyridin-2-ylethyl)propane-1,3-diamine (5.4 g, 1.2 eq) and potassium carbonate (7.0 g, 2 eq) in acetonitrile (180 ml) is heated under reflux for 3 hours then concentrated under reduced pressure at 40° C. The residue is taken up in dichloromethane (150 ml) and water (60 ml). After decanting and extracting, the combined organic phases are washed with salt water, dried over $Na_2SO_4$ then evaporated under reduced pressure at 40° C. Purification of the compound by flash chromatography on silica gel (eluent: dichloromethane to dichloromethane/methanol 9:1) produces the expected compound in the form of an orange-coloured oil (9.2 g; 97% yield).

MS/LC: MW calculated=372.4; m/z=373.3 (MH+)

NMR ($^1$H, 400 MHz, DMSO-$d_6$): δ1.75 (m, 2H), 2.23 (s, 3H), 2.48 (t, 3H, $^3$J=6 Hz), 2.71 (t, 2H, $^3$J=7.8 Hz), 2.86 (t, 2H, $^3$J=7.8 Hz), 3.35 (m, 2H), 3.81 (s, 3H), 7.05 (d, 1H), 7.10 (m, 1H), 7.23 (d, 1H), 7.59 (m, 1H), 7.93 (m, 1H), 8.40 (d, 1H), 8.59 (s, 1H), 8.87 (t, 1H, $^3$J=5 Hz).

Stage 3: methyl 3-amino-4-({3-[methyl(2-pyridin-2-ylethyl)amino]propyl}amino)benzoate Methyl 4-({3-[methyl(2-pyridin-2-ylethyl)amino]propyl}amino)-3-nitrobenzoate (9.1 g) in solution in an ethyl acetate/methanol mixture and 10% palladium on carbon (910 mg) are added together in an autoclave. After stirring for 4 hours under a hydrogen atmosphere (3 bars), the catalyst is eliminated by filtration on Celite and the filtrate is concentrated under reduced pressure at 40° C. in order to produce the expected compound in the form of an oil (8.2 g, 98% yield).

MS/LC: MW calculated=342.4; m/z=343.3 (MH+)

NMR ($^1$H, 400 MHz, DMSO-$d_6$): δ 1.71 (m, 2H), 2.21 (s, 3H), 2.46 (t, 3H, $^3$J=6.8 Hz), 2.68 (t, 2H, $^3$J=7 Hz), 2.86 (t, 2H, $^3$J=7 Hz), 3.05 (m, 2H), 3.71 (s, 3H), 4.70 (s, 2H), 5.23 (t, 1H, $^3$J=7 Hz), 6.37 (d, 1H), 7.14-7.26 (m, 4H), 7.64 (m, 1H), 8.45 (m, 1H).

Stage 4: methyl-2-[(3,5-dimethoxyphenyl)amino]-1-{3-[methyl(2-pyridin-2-ylethyl) amino]propyl}-1H-benzimidazole-5-carboxylate 3,5 dimethoxyphenylisothiocyanate (571 mg, 1 eq) and diisopropylcarbodiimide (1.35 ml, 4 eq) are added successively to a solution of methyl 3-amino-4-({3-[methyl(2-pyridin-2-ylethyl)amino]propyl}amino)benzoate (1.0 g, 1 eq) in tetrahydrofuran (10 ml). The mixture is heated under reflux for 18 hours then cooled down to ambient temperature and concentrated under reduced pressure at 40° C. The residue is taken up in ethyl acetate (100 ml) and water (40 ml). After decanting and extracting, the combined organic phases are washed with salt water, dried over $Na_2SO_4$ then evaporated under reduced pressure at 40° C. Purification of the residue by flash chromatography on silica gel (eluent: dichloromethane/methanol 99:1 to 98:2) produces the expected compound in the form of a beige foam (1.12 g; 76% yield).

MS/LC: MW calculated=503.6 m/z=504.3 (MH+)

NMR ($^1$H, 400 MHz, CDCl$_3$): δ 2.08 (m, 2H), 2.40 (t, 2H, $^3$J=7 Hz), 2.45 (s, 3H), 2.99 (t, 2H, $^3$J=7 Hz), 3.09 (t, 2H, $^3$J=7 Hz), 3.82 (s, 6H), 3.93 (s, 3H), 4.01 (t, 2H, $^3$J=6 Hz), 6.15 (m, 1H), 6.92-7.54 (m, 6H), 7.87 (m, 1H), 8.25 (s, 1H), 8.51 (m, 1H), 9.37 (s, 1H).

Stage 5: 2-[(3,5-dimethoxyphenyl)amino]-1-{3-[methyl(2-pyridin-2-ylethyl)amino]propyl}-1H-benzimidazole-5-carboxylic acid Lithium hydroxide (0.350 g, 4 eq) is added to a solution of methyl-2-[(3,5-dimethoxyphenyl)amino]-1-{3-[methyl(2-pyridin-2-ylethyl)amino]propyl}-1H-benzimidazole-5-carboxylate (1.05 g, 1 eq) in a mixture of tetrahydrofuran (10 ml) and water (5 ml). The mixture is stirred at 65° C. for 18 hours then cooled down to ambient temperature and concentrated under reduced pressure at 40° C. Ethyl acetate and water are added to the residue. The mixture is acidified by adding acetic acid to pH 5. After decanting and extracting, the combined organic phases are dried over sodium sulphate and concentrated under reduced pressure. Purification by flash chromatography on silica gel (eluent: dichloromethane/ethanol 95/5 to 70/30) produces the expected compound in the form of a white foam (0.93 g, 91% yield).

MS/LC: MW calculated=489.6; m/z=490.1 (MH+)

NMR ($^1$H, 400 MHz, DMSO-$d_6$): δ 1.88 (m, 2H), 2.23 (s, 3H), 2.31 (t, 2H, $^3$J=6.5 Hz), 2.74 (t, 2H, $^3$J=7 Hz), 2.91 (t, 2H, $^3$J=7 Hz), 3.72 (s, 6H), 4.14 (t, 2H, $^3$J=6.5 Hz), 6.14 (m, 1H), 7.09-7.72 (m, 8H), 7.93 (s, 1H), 8.44 (m, 1H), 9.21 (s, 1H).

Stage 6: 1-(2-[(3,5-dimethoxyphenyl)amino]-1-{3-[methyl(2-pyridin-2-ylethyl)amino]propyl}-1H-benzimidazol-5-yl)-3-thien-2-ylpropan-1-one Carbonyldiimidazole (10.5 mg, 1.3 eq) in solution in chloroform (0.2 ml) is added to a solution of 2-[(3,5-dimethoxyphenyl)amino]-1-{3-[methyl(2-pyridin-2-ylethyl)amino]propyl}-1H-benzimidazole-5-carboxylic acid (24 mg, 1 eq) in a mixture of dimethylformamide (0.2 ml) and tetrahydrofuran (0.4 ml). The mixture is stirred for 15 hours at approximately 20° C. then thiophene-2-ethylamine (13 mg, 2 eq) in solution in tetrahydrofuran (0.1 ml) is added. After stirring for 15 hours at approximately 20° C., aminomethyl polystyrene resin (2 eq), TBD-methyl polystyrene resin (2 eq) and methylisothiocyanate polystyrene resin (4 eq) are added to the mixture diluted in dichloromethane. After stirring for 6 hours at approximately 20° C., the mixture is filtered and the filtrate is concentrated under reduced pressure at 40° C. in order to produce the expected compound in the form of an oil (27 mg, 90% yield).

MS/LC: MW calculated=598.8; m/z=599.2 (MH+)

NMR ($^1$H, 400 MHz, DMSO-$d_6$): δ 1.87 (m, 2H), 2.26 (s, 3H), 2.48 (t, 2H, $^3$J=6.5 Hz), 2.78 (m, 2H), 2.93 (t, 2H, $^3$J=7 Hz), 3.08 (t, 2H, $^3$J=7 Hz), 3.50 (m, 2H), 3.72 (s, 6H), 4.14 (t, 2H, $^3$J=6.5 Hz), 6.14 (m, 1H), 6.92-7.93 (m, 12H), 8.45 (m, 1H), 9.16 (s, 1H).

The following compounds were prepared according to reaction diagram C and in a similar manner to the procedure described for the synthesis of 1-(2-[(3,5-dimethoxyphenyl)amino]-1-{3-[methyl(2-pyridin-2-ylethyl)amino]propyl}-1H-benzimidazol-5-yl)-3-thien-2-ylpropan-1-one:

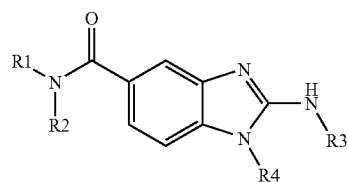

In the above formula, $R_1R_2N$ represents one of the radicals below:

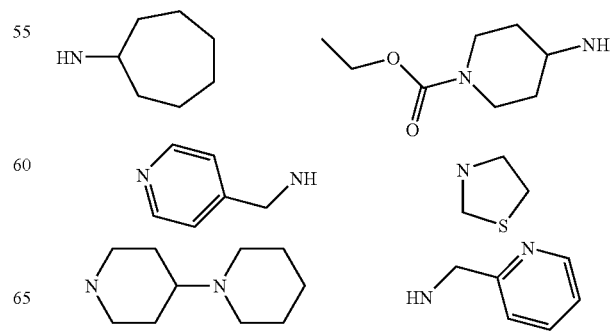

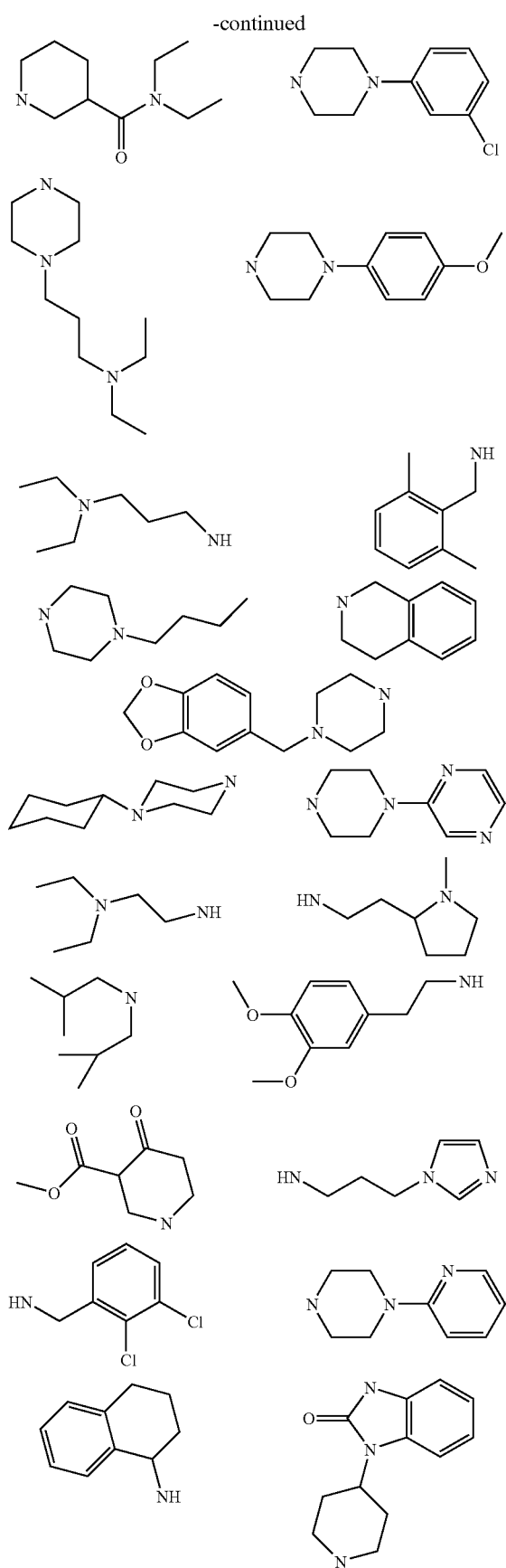
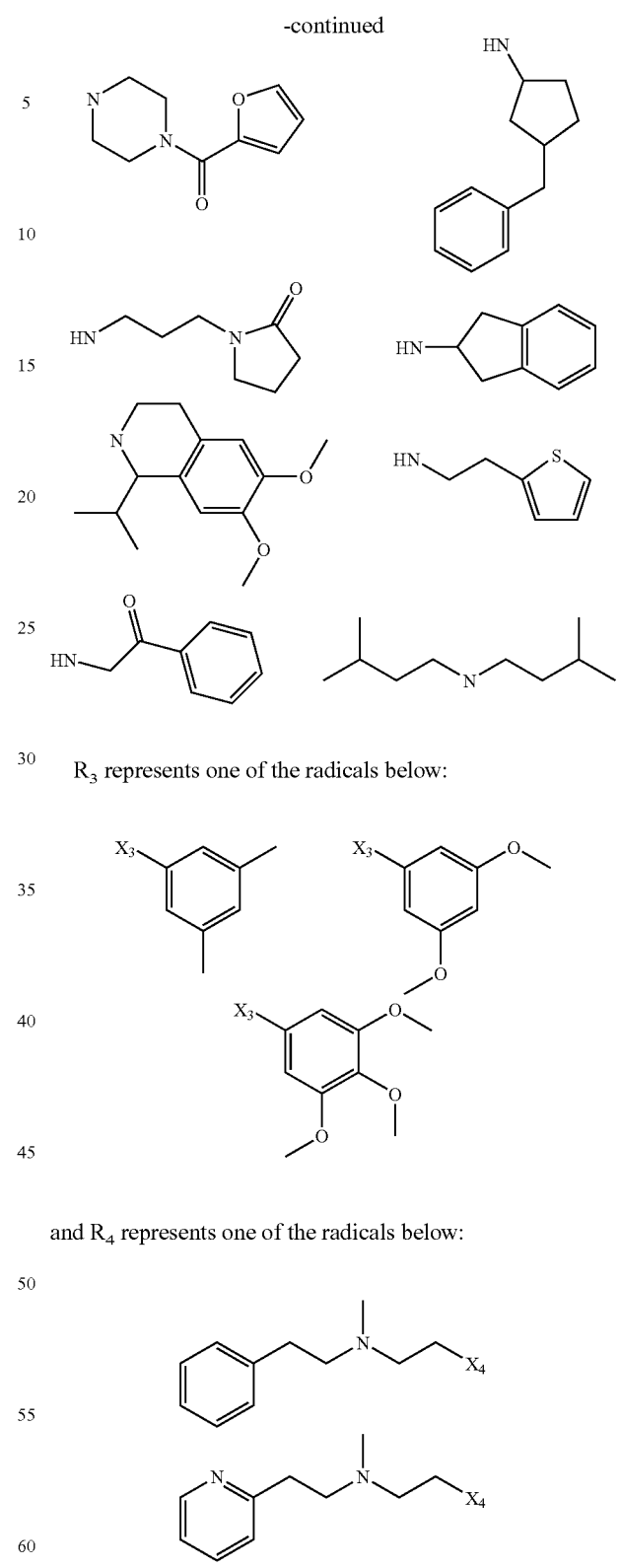
$R_3$ represents one of the radicals below:
and $R_4$ represents one of the radicals below:
D. Preparation According to Reaction Diagram D:
The compounds of formula I according to the invention in which Y represents —S— and A represents —C(O)—, can be prepared according to the following Diagram D:

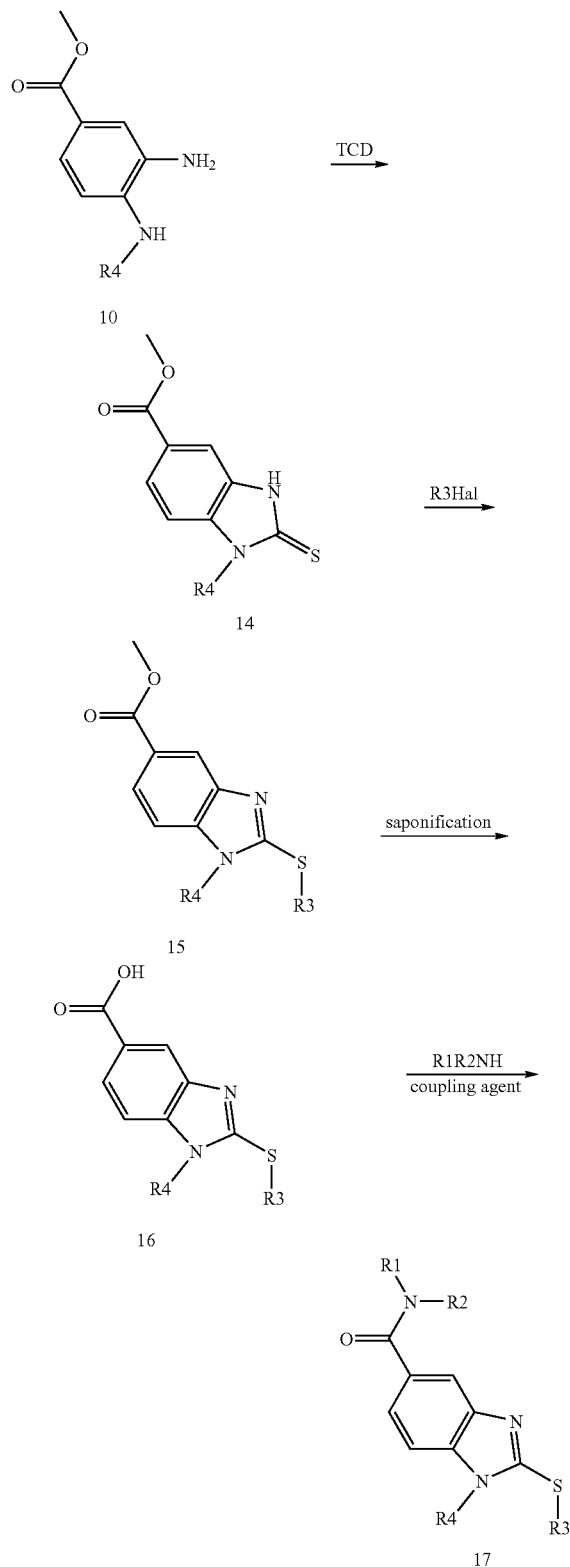

Compound (14) is then alkylated by reacting with a halogenated derivative such as an alkyl or benzyl iodide, bromide or chloride or a bromoketone, in the presence of a tertiary base such as triethylamine or diisopropylethylamine, in an inert organic solvent such as tetrahydrofuran, choroform or methylene chloride, at a temperature of 20-70° C. for 3 to 24 hours in order to produce the thiobenzimidazole derivative (15). The methyl ester (15) can then be saponified in the presence of an inorganic base such as lithium hydroxide monohydrate in a mixture of polar solvents such as water and tetrahydrofuran at a temperature of 20 to 70° C. for 3 to 17 hours. The resulting acid (16) can be coupled with a primary or secondary amine in the presence of a coupling agent such as diisopropylcarbodiimide, dicyclohexylcarbodiimide or carbonyldiimidazole, with or without 1-hydroxybenzotriazole (HOBt) in an inert organic solvent such as methylene chloride, tetrahydrofuran or dimethylformamide at ambient temperature for 3 to 24 hours. The corresponding amide (17) can be isolated, either by flash chromatography on silica gel, or by adding a polymer-supported nucleophilic reagent such as for example an aminomethyl polystyrene resin and a polymer-supported electrophilic reagent such as for example methylisothiocyanate polystyrene resin to the reaction mixture, followed by filtration and evaporation of the filtrate.

EXAMPLE D1

3-(2-[(3-bromobenzyl)sulphanyl]-5-{[4-(1-pyrrolidinyl)-1-piperidinyl]carbonyl}-1H-benzimidazol-1-yl)-N-methyl-N-[2-(2-pyridinyl)ethyl]-1-propanamine

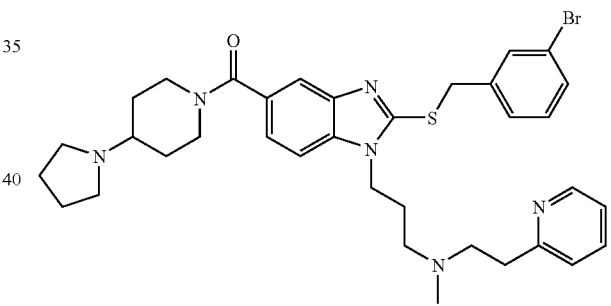

Stage 1: methyl 1-{3-[methyl(2-pyridin-2-ylethyl)amino]propyl}-2-thioxo-2,3-dihydro-1H-benzimidazole-5-carboxylate A mixture of methyl 3-amino-4-({3-[methyl(2-pyridin-2-ylethyl)amino]propyl}amino)benzoate (4.09 g, 1 eq) and thiocarbonyldiimidazole (2.77 g, 1.3 eq) in tetrahydrofuran (100 ml) is stirred at approximately 20° C. for 15 hours. After concentration under reduced pressure at 40° C., the residue obtained is taken up in dichloromethane (150 ml) and water (50 ml). After decanting and extracting, the combined organic phases are washed with salt water, dried over $Na_2SO_4$ then evaporated under reduced pressure at 40° C. Purification by flash chromatography on silica gel (eluent: 100% dichloromethane to dichloromethane/methanol 9:1) produces the expected compound in the form of a foam (3.94 g; 85% yield).

MS/LC: MW calculated 384.5; m/z=385.2 (MH+)

NMR ($^1$H, 400 MHz, DMSO-$d_6$): δ 1.86 (m, 2H), 2.18 (s, 3H), 2.37 (t, 3H, $^3$J=6.8 Hz), 2.65 (t, 2H, $^3$J=7 Hz), 2.84 (t, 2H, $^3$J=7 Hz), 3.85 (s, 3H), 4.16 (t, 2H, $^3$J=7 Hz), 7.16-7.81 (m, 6H), 8.44 (m, 1H), 12.95 (s, 1H).

As described in Diagram D, dianiline (10) can be treated with thiocarbonyldiimidazole (TCD) or thiophosgene in an inert organic solvent such as tetrahydrofuran, at ambient temperature for 2 to 17 hours in order to produce derivative (14).

Stage 2: methyl 2-[(3-bromobenzyl)thio]-1-{3-[methyl(2-pyridin-2-ylethyl)amino]propyl}-1H-benzimidazole-5-carboxylate Triethylamine (0.82 ml, 1.6 eq) and 3-bromobenzylbromide (0.97 g, 1 eq) are added successively to a solution of methyl 1-{3-[methyl(2-pyridin-2-ylethyl)amino]propyl}-2-thioxo-2,3-dihydro-1H-benzimidazole-5-carboxylate (1.5 g) in tetrahydrofuran (30 ml). The mixture is stirred for 15 hours at approximately 20° C. then concentrated under reduced pressure at 40° C. The residue obtained is diluted in ethyl acetate and water. After decanting and extracting, the organic phases are washed with salt water, dried over sodium sulphate and concentrated under reduced pressure at 40° C. Purification by flash chromatography on silica gel (eluent: dichloromethane/methanol 95/5 to 90/10) produces the expected compound in the form of a colourless oil (1.5 g; 70% yield).

MS/LC: MW calculated=553.5; m/z=553.3 (MH+)

NMR ($^1$H, 400 MHz, DMSO-$d_6$): δ 1.76 (m, 2H), 2.14 (s, 3H), 2.27 (t, 3H, $^3$J=6.5 Hz), 2.62 (t, 2H, $^3$J=7 Hz), 2.81 (t, 2H, $^3$J=7 Hz), 3.86 (s, 3H), 4.06 (t, 2H, $^3$J=7 Hz), 4.61 (s, 2H), 7.15-7.82 (m, 9H), 8.13 (s, 1H), 8.43 (d, 1H).

Stage 3: 2-[(3-bromobenzyl)thio]-1-{3-[methyl(2-pyridin-2-ylethyl)amino]propyl}-1H-benzimidazole-5-carboxylic acid Lithium hydroxide (0.315 g, 3 eq) is added to a solution of methyl 2-[(3-bromobenzyl)thio]-1-{3-[methyl(2-pyridin-2-ylethyl)amino]propyl}-1H-benzimidazole-5-carboxylate (1.03 g, 1 eq) in a mixture of tetrahydrofuran (10 ml) and water (5 ml). The mixture is heated under reflux for 18 hours then cooled down to ambient temperature and concentrated under reduced pressure at 40° C. Ethyl acetate and water are added to the residue. The mixture is acidified by adding acetic acid to pH 5. After decanting and extracting, the combined organic phases are dried over sodium sulphate and concentrated under reduced pressure. Purification by flash chromatography on silica gel (eluent: dichloromethane/methanol 95/5 to 80/20) produces the expected compound in the form of a foam (0.85 g, 85% yield).

MS/LC: MW calculated=539.5; m/z=539.2 (MH+)

NMR ($^1$H, 400 MHz, DMSO-$d_6$): δ1.76 (m, 2H), 2.14 (s, 3H), 2.29 (t, 3H, $^3$J=6.5 Hz), 2.62 (t, 2H, $^3$J=7 Hz), 2.82 (t, 2H, $^3$J=7 Hz), 4.04 (t, 2H, $^3$J=7 Hz), 4.61 (s, 2H), 7.15-7.82 (m, 9H), 8.10 (s, 1H), 8.43 (d, 1H).

Stage 4: 3-(2-[(3-bromobenzyl)sulphanyl]-5-{[4-(1-pyrrolidinyl)-1-piperidinyl]carbonyl}-1H-benzimidazol-1-yl)-N-methyl-N-[2-(2-pyridinyl)ethyl]-1-propanamine Carbonyldiimidazole (10.5 mg, 1.3 eq) in solution in chloroform (0.2 ml) is added to a solution of 2-[(3-bromobenzyl)thio]-1-{3-[methyl(2-pyridin-2-ylethyl)amino]propyl}-1H-benzimidazole-5-carboxylic acid (27 mg, 1 eq) in a mixture of dimethylformamide (0.2 ml) and tetrahydrofuran (0.4 ml). The mixture is stirred for 15 hours at approximately 20° C. then 4-(1-pyrrolidinyl)piperidine (15 mg, 2 eq) is added. After stirring for 15 hours at approximately 20° C., aminomethyl polystyrene resin (2 eq, acquired from Novabiochem), TBD-methyl polystyrene resin (2 eq, acquired from Novabiochem) and methylisothiocyanate polystyrene resin (4 eq, acquired from Novabiochem) are added to the mixture diluted in dichloromethane. After stirring for 6 hours at approximately 20° C., the mixture is filtered and the filtrate is concentrated under reduced pressure at 40° C. in order to produce the expected compound in the form of an oil (28 mg, 84% yield).

MS/LC: MW calculated=675.7; m/z=674.2 (MH+)

NMR ($^1$H, 400 MHz, CDCl$_3$): δ 1.4-1.98 (m, 10H), 2.26 (s, 3H), 2.32 (m, 5H), 2.60-3.15 (m, 8H), 3.81 (m, 1H), 4.01 (t, 2H, $^3$J=7 Hz), 4.50 (m, 1H), 4.57 (s, 2H), 7.08-7.72 (m, 10H), 8.51 (d, 1H).

The following compounds were prepared according to reaction Diagram D and in a similar manner to the procedure described for the synthesis of 3-(2-[(3-bromobenzyl)sulphanyl]-5-{[4-(1-pyrrolidinyl)-1-piperidinyl]carbonyl}-1H-benzimidazol-1-yl)-N-methyl-N-[2-(2-pyridinyl)ethyl]-1-propanamine:

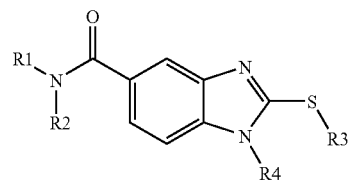

In the above formula, R$_1$R$_2$N represents one of the radicals below:

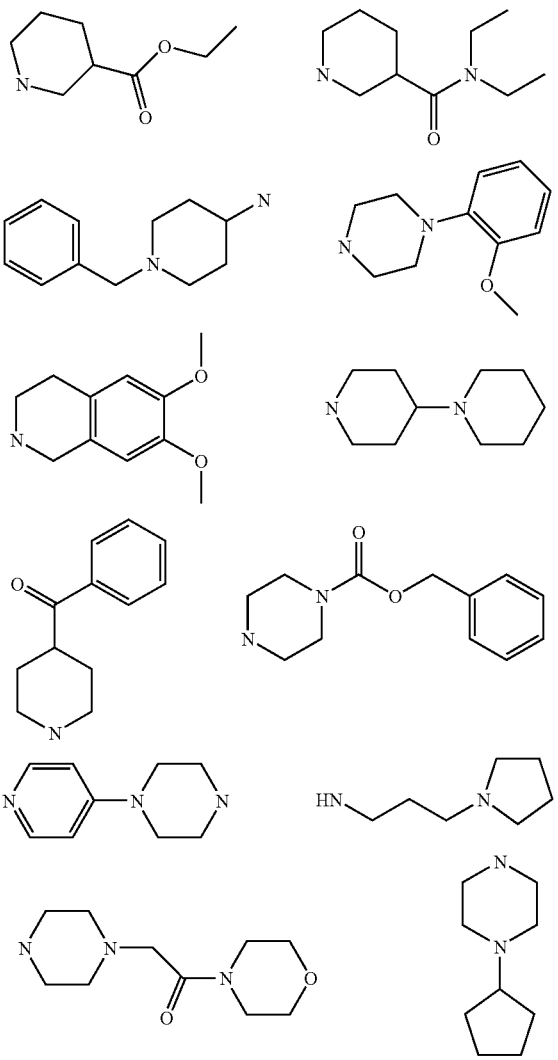

-continued
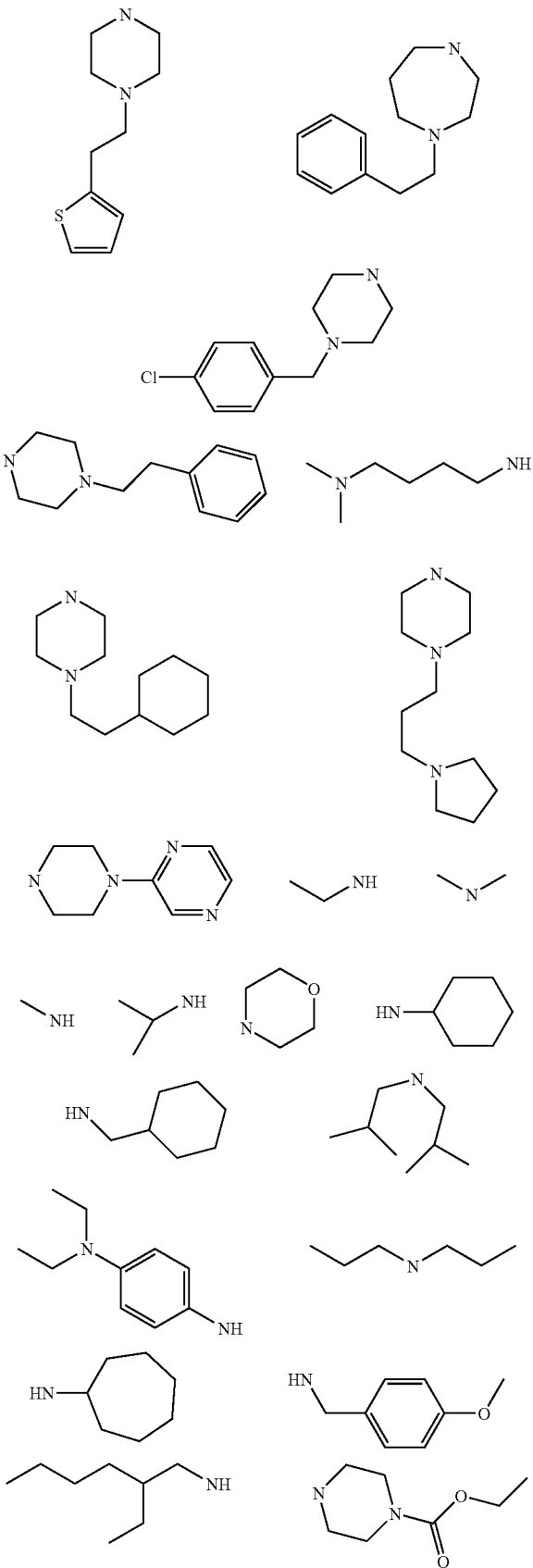
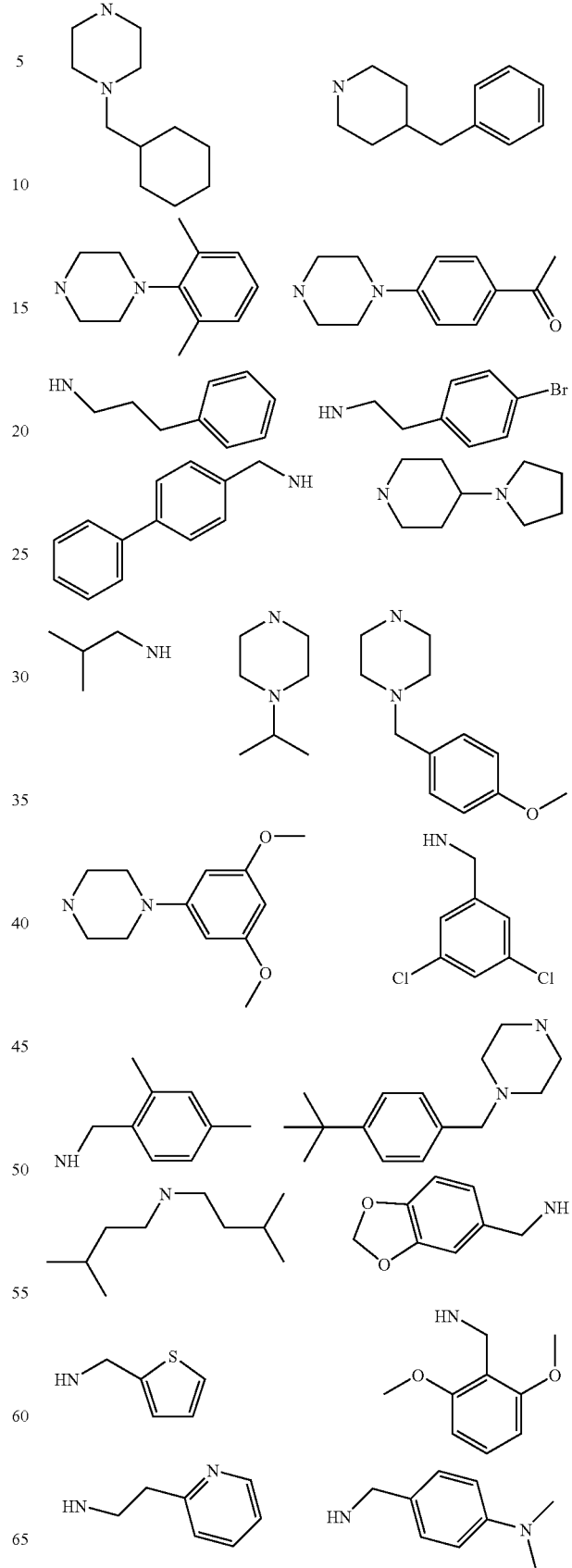

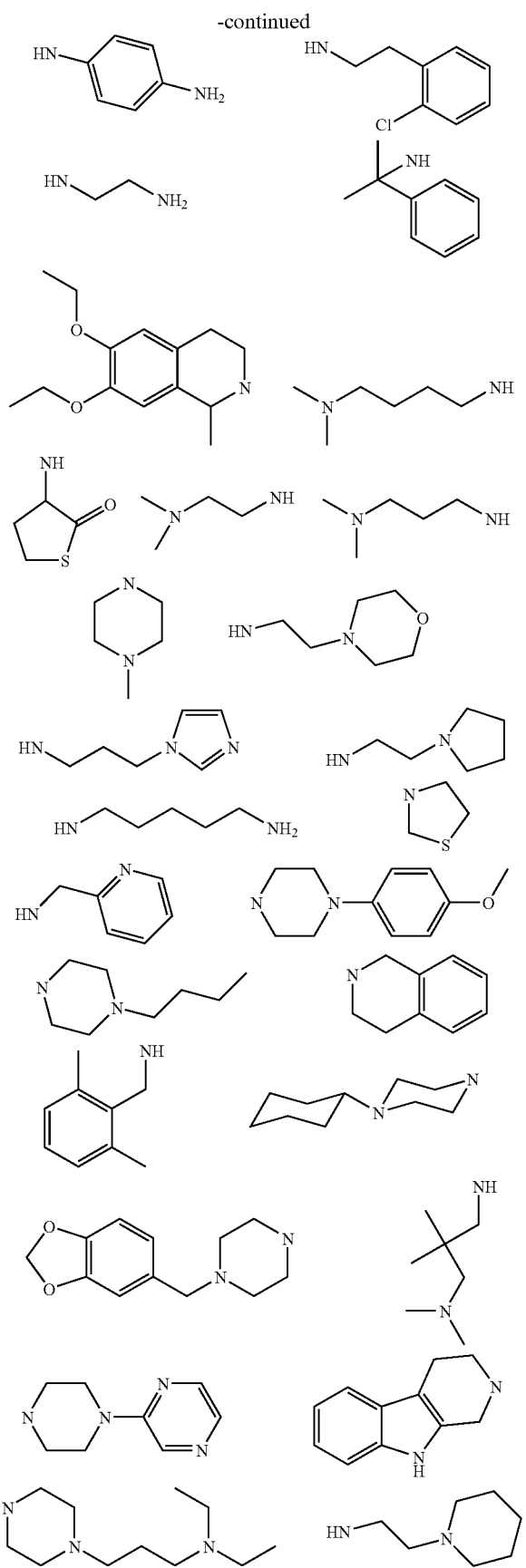
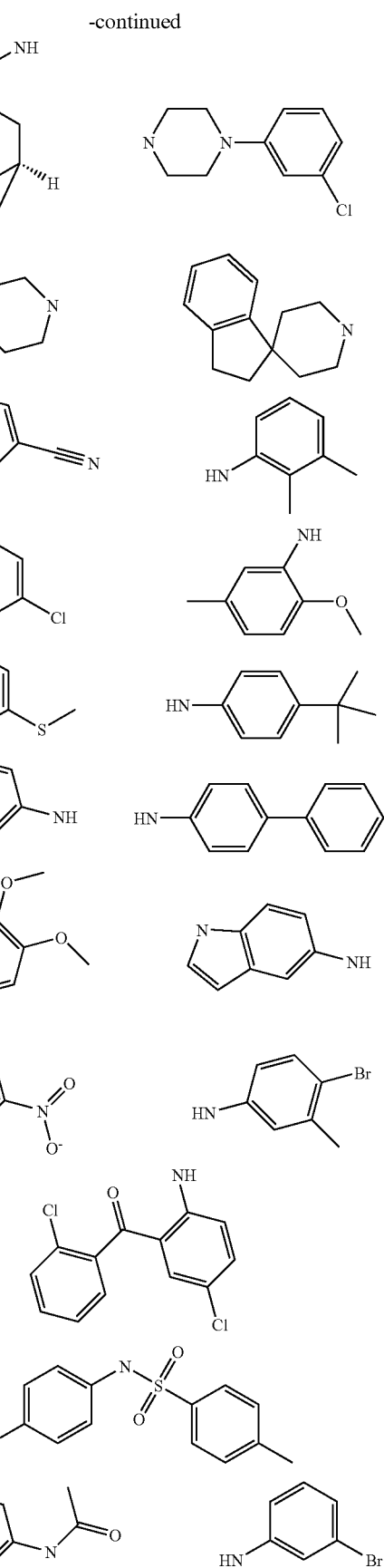

-continued

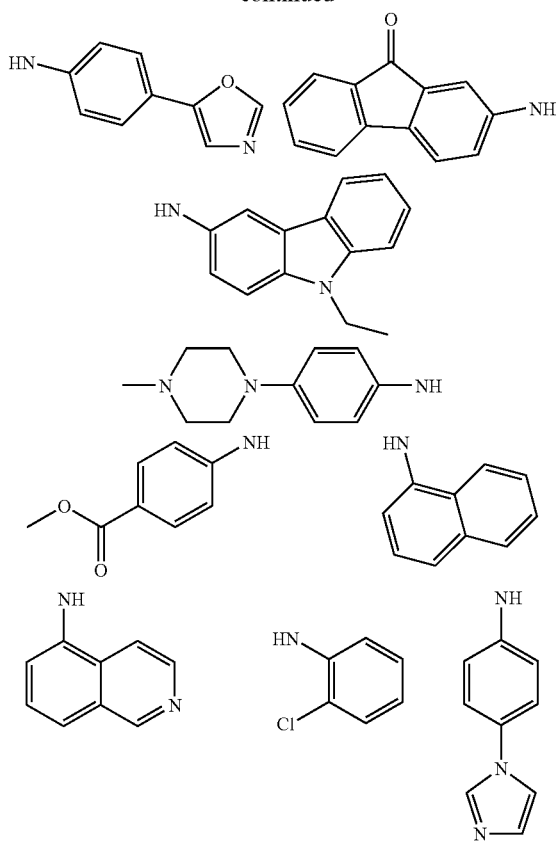

$R_3$ represents one of the radicals below:

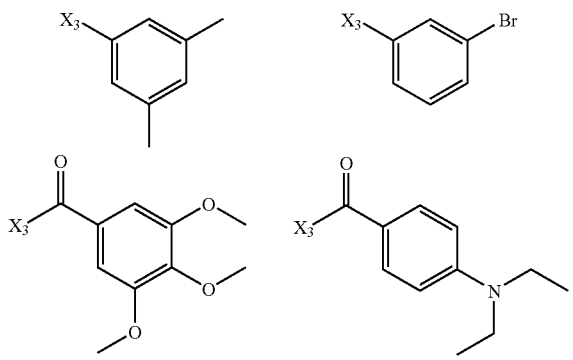

and $R_4$ represents one of the radicals below:

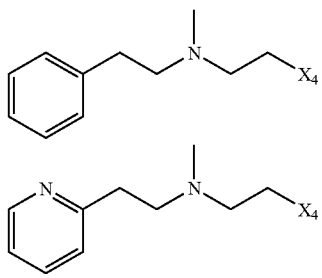

E. Preparation According to Reaction Diagram E:

The compounds of formula I according to the invention in which A represents —(CH$_2$)— can be prepared from compounds in which A represents —C(O)—, according to the following Diagram E:

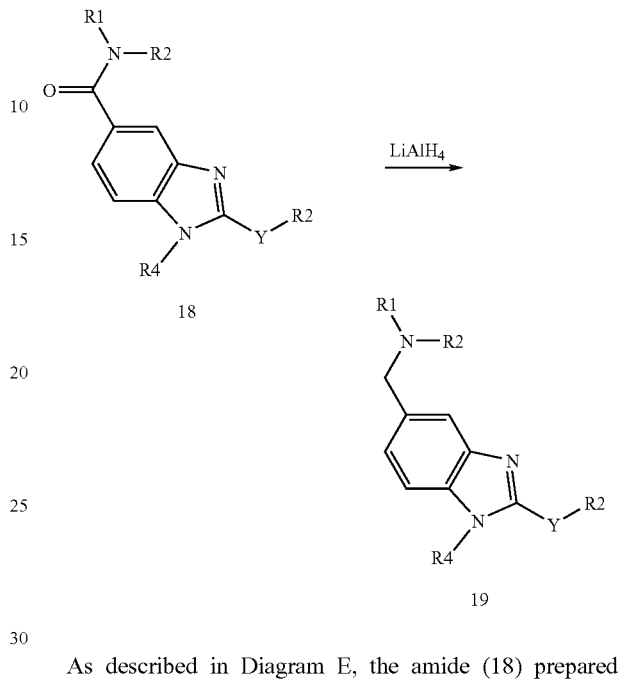

As described in Diagram E, the amide (18) prepared according to reaction diagrams A or B, can be reduced to the corresponding amine (19) using borane or lithium aluminium hydride in an aprotic solvent such as tetrahydrofuran or diethyl ether at a temperature of 0 to 70° C., for 1 to 6 hours.

EXAMPLE E1

5-[(diisobutylamino)methyl]-1-(3-{methyl[2-(2-pyridinyl)ethyl]amino}propyl)-N-(3,4,5-trimethoxyphenyl)-1H-benzimidazol-2-amine

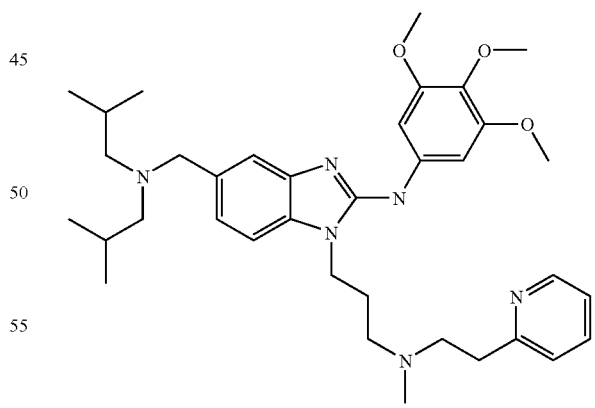

A molar solution of lithium aluminium hydride in tetrahydrofuran (0.83 ml, 5 eq) is added dropwise to a solution of N,N-diisobutyl-1-{3-[methyl(2-pyridin-2-ylethyl) amino] propyl}-2-[(3,4,5-trimethoxyphenyl)amino]-1H-benzimidazole-5-carboxamide (105 mg, 1 eq. prepared according to Example A1) cooled down to 0° C., in tetrahydrofuran (3 ml). After stirring for 15 minutes at 0° C., the mixture is heated at 60° C. for 3 hours then cooled down to 0° C. and hydrolysed.

After adding ethyl acetate, decanting and extraction, the combined organic phases are washed with salt water, followed by drying over sodium sulphate and concentrating under reduced pressure. Purification by flash chromatography on silica gel (eluent: 100% dichloromethane to dichloromethane/methanol 9:1) produces the expected compound in the form of a foam (63 mg, 62% yield).

MS/LC: MW calculated=616.8; m/z=617.4 (MH+)

NMR ($^1$H, 400 MHz, DMSO-d$_6$): δ 0.81 (d, 12H), 1.77 (m, 2H), 1.86 (m, 2H), 2.06 (d, 4H), 2.24 (s, 3H), 2.49 (t, 2H, $^3$J=6 Hz), 2.74 (t, 2H, $^3$J=7 Hz), 2.91 (t, 2H, $^3$J=7 Hz), 3.48 (s, 2H), 3.62 (s, 3H), 3.78 (s, 6H), 4.05 (m, 2H), 6.97 (d, 1H), 7.13-7.24 (m, 5H), 7.63 (m, 1H), 8.43 (d, 1H), 8.94 (s, 1H).

F. Preparation According to Reaction Diagram F:

The compounds of formula I according to the invention in which Y represents —S— and —NH— and A represents —CH$_2$—, can be prepared according to the following Diagram F:

roform at a temperature of 20-70° C. for 2 to 72 hours in order to produce derivative (21). Alternatively, derivative (4) can be treated with an isothiocyanate in an inert solvent such as tetrahydrofuran, methylene chloride or chloroform, then the resulting thiourea can be treated with methyl iodide in a polar solvent such as ethanol for 3 to 24 hours at a temperature of 20-70° C. in order to produce (21).

As also described in reaction diagram B and Example B1, the dianiline (20) can be treated with thiocarbonyldiimidazole (TCD) or thiophosgene in an inert organic solvent such as tetrahydrofuran, methylene chloride or chloroform at ambient temperature for 2 to 17 hours in order to produce derivative (22). Compound (22) is then alkylated by reacting with a halogenated derivative such as an alkyl or benzyl iodide, bromide or chloride or a bromoketone, in the presence of a tertiary base such as triethylamine or diisopropylethy-

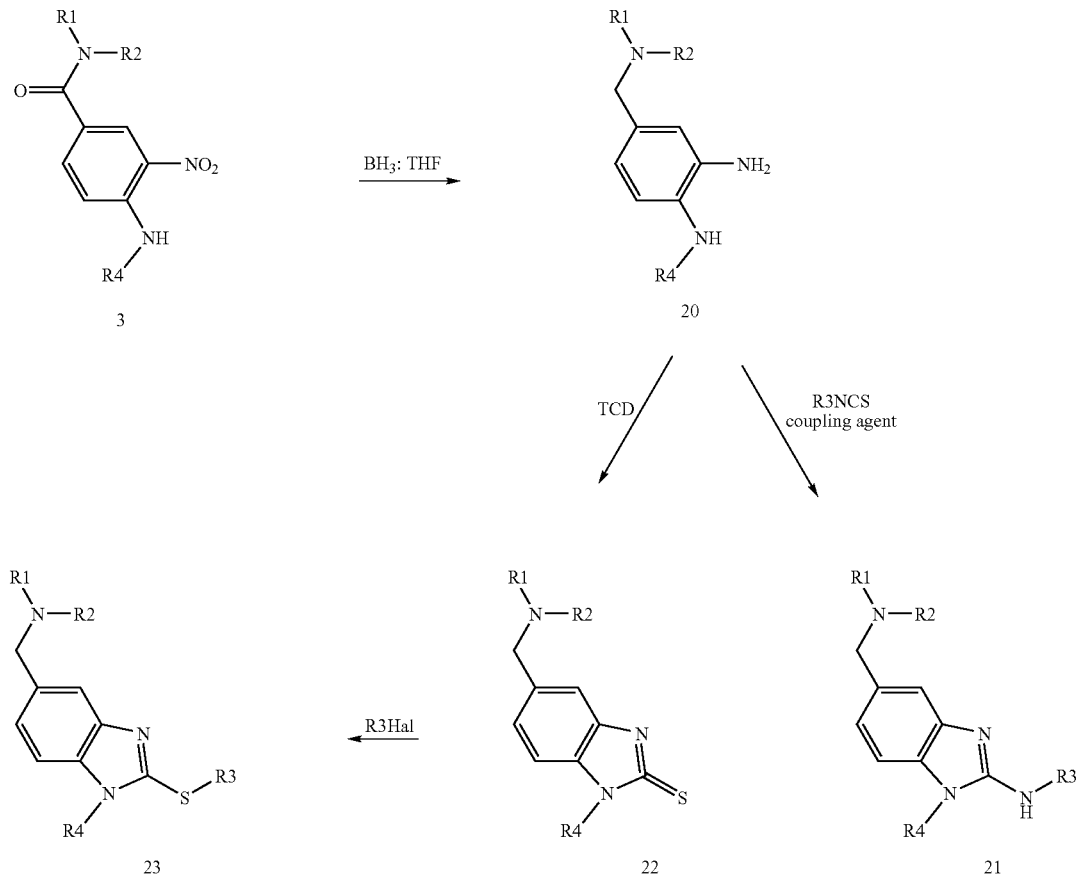

As described in Diagram F, derivative (3) can be reduced to compound (20) using borane in an aprotic solvent such as tetrahydrofuran or diethyl ether at a temperature of 0 to 70° C., for 18 to 24 hours. The dianiline (20) can be then treated with an isothiocyanate in the presence of a resin-supported or non-resin-supported coupling agent such as diisopropylcarbodiimide or dicyclohexylcarbodiimide or N-methylcyclohexylcarbodiimide N-methyl polystyrene resin in an inert solvent such as tetrahydrofuran, methylene chloride, or chloroform, lamine, or in the presence of a resin-supported tertiary base such as morpholinomethyl polystyrene resin, in an inert organic solvent such as tetrahydrofuran, choroform or methylene chloride, at a temperature of 20-70° C. for 3 to 24 hours. The resulting thiobenzimidazole derivative (23) can be isolated, either by flash chromatography on silica gel, or by adding a polymer-supported nucleophilic reagent such as for example an aminomethyl polystyrene resin, and a polymer-supported electrophilic reagent such as for example 4-bromomethylphenoxymethyl polystyrene resin to the reaction mixture, followed by filtration and evaporation of the filtrate.

EXAMPLE F1

5-[(diisobutylamino)methyl]-1-(3-{methyl[2-(2-pyridinyl)ethyl amino}propyl)-N-(3,4,5-trimethoxyphenyl)-1H-benzimidazol-2-amine

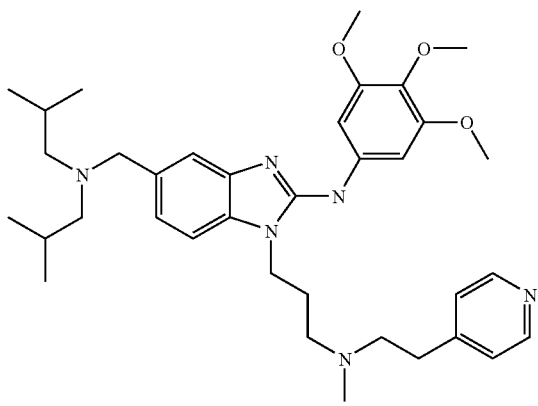

Stage 1: 4-[(diisobutylamino)methyl]-N-(3-{methyl[2-(4-pyridinyl)ethyl]amino}propyl)-1,2-benzenediamine A molar solution of borane-tetrahydrofuran complex (6.25 ml, 15 eq) is added dropwise to a solution of N,N-diisobutyl-4-({3-[methyl(2-pyridin-4-ylethyl)amino]propyl}amino)-3-nitrobenzamide (200 mg, 1 eq) in tetrahydrofuran (3 ml) cooled down to 0° C. The mixture is heated under reflux for 20 hours then cooled down to 0° C. and hydrolysed with a 6N aqueous solution of hydrochloric acid (12 ml). After 1 hour 30 minutes under reflux, the mixture is cooled down to 0° C. and brought to basic pH by a 6N aqueous solution of soda. After adding ethyl acetate, decanting and extracting, the organic phases are combined, followed by washing with salt water, drying over sodium sulphate and evaporating under reduced pressure. Purification by flash chromatography on silica gel (eluent: 100% dichloromethane to dichloromethane/methanol 8:2) produces the expected compound in the form of an oil (92 mg, 51% yield).

MS/LC: MW calculated=425.6; m/z=426.4 (MH+)

NMR ($^1$H, 400 MHz, DMSO-$d_6$): δ 0.83 (d, 12H), 1.72 (m, 4H), 2.03 (d, 4H, $^3$J=7 Hz), 2.23 (s, 3H), 2.48 (t, 2H, $^3$J=7 Hz), 2.60 (t, 2H, $^3$J=7 Hz), 2.75 (t, 2H, $^3$J=7 Hz), 2.96 (m, 2H), 3.38 (s, 2H), 4.30 (m, 3H), 6.30 (d, 1H), 6.42 (d, 1H), 6.51 (s, 1H), 7.25 (d, 1H), 7.45 (m, 1H), 8.41 (m, 2H).

Stage 2: 5-[(diisobutylamino)methyl]-1-(3-{methyl[2-(2-pyridinyl)ethyl]amino}propyl)-N-(3,4,5-trimethoxyphenyl)-1H-benzimidazol-2-amine 3,4,5 trimethoxyphenylisothiocyanate (57 mg, 1.2 eq) and N-methylcyclohexylcarbodiimide-N-methyl polystyrene resin (acquired from Novabiochem; load 1.69 mmol/g, 501 mg, 4 eq) are added successively to a solution of 4-[(diisobutylamino)methyl]-N-(3-{methyl[2-(4-pyridinyl)ethyl]amino}propyl)-1,2-benzenediamine (90 mg, 1 eq) in tetrahydrofuran (2 ml). The mixture is heated under reflux for 18 hours then cooled down to ambient temperature and aminomethyl polystyrene resin (acquired from Novabiochem, 2 eq) is added. After stirring for 4 hours at ambient temperature, the mixture is filtered on frit and the filtrate is concentrated under reduced pressure at 40° C. Purification by flash chromatography on silica gel (eluent: 100% dichloromethane to dichloromethane/methanol 9:1) produces the expected compound in the form of a beige foam (92 mg, 83% yield).

MS/LC: MW calculated=616.8; m/z=617.4 (MH+)

NMR ($^1$H, 400 MHz, DMSO-$d_6$): δ0.81 (d, 12H), 1.77 (m, 2H), 1.86 (m, 2H), 2.06 (d, 4H), 2.22 (s, 3H), 2.31 (t, 2H, $^3$J=6 Hz), 2.55 (t, 2H, $^3$J=7 Hz), 2.71 (t, 2H, $^3$J=7 Hz), 3.49 (s, 2H), 3.68 (s, 3H), 3.77 (s, 6H), 4.11 (m, 2H), 6.99 (d, 1H), 7.13-7.25 (m, 6H), 8.39 (d, 2H), 8.90 (s, 1H).

G. Preparation According to Reaction Diagram G:

The compounds of formula I according to the invention in which A represents —C(O)— and $R_4$ represents —$NW_4W'_4$, can be prepared according to the following Diagram G:

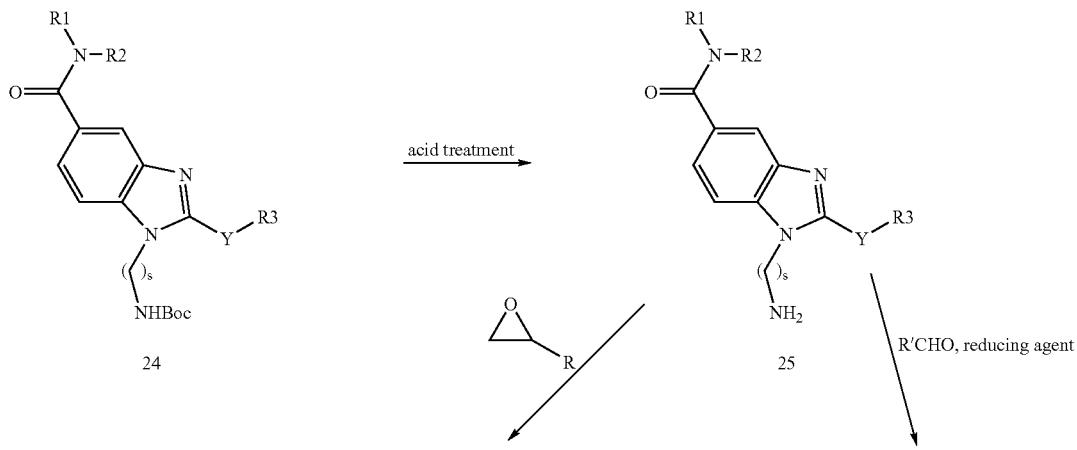

-continued

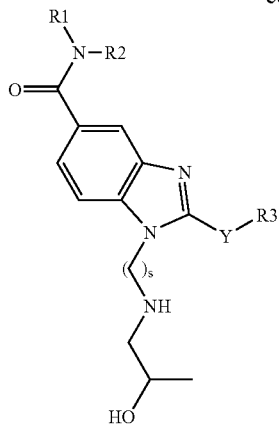

26

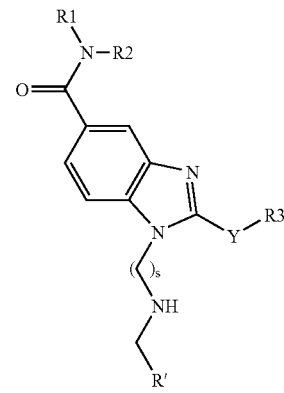

27

As described in Diagram G, the benzimidazole derivative (24), prepared according to reaction diagrams A, B, C or D can be treated with an organic or inorganic acid such as trifluoroacetic acid or hydrogen chloride (aqueous or gaseous form) in an aprotic solvent such as dichloromethane or ethyl acetate at a temperature of 0-20° C. for 0.5 to 5 hours, in order to produce the amine (25). The amine (25) can then be treated with an epoxide in a protic or aprotic polar solvent such as methanol, ethanol or acetonitrile, in the presence or not of lithium perchlorate or ytterbium triflate, at a temperature of 20-80° C. for 4 to 48 hours in order to produce compound (26). The amine (25) can also react with an aldehyde in a protic or aprotic solvent, such as dichloromethane, tetrahydrofuran or methanol, for 1 to 15 hours at a temperature of 0-50° C. The resulting imine is then reduced in situ by a resin-supported or non resin-supported reducing agent, preferably resin-supported sodium triacetoxyborohydride, sodium cyanoborohydride or borohydride, with or without the presence of an acid such as acetic acid, at a temperature of 20 to 50° C. for a duration of 0.2 to 5 hours, in order to produce compound (27).

The compounds 27 for which s=3 can also be prepared according to the following Diagram G':

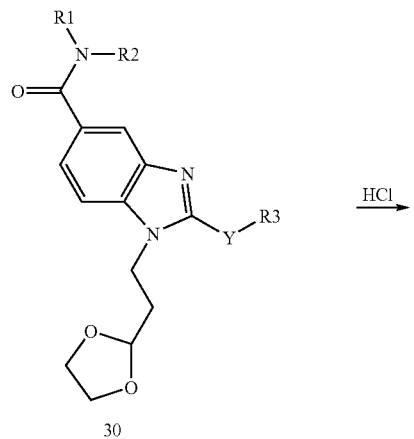

30

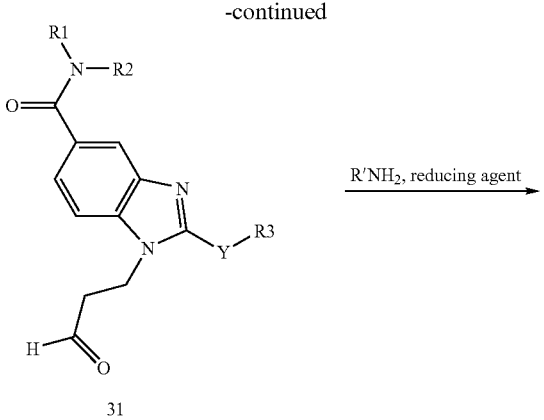

31

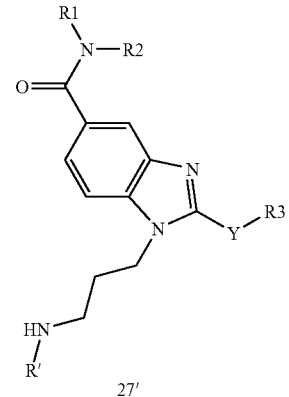

27'

Such as described in Diagram G', the derivative (30) prepared according to reaction Diagrams A, B, C or D can be treated either with an organic acid such as pyridinium tosylate or paratoluenesulphonic acid in an aprotic solvent such as acetone in the presence of water, at a temperature of 20-70° C. for 2 to 12 hours, or with an inorganic acid such as aqueous hydrogen chloride in an aprotic solvent such as tetrahydrofuran at a temperature of 0-20° C. for 6 to 18 hours in order to produce compound (31). The aldehyde (31) can then be treated with an amine in a protic or aprotic solvent such as dichloromethane, tetrahydrofuran or methanol for 1 to 18 hours at a temperature of 20° C. The resulting imine is then reduced in situ by a reducing agent, preferably sodium triacetoxyborohydride or sodium cyanoborohydride, in the presence or not of an acid such as acetic acid, at a temperature of 20-50° C. for a duration of 0.2 to 6 hours, in order to produce compound (27').

EXAMPLE G1

1-{2-[(cyclohexylmethyl)amino]ethyl}-N,N-diisobutyl-2-[(3,4,5-trimethoxyphenyl)amino]-1H-benzimidazole-5-carboxamide

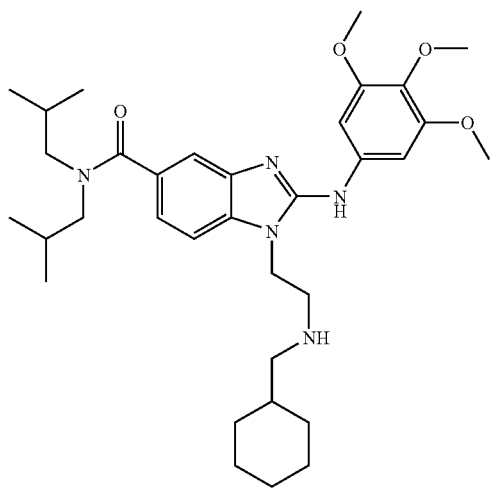

Stage 1: 1-(2-aminoethyl)-N,N-diisobutyl-2-[(3,4,5-trimethoxy phenyl)amino]-1H-benzimidazole-5-carboxamide hydrochloride A stream of dry HCl is passed through a solution of tert-butyl 2-{5-[(diisobutylamino)carbonyl]-2-[(3,4,5-trimethoxy phenyl)amino]-1H-benzimidazol-1-yl}ethylcarbamate (2.56 g, prepared according to the procedure described in Example A1, reaction diagram A) in ethyl acetate (100 ml), (100% ethyl acetate) cooled down to 0° C. until the TLC shows complete disappearance of the starting product. The resulting mixture is then evaporated under reduced pressure. The solid obtained is triturated in diethylether and filtered in order to produce the expected compound in the form of white crystals (2.25 g, 97% yield).

MS/LC: MW calculated=497.6; m/z=498.3 (MH+)

NMR ($^1$H, 400 MHz, DMSO-$d_6$): δ 0.67 (m, 6H), 0.92 (m, 6H), 1.84-2.03 (m, 2H), 3.10-3.17 (m, 4H), 3.38 (m, 2H), 3.71 (s, 3H), 3.81 (s, 6H), 4.76 (m, 2H), 6.93 (s, 2H), 7.30 (m, 2H), 7.81 (d, 1H), 8.56 (m, 3H).

Stage 2: 1-{2-[(cyclohexylmethyl)amino]ethyl}-N,N-diisobutyl-2-[(3,4,5-trimethoxy phenyl)amino]-1H-benzimidazole-5-carboxamide A solution of 1-(2-aminoethyl)-N,N-diisobutyl-2-[(3,4,5-trimethoxyphenyl)amino]-1H-benzimidazole-5-carboxamide (30 mg, 1 eq) and cyclohexanecarboxaldehyde (5 mg, 0.8 eq) in methanol (0.7 ml) is stirred at a temperature of approximately 20° C. for 4 hours. Borohydride resin (48 mg, 2.5 mmol/g, Amberlite (, IRA-400) is added and the mixture is stirred for 18 hours then dichloromethane (0.5 ml) and benzyloxybenzaldehyde Wang resin (37 mg, 3.22 mmol/g, Novabiochem) are added. After stirring overnight, the mixture is filtered and the filtrate is evaporated under reduced pressure in order to produce the expected compound in the form of a beige foam (18 mg, 65%).

MS/LC: MW calculated=593.8; m/z=594.4 (MH+)

NMR ($^1$H, 400 MHz, CDCl$_3$): δ 0.65-1.80 (m, 23H), 2.60 (d, 2H), 3.13 (m, 2H), 3.82 (s, 3H), 3.90 (s, 6H), 4.10 (m, 2H), 6.91 (s, 2H), 7.07; 7.16 (AB, 2H), 7.53 (s, 1H), 10.1 (s, 1H).

The following compounds were prepared according to reaction Diagram G and in a similar manner to the procedure described for the synthesis of 1-{2-[(cyclohexylmethyl)amino]ethyl}-N,N-diisobutyl-2-[(3,4,5-trimethoxyphenyl)amino]-1H-benzimidazole-5-carboxamide (a final purification by flash chromatography on silica gel can also be carried out):

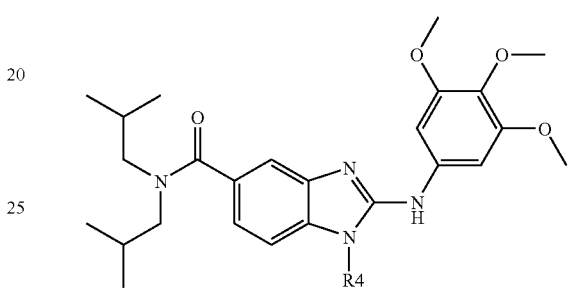

In the above formula, R$_4$ represents one of the radicals below:

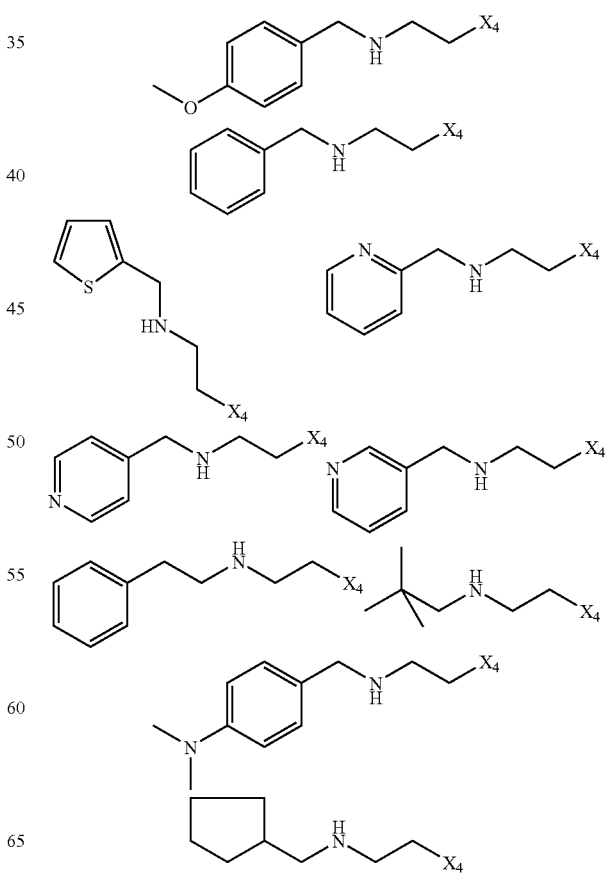

53
-continued
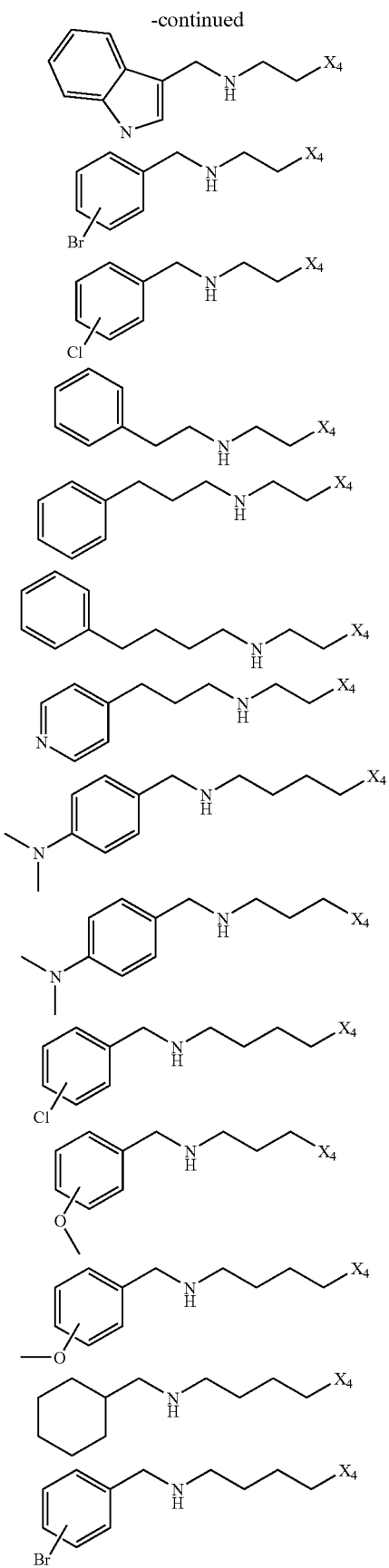
54
-continued
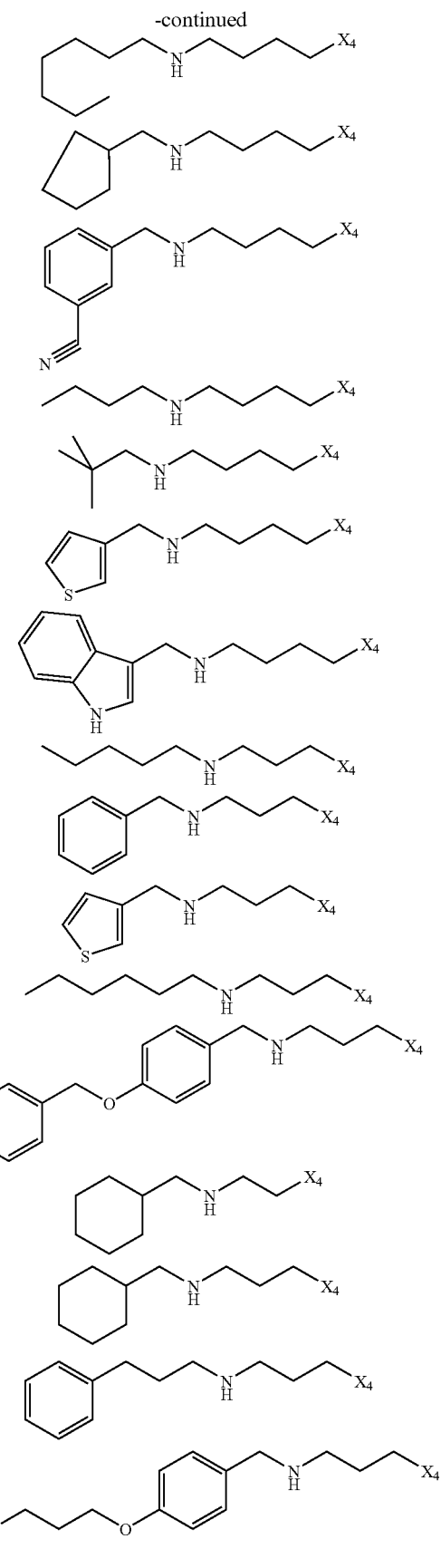

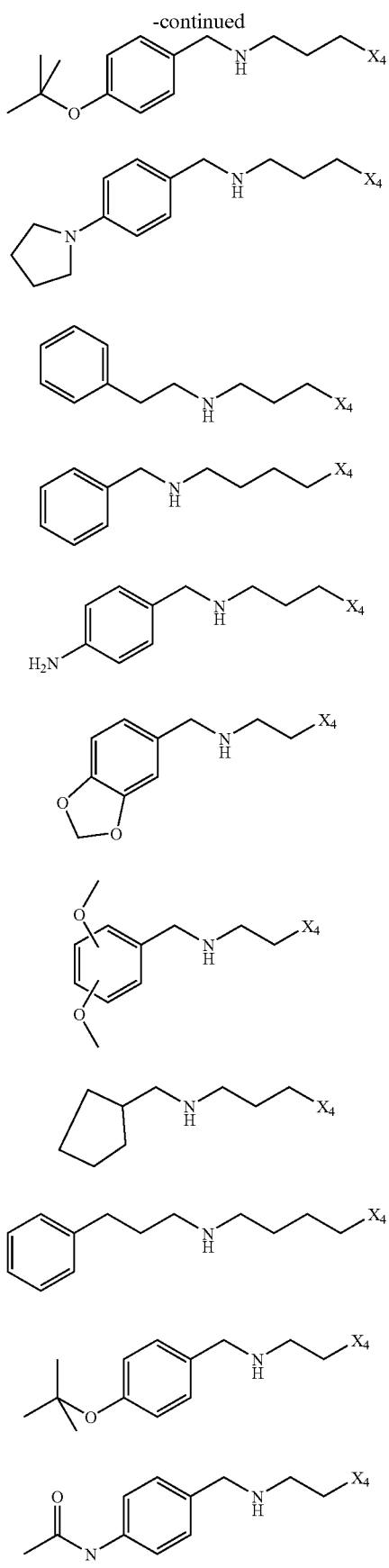
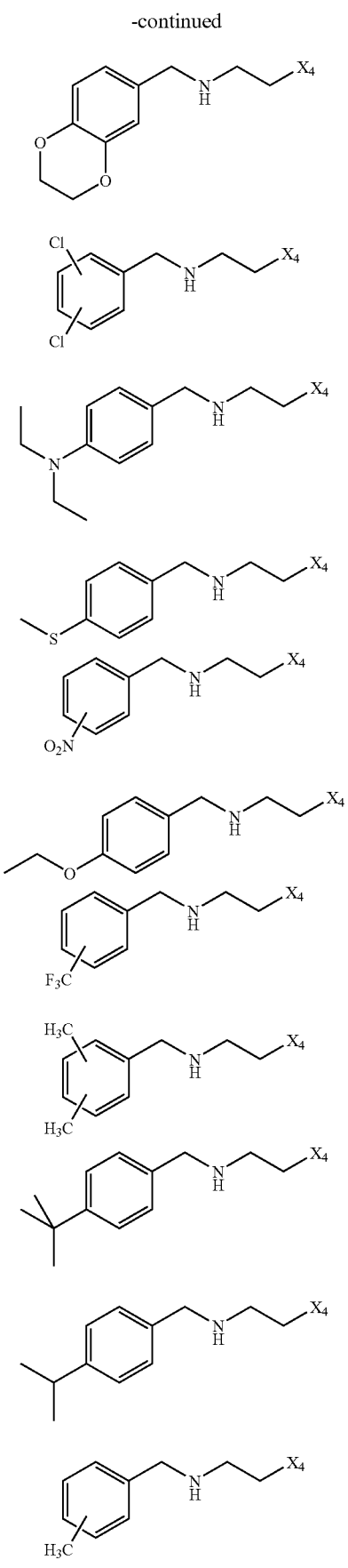

EXAMPLE G2

1-{2-[(1-hydroxy-2-phenylethyl)amino]ethyl}-N,N-diisobutyl-2-[(3,4,5-trimethoxyphenyl)amino]-1H-benzimidazole-5-carboxamide

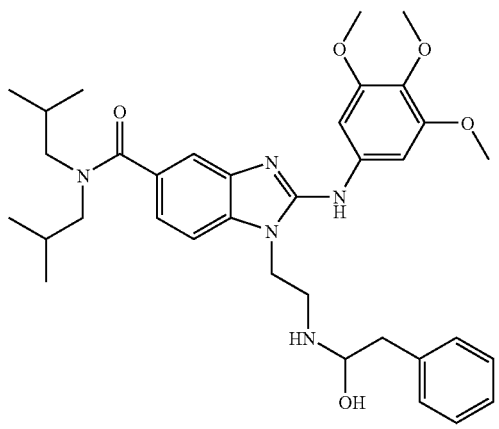

Lithium perchlorate (16 mg, 3 eq) then after 5 minutes 1-(2-aminoethyl)-N,N-diisobutyl-2-[(3,4,5-trimethoxy phenyl)amino]-1H-benzimidazole-5-carboxamide (25 mg, 1 eq) are added, at a temperature of approximately 20° C. to a solution of 2,3-epoxypropylbenzene (7 mg, 1 eq) in acetonitrile (0.5 ml). The mixture is heated under reflux for 24 hours then cooled down to ambient temperature and hydrogen carbonate and dichloromethane saturated water is added. After decanting and extracting, the organic phases are combined and washed with salt water, followed by drying over sodium sulphate and evaporating under reduced pressure at 40° C. Purification of the oil obtained by flash chromatography on silica gel (100% dichloromethane to dichloromethane/methanol 80:20) produces the expected compound in the form of an oil (31 mg, 55% yield)

MS/LC: MW calculated=631.8; m/z=632.4 (MH+)

NMR ($^1$H, 400 MHz, DMSO-$d_6$): δ 0.83 (m, 6H), 0.91 (m, 6H), 1.81-2.10 (m, 2H), 2.57-2.65 (m, 3H), 2.91 (m, 2H), 3.21 (m, 4H), 3.62 (s, 3H), 3.75 (m, 7H), 4.22 (m, 2H), 4.74 (d, 1H), 6.97-7.33 (m, 10H).

The following compounds were prepared according to reaction diagram G and in a similar manner to the procedure described for the synthesis of 1-{2-[(1-hydroxy-2-phenylethyl)amino]ethyl}-N,N-diisobutyl-2-[(3,4,5-trimethoxyphenyl)amino]-1H-benzimidazole-5-carboxamide:

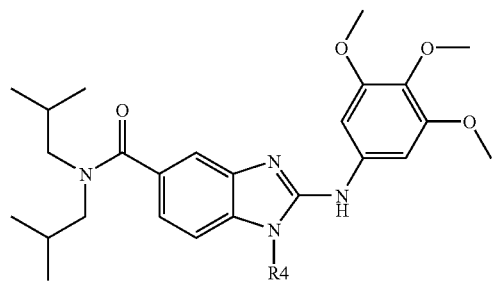

In the above formula, $R_4$ represents one of the radicals below:

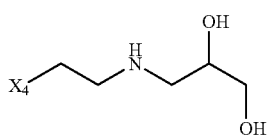

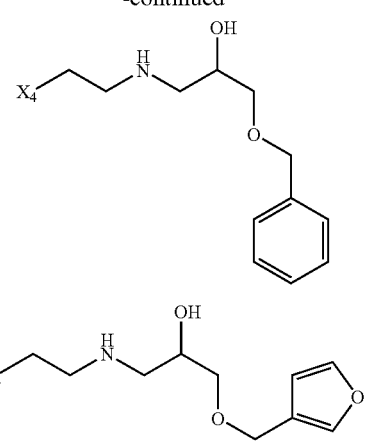

H. Preparation According to Reaction Diagram H:

The compounds of formula I according to the invention in which A represents —C(O)—, Y represents —S— and $R_3$ represents —$(CH_2)_p$—CH(OH)—$(CH_2)_{p'}$-$Z_3$, can be prepared according to the following diagram H:

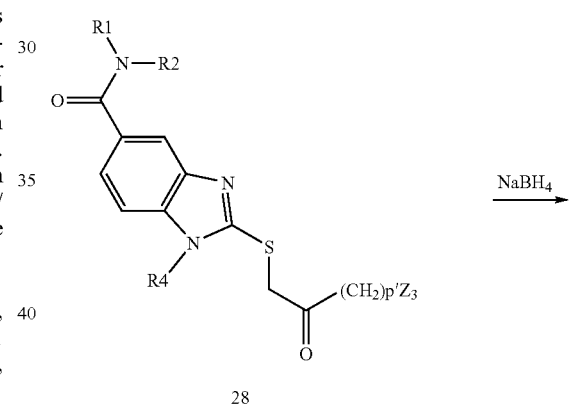

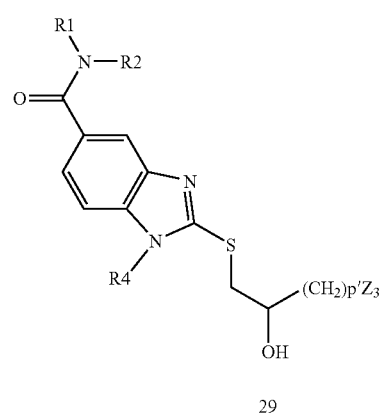

As described in Diagram H, the thiobenzimidazole derivative (28), prepared according to reaction diagrams B or D, can be treated with a reducing agent such as sodium borohydride in a protic solvent such as methanol at a temperature of 0-20° C. for 0.2 hours to 1 hour, in order to produce the corresponding alcohol (29).

EXAMPLE H1

2-{[2-hydroxy-2-(3,4,5-trimethoxyphenyl)ethyl]thio}-N,N-diisobutyl-1-{3-[methyl(2-pyridin-2-yl-ethyl)amino]propyl}-1H-benzimidazole-5-carboxamide

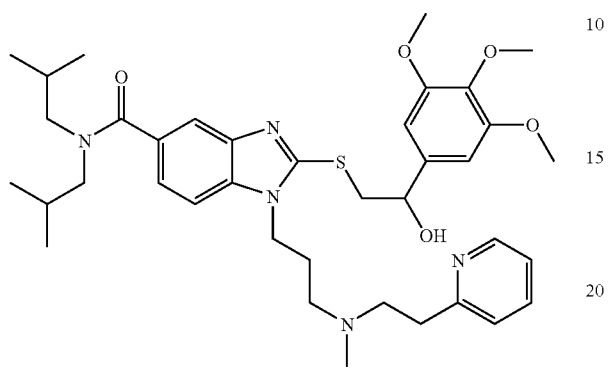

Sodium borohydride (8 mg, 2 eq) is added at 0° C. to a solution of N,N-diisobutyl-1-{3-[methyl(2-pyridin-2-yl-ethyl)amino]propyl}-2-{[2-oxo-2-(3,4,5-trimethoxyphenyl)ethyl]thio}-1H-benzimidazole-5-carboxamide (69 mg, 1 eq) in methanol (2 ml). After stirring for 10 minutes at 0° C., the mixture is taken to a temperature of approximately 20° C. and stirred at this temperature for 30 minutes. The mixture is then concentrated under reduced pressure at 40° C. then water saturated with ammonium chloride and dichloromethane is added. After decanting and extracting, the organic phases are combined and washed with salt water, dried over sodium sulphate and evaporated under reduced pressure at 40° C. Purification of the oil obtained by flash chromatography on silica gel (100% dichloromethane to dichloromethane/methanol 80:20) produces the expected compound in the form of an oil (61 mg, 88% yield).

MS/LC: MW calculated=691.9; m/z=692.4 (MH+)

NMR ($^1$H, 400 MHz, DMSO-$d_6$): δ0.61 (m, 6H), 0.91 (m, 6H), 1.71-2.03 (m, 4H), 2.17 (s, 3H), 2.31 (t, 3H, $^3$J=6.5 Hz), 2.65 (t, 2H, $^3$J=7 Hz), 2.85 (t, 2H, $^3$J=7 Hz), 3.08-3.30 (m, 4H), 3.56 (m, 1H), 3.60 (s, 3H), 3.71 (m, 1H), 3.75 (s, 6H), 4.05 (t, 2H, $^3$J=7 Hz), 4.86 (m, 1H), 5.87 (d, 1H), 6.75 (s, 2H), 7.11-7.65 (m, 6H), 8.43 (d, 1H).

Preparation of the Synthesis Reagents

N-(2-pyridin-2-yl ethyl)propane-1,3-diamine

Acrylonitrile (10.1 ml, 1.1 eq) is added slowly to a solution cooled down to approximately 4° C. of 2-[2-(methylamino)ethyl]pyridine (19.5 ml, 1 eq) in methanol (200 ml). The reaction medium is then stirred for 3 hours at approximately 20° C. then concentrated under reduced pressure at 40° C. in order to produce 3-[(2-pyridin-2-ylethyl)amino]propanenitrile in the form of a yellow oil (25.6 g, 96% yield).

A solution of this oil (15.3 g) in methanol saturated with ammonia (250 ml) is hydrogenated in the presence of Raney nickel (1.5 g) at approximately 20° C. for 15 hours. The reaction mixture is then filtered on Celite. The filtrate is concentrated under reduced pressure at approximately 40° C. in order to produce the expected compound in the form of a greenish oil (15.5 g, yield 97%).

The following compounds were prepared in a similar manner to the procedure described for the synthesis of N-(2-pyridin-2-ylethyl)propane-1,3-diamine:

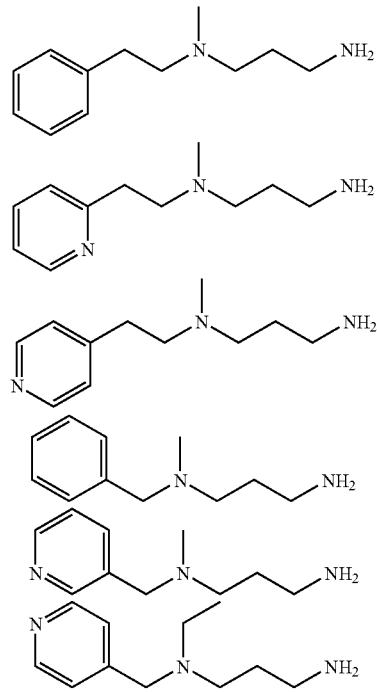

2-bromo-1-(3,4,5-trimethoxyphenyl)ethanone

Resin-supported pyridine hydrobromide perbromide (23, g, 1 eq) is added to a solution of 3,4,5-trimethoxy-acetophenone (10 g, 1 eq) in methanol (150 ml). After stirring for 3 hours at approximately 20° C., the mixture is filtered and the filtrate is concentrated under reduced pressure. Purification of the residue obtained by flash chromatography on silica gel (eluent: heptane/ethyl acetate 8/2 then 7/3) produces the expected compound in the form of a white powder (8.2 g, 60% yield). Melting point=66° C.

3,4,5-trimethoxybenzoyl isothiocyanate

Potassium thiocyanate is added to a solution of 3,4,5-trimethoxybenzoylchloride (2.3 g) in acetonitrile (40 ml). After stirring for 15 minutes at approximately 20° C., the mixture is filtered and the filtrate is concentrated under reduced pressure in order to produce the expected compound in the form of a beige powder (2.4 g, 96% yield). Melting point=101° C.

The compounds I (or I') of the present invention have useful pharmacological properties. In this way it was discovered that the compounds I (or I') of the present invention have an antagonist activity of GnRH (Gonadotropin-Releasing hormone).

The compounds of the present invention can thus be used in different therapeutic applications. They can advantageously be used in women in the treatment of endometriosis, fibroma, polycystic ovary syndrome, cancer of the breast, the ovary and the endometrium, gonadotropic hypophyseal desensitization during medically-assisted procreation protocols; in men, in the treatment of benign prostatic hyperplasia and prostate cancer; and in the treatment of male or female precocious puberty. An illustration of the pharmacological properties of the compounds of the invention will be found below, in the experimental part.

A subject of the invention is also, as medicaments, the products of formula I (or I') as defined above, as well as the addition salts with pharmaceutically acceptable mineral or organic acids of said products of formula I (or I'), as well as the pharmaceutical compositions containing, as active ingredient, at least one of the medicaments as defined above, in combination with a pharmaceutically acceptable support.

The pharmaceutical composition can be in the form of a solid, for example powders, granules, tablets, gelatin capsules or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound according to the invention can also be presented in liquid form, for example solutions, emulsions, suspensions or syrups. Appropriate liquid supports can be, for example, water, organic solvents such as glycerol or glycols, similarly their mixtures, in varying proportions, in water with added pharmaceutically acceptable oils or fats. The sterile liquid compositions can be used for intramuscular, intraperitoneal or subcutaneous injections and the sterile compositions can also be administered intravenously.

All the technical and scientific terms used in the present text have the meanings known to a person skilled in the art. Moreover, all patents (or patent applications) as well as other bibliographical references are incorporated by way of reference.

Experimental Part:

The compounds according to the invention, obtained according to the procedures of Examples A, B, C, D, E, F, G and H described previously, are set out in the table below.

The compounds are characterised by their retention time (rt) and their molecular peak determined by mass spectrometry (MH+).

For the mass spectrometry, a single quadripole mass spectrometer (Micromass, Platform model) equipped with an electrospray source is used with a resolution of 0.8 Da at 50% valley. Calibration is carried out monthly between masses 80 and 1000 Da using a calibration mixture of sodium iodide and rubidium iodide in solution in an isopropanol/water mixture (1/1 Vol.).

For the liquid chromatography, a Waters system including an in-line degasser, a Waters 600 quaternary pump, a Gilson 233 plate sampling injector and a Waters 996 PDA UV detector, are used.

The elution conditions used are the following:
Eluent A water+0.04% trifluoroacetic acid
B acetonitrile

| T (min) | A % | B % |
|---|---|---|
| 1 | 95 | 5 |
| 8.5 | 5 | 95 |
| 10.5 | 5 | 95 |
| 10.6 | 95 | 5 |
| 14.9 | 95 | 5 |
| 15.0 | 95 | 5 |

Flow rate: 1 ml/min
Injection: 10 μL
Column: Uptisphere ODS 3 μm 75*4.6 mm i.d

These examples are presented in order to illustrate the above procedures and should in no case be considered as limiting the scope of the invention.

In each illustration of the $R_1$, $R_2$, $R_3$ and $R_4$ radicals, the $X_1$, $X_2$, $X_3$ and $X_4$ radicals represent, respectively, the remaining part of the compound of general formula (I).

Examples 1 to 253, 254 to 255 and 256 to 538 illustrate respectively compounds I in which A represents —C(O)— and Y—S—, A represents —CH$_2$— and Y—NH— and A represents —C(O)— and Y—NH—.

| Examples | R1 | R2 | R3 | R4 | [M + H]⁺ | rt (min) |
|---|---|---|---|---|---|---|
| 1 | (CH₃)₂CHCH₂-X₁ | X₂-CH₂CH(CH₃)- | 3,5-dimethylbenzyl-X₃ | X₄-(CH₂)₄-N(CH₃)-CH₂CH₂-Ph | 599.4 | 9.7 |
| 2 | (CH₃)₂CHCH₂-X₁ | (CH₃)CH(X₂)CH₂- | 3,5-bis(trifluoromethyl)phenacyl-X₃ | X₄-(CH₂)₄-N(CH₃)-CH₂CH₂-Ph | 735.3 | 10.7 |
| 3 | (CH₃)₂CHCH₂-X₁ | X₂-CH₂CH(CH₃)- | 3,5-dimethylbenzyl-X₃ | X₄-(CH₂)₄-N(CH₃)-CH₂CH₂-(2-pyridyl) | 600.4 | 9.3 |
| 4 | (CH₃)₂CH(X₁)CH₂- | X₂-CH₂CH(CH₃)- | phenacyl-X₃ | X₄-(CH₂)₄-N(CH₃)-CH₂CH₂-Ph | 599.5 | 9.1 |

-continued

| Examples | R1 | R2 | R3 | R4 | [M + H]⁺ | rt (min) |
|---|---|---|---|---|---|---|
| 5 | CH₃CH(CH₃)CH₂-X₁ | X₂CH₂CH(CH₃)CH₃ | (CH₃)₃C-C(=O)-CH₂-X₃ | X₄-(CH₂)₃-N(CH₃)-CH₂CH₂-Ph | 579.5 | 9.2 |
| 6 | CH₃CH(CH₃)CH₂-X₁ | X₂CH₂CH(CH₃)CH₃ | 3-NO₂-C₆H₄-C(=O)-CH₂-X₃ | X₄-(CH₂)₃-N(CH₃)-CH₂CH₂-Ph | 644.5 | 9.1 |
| 7 | CH₃CH(CH₃)CH₂-X₁ | X₂CH₂CH(CH₃)CH₃ | 2-naphthyl-C(=O)-CH₂-X₃ | X₄-(CH₂)₃-N(CH₃)-CH₂CH₂-Ph | 649.5 | 9.7 |
| 8 | CH₃CH(CH₃)CH₂-X₁ | X₂CH₂CH(CH₃)CH₃ | 2,5-(CH₃O)₂-C₆H₃-C(=O)-CH₂-X₃ | X₄-(CH₂)₃-N(CH₃)-CH₂CH₂-Ph | 659.5 | 9.2 |

-continued

| Examples | R1 | R2 | R3 | R4 | [M + H]⁺ | rt (min) |
|---|---|---|---|---|---|---|
| 9 | (CH₃)₂CH-CH₂-X₁ | (CH₃)₂CH-CH₂-X₂ | 3,4-dichlorophenyl-C(O)-CH₂-X₃ | X₄-(CH₂)₄-N(CH₃)-CH₂-CH₂-phenyl | 667.4 | 9.8 |
| 10 | (CH₃)₂CH-CH₂-X₁ | (CH₃)₂CH-CH₂-X₂ | 4-(N,N-diethylamino)phenyl-C(O)-CH₂-X₃ | X₄-(CH₂)₄-N(CH₃)-CH₂-CH₂-phenyl | 670.5 | 9.7 |
| 11 | (CH₃)₂CH-CH₂-X₁ | (CH₃)₂CH-CH₂-X₂ | 4-azidophenyl-C(O)-CH₂-X₃ | X₄-(CH₂)₄-N(CH₃)-CH₂-CH₂-phenyl | 640.5 | 9.4 |
| 12 | (CH₃)₂CH-CH₂-X₁ | (CH₃)₂CH-CH₂-X₂ | 2,3-dihydro-1,4-benzodioxin-6-yl-C(O)-CH₂-X₃ | X₄-(CH₂)₄-N(CH₃)-CH₂-CH₂-phenyl | 657.5 | 8.9 |

-continued

| Examples | R1 | R2 | R3 | R4 | [M + H]⁺ | rt (min) |
|---|---|---|---|---|---|---|
| 13 | CH₃CH(CH₃)CH₂-X₁ (isobutyl) | X₂-CH₂-CH(CH₃)-CH₃ (isobutyl) | 3-bromophenyl-C(=O)-CH₂-X₃ | X₄-(CH₂)₃-N(CH₃)-CH₂CH₂-phenyl | 677.4 | 9.4 |
| 14 | CH₃CH(CH₃)CH₂-X₁ | X₂-CH₂-CH(CH₃)-CH₃ | 2,4-dimethylphenyl-C(=O)-CH₂-X₃ | X₄-(CH₂)₃-N(CH₃)-CH₂CH₂-phenyl | 627.5 | 9.6 |
| 15 | CH₃CH(CH₃)CH₂-X₁ | X₂-CH₂-CH(CH₃)-CH₃ | 2-(trifluoromethyl)phenyl-CH₂-C(=O)-CH₂-X₃ | X₄-(CH₂)₃-N(CH₃)-CH₂CH₂-phenyl | 681.5 | 9.5 |
| 16 | H | 4-(N,N-diethylamino)phenyl-X₂ | phenyl-C(=O)-CH₂-X₃ | X₄-(CH₂)₃-N(CH₃)-CH₂CH₂-phenyl | 634.5 | 7.2 |

-continued
| Examples | R1 | R2 | R3 | R4 | [M + H]⁺ | rt (min) |
|---|---|---|---|---|---|---|
| 17 | H |  | 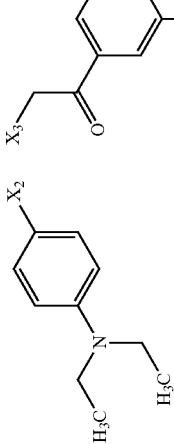 | 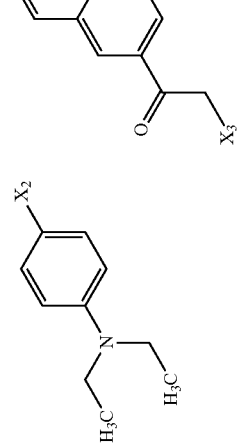 | 614.5 | 7.2 |
| 18 | H |  | 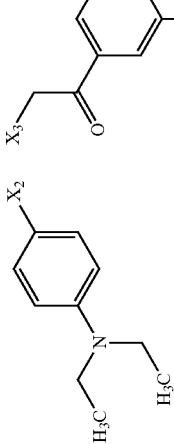 | 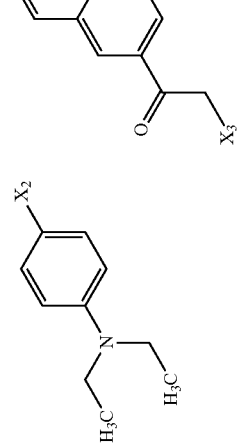 | 679.5 | 7.3 |
| 19 | H |  | 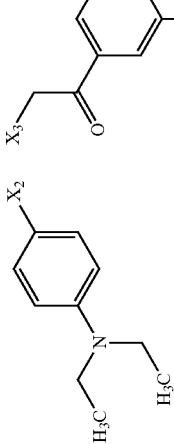 | 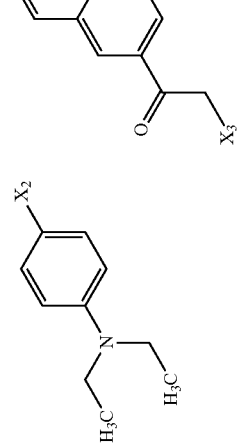 | 684.5 | 7.7 |
| 20 | H |  | 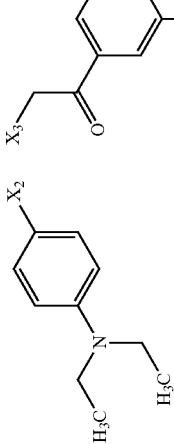 | 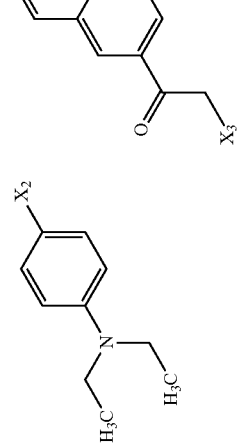 | 694.5 | 7.3 |

-continued
| Examples | R1 | R2 | R3 | R4 | [M + H]+ | rt (min) |
|---|---|---|---|---|---|---|
| 21 | H | | | | 702.4 | 7.7 |
| 22 | H | | | | 705.5 | 7.6 |
| 23 | H | | | | 673.5 | 7.3 |
| 24 | H | | | | 692.5 | 7.3 |
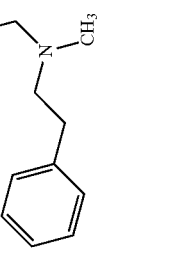

-continued
| Examples | R1 | R2 | R3 | R4 | [M + H]+ | rt (min) |
|---|---|---|---|---|---|---|
| 25 | H | 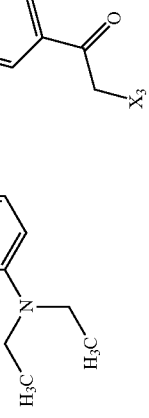 | 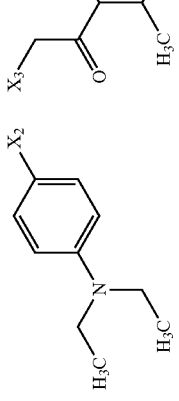 | 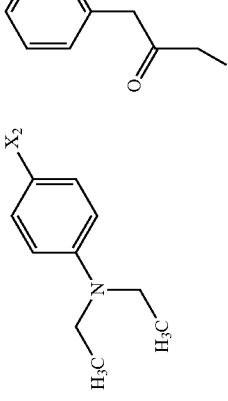 | 712.4 | 7.5 |
| 26 | H | 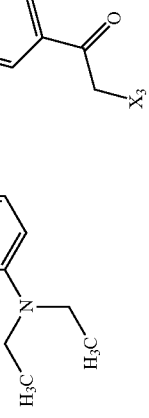 | 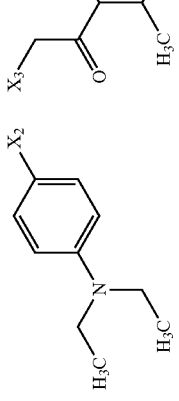 | 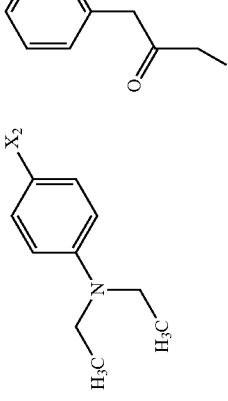 | 662.5 | 7.6 |
| 27 | H | 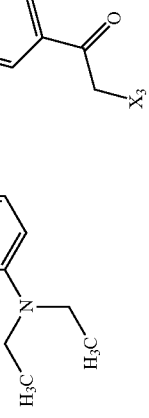 | 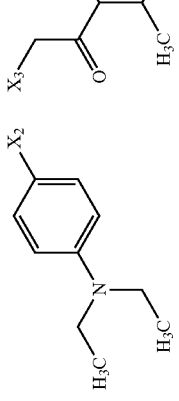 | 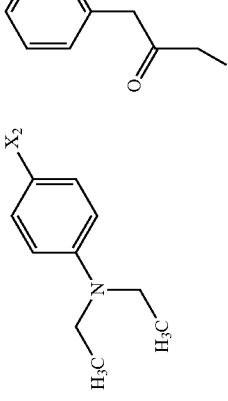 | 716.22 | 7.4 |
| 28 | 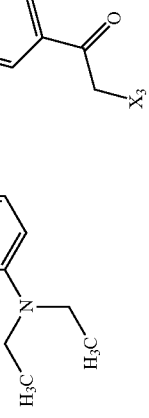 | 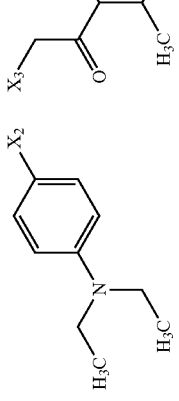 | 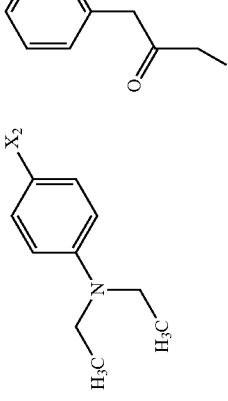 | | 600.5 | 8.5 |

-continued

| Examples | R1 | R2 | R3 | R4 | [M + H]⁺ | rt (min) |
|---|---|---|---|---|---|---|
| 29 | (CH₃)₂CHCH₂–X₁ | (CH₃)₂CHCH₂–X₂ | (CH₃)₃C-C(O)-CH₂–X₃ | X₄-(CH₂)₄-N(CH₃)-CH₂CH₂-(2-pyridyl) | 580.5 | 8.5 |
| 30 | (CH₃)₂CHCH₂–X₁ | (CH₃)₂CHCH₂–X₂ | 3-nitrophenyl-C(O)-CH₂–X₃ | X₄-(CH₂)₄-N(CH₃)-CH₂CH₂-(2-pyridyl) | 645.5 | 8.5 |
| 31 | (CH₃)₂CHCH₂–X₁ | (CH₃)₂CHCH₂–X₂ | 2-naphthyl-C(O)-CH₂–X₃ | X₄-(CH₂)₄-N(CH₃)-CH₂CH₂-(2-pyridyl) | 650.5 | 9.1 |
| 32 | (CH₃)₂CHCH₂–X₁ | (CH₃)₂CHCH₂–X₂ | 2,5-dimethoxyphenyl-C(O)-CH₂–X₃ | X₄-(CH₂)₄-N(CH₃)-CH₂CH₂-(2-pyridyl) | 660.6 | 8.5 |

-continued

| Examples | R1 | R2 | R3 | R4 | [M+H]+ | rt (min) |
|---|---|---|---|---|---|---|
| 33 | (CH3)2CHCH2-X1 | X2-CH2CH(CH3)2 | 3,4-dichlorophenyl-C(O)-CH2-X3 | X4-(CH2)3-N(CH3)-CH2CH2-(2-pyridyl) | 668.5 | 9.2 |
| 34 | (CH3)2CHCH2-X1 | X2-CH2CH(CH3)2 | 4-(N,N-diethylamino)phenyl-C(O)-CH2-X3 | X4-(CH2)3-N(CH3)-CH2CH2-(2-pyridyl) | 671.2 | 9.0 |
| 35 | (CH3)2CHCH2-X1 | X2-CH2CH(CH3)2 | 4-azidophenyl-C(O)-CH2-X3 | X4-(CH2)3-N(CH3)-CH2CH2-(2-pyridyl) | 641.3 | 8.7 |
| 36 | (CH3)2CHCH2-X1 | X2-CH2CH(CH3)2 | 2,3-dihydrobenzo[1,4]dioxin-6-yl-C(O)-CH2-X3 | X4-(CH2)3-N(CH3)-CH2CH2-(2-pyridyl) | 658.5 | 8.4 |

| Examples | R1 | R2 | R3 | R4 | [M + H]⁺ | rt (min) |
|---|---|---|---|---|---|---|
| 37 | (CH₃)₂CHCH₂-X₁ | X₂-CH₂CH(CH₃)₂ | 3-bromophenyl-C(=O)-CH₂-X₃ | X₄-(CH₂)₃-N(CH₃)-CH₂CH₂-(2-pyridyl) | 678.4 | 8.9 |
| 38 | (CH₃)₂CHCH₂-X₁ | X₂-CH₂CH(CH₃)₂ | X₃-CH₂-C(=O)-(2,4-dimethylphenyl) | X₄-(CH₂)₃-N(CH₃)-CH₂CH₂-(2-pyridyl) | 628.5 | 8.9 |
| 39 | (CH₃)₂CHCH₂-X₁ | X₂-CH₂CH(CH₃)₂ | 2-(trifluoromethyl)phenyl-CH₂-C(=O)-CH₂-X₃ | X₄-(CH₂)₃-N(CH₃)-CH₂CH₂-(2-pyridyl) | 682.5 | 8.9 |
| 40 | (CH₃)₂CHCH₂-X₁ | X₂-CH₂CH(CH₃)₂ | 2,6-dichlorophenyl-CH₂-X₃ | X₄-(CH₂)₃-N(CH₃)-CH₂CH₂-phenyl | 639.4 | 9.6 |

-continued

| Examples | R1 | R2 | R3 | R4 | [M + H]⁺ | rt (min) |
|---|---|---|---|---|---|---|
| 41 | (CH₃)₂CHCH₂-X₁ | X₂-CH₂CH(CH₃)₂ | benzyl-X₃ | X₄-(CH₂)₄-N(CH₃)-CH₂CH₂-Ph | 571.5 | 9.1 |
| 42 | (CH₃)₂CHCH₂-X₁ | X₂-CH₂CH(CH₃)₂ | 4-(C(CH₃)₃)-benzyl-X₃ | X₄-(CH₂)₄-N(CH₃)-CH₂CH₂-Ph | 627.5 | 10.2 |
| 43 | (CH₃)₂CHCH₂-X₁ | X₂-CH₂CH(CH₃)₂ | 3-Br-benzyl-X₃ | X₄-(CH₂)₄-N(CH₃)-CH₂CH₂-Ph | 649.4 | 9.6 |
| 44 | (CH₃)₂CHCH₂-X₁ | X₂-CH₂CH(CH₃)₂ | 4-CH₃-benzyl-X₃ | X₄-(CH₂)₄-N(CH₃)-CH₂CH₂-Ph | 607.5 | 9.5 |

-continued

| Examples | R1 | R2 | R3 | R4 | [M + H]⁺ | rt (min) |
|---|---|---|---|---|---|---|
| 45 | (isobutyl with X₁) | (isobutyl with X₂) | naphthylmethyl-X₃ | phenethyl-N(CH₃)-propyl-X₄ | 621.5 | 9.6 |
| 46 | (isobutyl with X₁) | (isobutyl with X₂) | 2-methoxy-5-nitrobenzyl-X₃ | phenethyl-N(CH₃)-propyl-X₄ | 646.5 | 9.2 |
| 47 | (isobutyl with X₁) | (isobutyl with X₂) | 4-(phenacyloxycarbonylmethyl)benzyl-X₃ | phenethyl-N(CH₃)-propyl-X₄ | 747.5 | 9.5 |
| 48 | (isobutyl with X₁) | (isobutyl with X₂) | 4-bromobenzyl-X₃ | phenethyl-N(CH₃)-propyl-X₄ | 649.4 | 9.6 |

-continued

| Examples | R1 | R2 | R3 | R4 | [M + H]+ | rt (min) |
|---|---|---|---|---|---|---|
| 49 | isobutyl-X1 | isobutyl-X2 | 3-(methoxycarbonyl)benzyl-X3 | X4-(CH2)3-N(CH3)-CH2CH2-phenyl | 629.5 | 9.1 |
| 50 | isobutyl-X1 | isobutyl-X2 | 4-cyanobenzyl-X3 | X4-(CH2)3-N(CH3)-CH2CH2-phenyl | 596.4 | 8.9 |
| 51 | isobutyl-X1 | isobutyl-X2 | 3-chlorobenzyl-X3 | X4-(CH2)3-N(CH3)-CH2CH2-phenyl | 605.4 | 9.5 |
| 52 | isobutyl-X1 | isobutyl-X2 | 3,5-dimethoxybenzyl-X3 | X4-(CH2)3-N(CH3)-CH2CH2-phenyl | 631.5 | 9.2 |

| Examples | R1 | R2 | R3 | R4 | [M + H]⁺ | rt (min) |
|---|---|---|---|---|---|---|
| 53 | H | 4-X₂-C₆H₄-N(CH₃)(CH₂CH₃)(CH₂CH₃) | 2,6-dichlorobenzyl-X₃ | PhCH₂CH₂N(CH₃)(CH₂CH₂CH₂-X₄) | 674.3 | 7.5 |
| 54 | H | 4-X₂-C₆H₄-N(CH₃)(CH₂CH₃)(CH₂CH₃) | benzyl-X₃ | PhCH₂CH₂N(CH₃)(CH₂CH₂CH₂-X₄) | 606.4 | 7.3 |
| 55 | H | 4-X₂-C₆H₄-N(CH₃)(CH₂CH₃)(CH₂CH₃) | 4-tert-butylbenzyl-X₃ | PhCH₂CH₂N(CH₃)(CH₂CH₂CH₂CH₂-X₄) | 662.5 | 8.0 |
| 56 | H | 4-X₂-C₆H₄-N(CH₃)(CH₂CH₃)(CH₂CH₃) | 3-bromobenzyl-X₃ | PhCH₂CH₂N(CH₃)(CH₂CH₂CH₂CH₂-X₄) | 684.3 | 7.5 |

-continued

| Examples | R1 | R2 | R3 | R4 | [M + H]⁺ | rt (min) |
|---|---|---|---|---|---|---|
| 57 | H | (4-X₂-phenyl)-N(CH₃)(CH₂CH₃) | 4-methylbenzyl-X₃ | X₄-(CH₂)₃-N(CH₃)-CH₂CH₂-phenyl | 620.4 | 7.4 |
| 58 | H | N(CH₂CH₃)(CH₃)-phenyl-X₂ | naphthalen-2-ylmethyl-X₃ | X₄-(CH₂)₃-N(CH₃)-CH₂CH₂-phenyl | 656.4 | 7.6 |
| 59 | H | (4-X₂-phenyl)-N(CH₃)(CH₂CH₃) | 2-methoxy-5-nitrobenzyl-X₃ | X₄-(CH₂)₃-N(CH₃)-CH₂CH₂-phenyl | 681.4 | 7.4 |
| 60 | H | (4-X₂-phenyl)-N(CH₃)(CH₂CH₃) | 4-(phenacyloxycarbonylmethyl)benzyl-X₃ | X₄-(CH₂)₃-N(CH₃)-CH₂CH₂-phenyl | 781.3 | 7.7 |

-continued
| Examples | R1 | R2 | R3 | R4 | [M + H]+ | rt (min) |
|---|---|---|---|---|---|---|
| 61 | H | 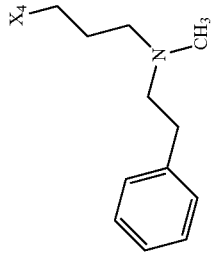 | 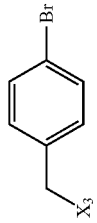 4-Br benzyl | 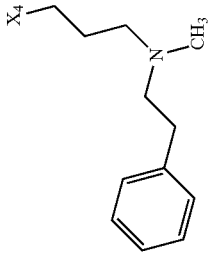 | 684.3 | 7.5 |
| 62 | H | 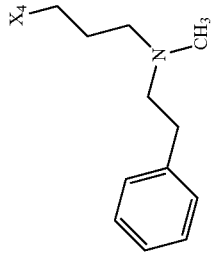 | 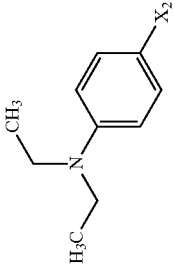 3-CO2CH3 benzyl | 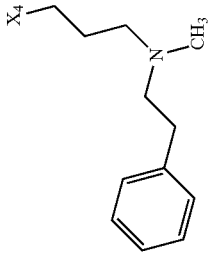 | 664.4 | 7.3 |
| 63 | H | 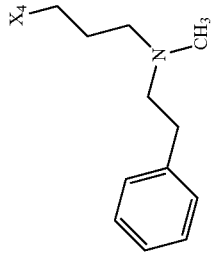 | 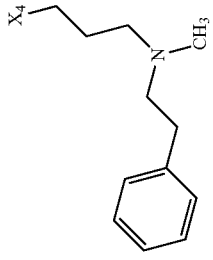 4-CN benzyl | 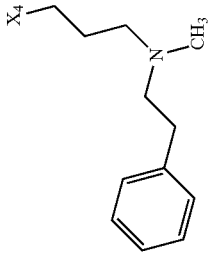 | 631.4 | 7.2 |
| 64 | H | 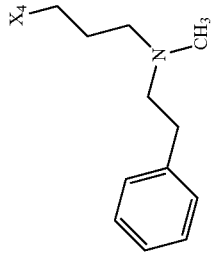 | 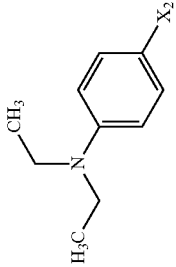 3-Cl benzyl | 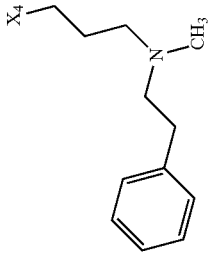 | 640.4 | 7.5 |

-continued

| Examples | R1 | R2 | R3 | R4 | [M + H]⁺ | rt (min) |
|---|---|---|---|---|---|---|
| 65 | H | 4-(N,N-bis(2-methyl)ethylamino)phenyl (N(CH₂CH₃)₂ on phenyl-X₂) | 3,5-dimethoxybenzyl-X₃ | phenethyl-N(CH₃)-(CH₂)₃-X₄ | 666.4 | 7.3 |
| 66 | isobutyl-X₁ | isobutyl-X₂ | 2,6-dichlorobenzyl-X₃ | 2-(pyridin-2-yl)ethyl-N(CH₃)-(CH₂)₃-X₄ | 640.4 | 9.1 |
| 67 | isobutyl-X₁ | isobutyl-X₂ | benzyl-X₃ | 2-(pyridin-2-yl)ethyl-N(CH₃)-(CH₂)₃-X₄ | 572.4 | 8.5 |
| 68 | isobutyl-X₁ | isobutyl-X₂ | 4-tert-butylbenzyl-X₃ | 2-(pyridin-2-yl)ethyl-N(CH₃)-(CH₂)₃-X₄ | 628.5 | 9.7 |

-continued

| Examples | R1 | R2 | R3 | R4 | [M + H]⁺ | rt (min) |
|---|---|---|---|---|---|---|
| 69 | H₃C-CH(CH₃)-CH₂-X₁ | X₂-CH₂-CH(CH₃)-CH₃ | 3-Br-C₆H₄-CH₂-X₃ | X₄-(CH₂)₄-N(CH₃)-CH₂CH₂-(2-pyridyl) | 650.4 | 9.0 |
| 70 | H₃C-CH(CH₃)-CH₂-X₁ | X₂-CH₂-CH(CH₃)-CH₃ | 4-CH₃-C₆H₄-CH₂-X₃ | X₄-(CH₂)₄-N(CH₃)-CH₂CH₂-(2-pyridyl) | 586.4 | 8.9 |
| 71 | CH₃-CH(CH₃)-CH(CH₃)-X₁ | CH₃-CH(CH₃)-CH₂-X₂ | 2-naphthyl-CH₂-X₃ | X₄-(CH₂)₄-N(CH₃)-CH₂CH₂-(2-pyridyl) | 622.5 | 9.1 |
| 72 | H₃C-CH(CH₃)-CH₂-X₁ | X₂-CH₂-CH(CH₃)-CH₃ | 2-(OCH₃)-5-NO₂-C₆H₃-CH₂-X₃ | X₄-(CH₂)₄-N(CH₃)-CH₂CH₂-(2-pyridyl) | 647.5 | 8.7 |

-continued

| Examples | R1 | R2 | R3 | R4 | [M + H]⁺ | rt (min) |
|---|---|---|---|---|---|---|
| 73 | (CH₃)₂CHCH₂-X₁ | X₂-CH₂CH(CH₃)₂ | phenacyl 4-(X₃-methyl)phenylacetate | X₄-(CH₂)₃-N(CH₃)-CH₂CH₂-(2-pyridyl) | 748.5 | 9.1 |
| 74 | (CH₃)₂CHCH₂-X₁ | X₂-CH₂CH(CH₃)₂ | 4-bromobenzyl-X₃ | X₄-(CH₂)₃-N(CH₃)-CH₂CH₂-(2-pyridyl) | 650.4 | 9.0 |
| 75 | (CH₃)₂CHCH₂-X₁ | X₂-CH₂CH(CH₃)₂ | methyl 3-(X₃-methyl)benzoate | X₄-(CH₂)₃-N(CH₃)-CH₂CH₂-(2-pyridyl) | 630.4 | 8.6 |

| Examples | R1 | R2 | R3 | R4 | [M + H]⁺ | rt (min) |
|---|---|---|---|---|---|---|
| 76 | isobutyl-X₁ | isobutyl-X₂ | 4-cyanobenzyl-X₃ | X₄-(CH₂)₄-N(CH₃)-CH₂CH₂-(2-pyridyl) | 597.4 | 8.4 |
| 77 | isobutyl-X₁ | isobutyl-X₂ | 3-chlorobenzyl-X₃ | X₄-(CH₂)₄-N(CH₃)-CH₂CH₂-(2-pyridyl) | 606.4 | 8.9 |
| 78 | isobutyl-X₁ | isobutyl-X₂ | 3,5-dimethoxybenzyl-X₃ | X₄-(CH₂)₄-N(CH₃)-CH₂CH₂-(2-pyridyl) | 632.5 | 8.6 |
| 79 | X₁-CH₃ | phenethyl-X₂ | 3,5-dimethylbenzyl-X₃ | X₄-(CH₂)₄-N(CH₃)-CH₂CH₂-phenyl | 605.5 | 9.0 |

-continued

| Examples | R1 | R2 | R3 | R4 | [M+H]+ | rt (min) |
|---|---|---|---|---|---|---|
| 80 | H | 4-(4-chlorophenyl)piperazinyl-X2 | 3,5-dimethylbenzyl-X3 | X4-(CH2)3-N(CH3)-CH2CH2-phenyl | 666.5 | 9.5 |
| 81 | H | benzyl-X2 | 3,5-dimethylbenzyl-X3 | X4-(CH2)3-N(CH3)-CH2CH2-phenyl | 577.3 | 8.7 |
| 82 | H | H3C-X2 | 3,5-dimethylbenzyl-X3 | X4-(CH2)3-N(CH3)-CH2CH2-phenyl | 515.4 | 8.1 |
| 83 | X1—CH3 | H3C-X2 | 3,5-dimethylbenzyl-X3 | X4-(CH2)3-N(CH3)-CH2CH2-phenyl | 515.4 | 8.1 |

-continued

| Examples | R1 | R2 | R3 | R4 | [M + H]+ | rt (min) |
|---|---|---|---|---|---|---|
| 84 | H | (CH(CH3)2 with X2) | 3,5-dimethylbenzyl-X3 | X4-(CH2)3-N(CH3)-CH2CH2-Ph | 529.5 | 8.4 |
| 85 | H | (tetrahydropyran-X2) | 3,5-dimethylbenzyl-X3 | X4-(CH2)3-N(CH3)-CH2CH2-Ph | 557.4 | 8.0 |
| 86 |  | (cyclohexyl-X2) | 3,5-dimethylbenzyl-X3 | X4-(CH2)3-N(CH3)-CH2CH2-Ph | 569.5 | 8.9 |
| 87 | H | (cycloheptyl-X2) | 3,5-dimethylbenzyl-X3 | X4-(CH2)3-N(CH3)-CH2CH2-Ph | 583.5 | 9.2 |

-continued
| Examples | R1 | R2 | R3 | R4 | [M+H]+ | rt (min) |
|---|---|---|---|---|---|---|
| 88 | H | 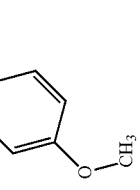 | 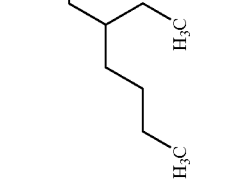 | 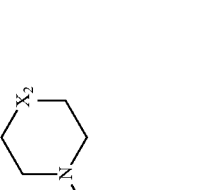 | 607.5 | 8.7 |
| 89 | H | 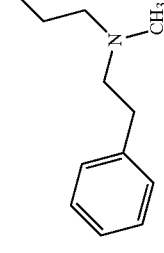 | 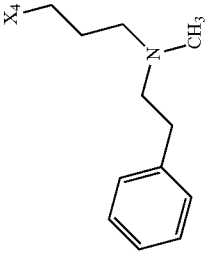 | 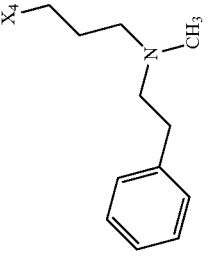 | 599.5 | 9.8 |
| 90 | | 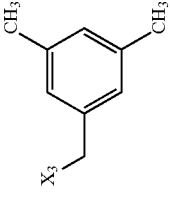 | 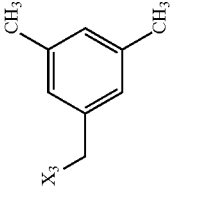 | 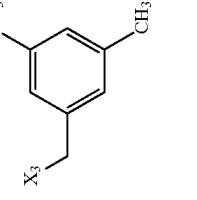 | 628.5 | 8.4 |
| 91 | | 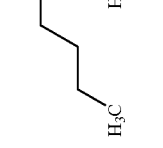 | 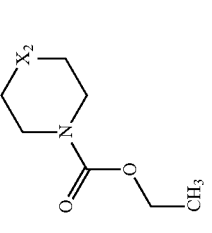 | 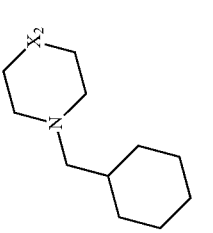 | 652.5 | 7.6 |

-continued

| Examples | R1 | R2 | R3 | R4 | [M + H]⁺ | rt (min) |
|---|---|---|---|---|---|---|
| 92 | | 4-benzylpiperidine with X₂ | 3,5-dimethylbenzyl with X₃ | N-methyl-N-phenethyl-propyl with X₄ | 645.5 | 9.7 |
| 93 | | 1-(2,6-dimethylphenyl)piperazine with X₂ | 3,5-dimethylbenzyl with X₃ | N-methyl-N-phenethyl-propyl with X₄ | 660.6 | 9.9 |
| 94 | | tetrahydroisoquinoline with X₂ | 3,5-dimethylbenzyl with X₃ | N-methyl-N-phenethyl-propyl with X₄ | 603.4 | 9.1 |
| 95 | H | benzo[1,3]dioxol-5-ylmethyl with X₂ | 3,5-dimethylbenzyl with X₃ | N-methyl-N-phenethyl-propyl with X₄ | 621.4 | 8.7 |

-continued
| Examples | R1 | R2 | R3 | R4 | [M + H]⁺ | rt (min) |
|---|---|---|---|---|---|---|
| 96 | H | 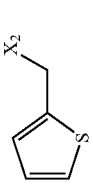 | 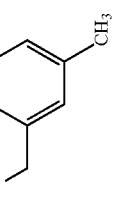 | 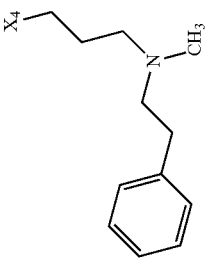 | 583.4 | 8.7 |
| 97 | H | 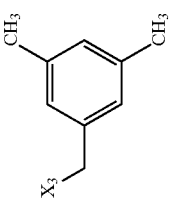 | 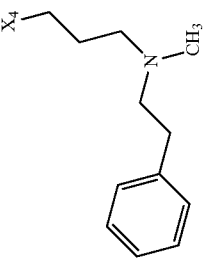 | 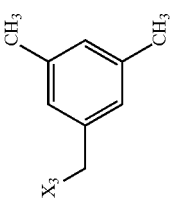 | 674.5 | 8.7 |
| 98 | H | 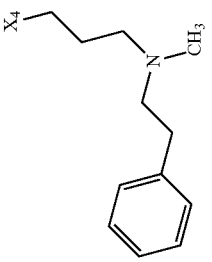 | 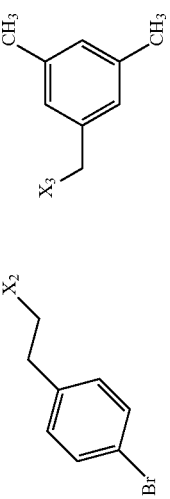 |  | 605.5 | 9.1 |
| 99 | H | | | | 669.4 | 9.3 |

-continued

| Examples | R1 | R2 | R3 | R4 | [M + H]⁺ | rt (min) |
|---|---|---|---|---|---|---|
| 100 |   | X₂-(4-pyrrolidin-1-yl-piperidinyl) | 3,5-dimethylbenzyl-X₃ | X₄-(CH₂)₃-N(CH₃)-CH₂CH₂-phenyl | 624.5 | 7.2 |
| 101 | H | X₂-CH₂-(4-biphenyl) | 3,5-dimethylbenzyl-X₃ | X₄-(CH₂)₃-N(CH₃)-CH₂CH₂-phenyl | 653.5 | 9.5 |
| 102 | H | X₂-CH₂-CH(CH₃)-CH(CH₃)(H₃C) (isobutyl-type) | 3,5-dimethylbenzyl-X₃ | X₄-(CH₂)₃-N(CH₃)-CH₂CH₂-phenyl | 543.5 | 8.6 |
| 103 | H | X₂-CH₂-cyclohexyl | 3,5-dimethylbenzyl-X₃ | X₄-(CH₂)₃-N(CH₃)-CH₂CH₂-phenyl | 583.5 | 9.2 |

-continued
| Examples | R1 | R2 | R3 | R4 | [M + H]+ | rt (min) |
|---|---|---|---|---|---|---|
| 104 | |  |  |  | 598.5 | 7.2 |
| 105 | | 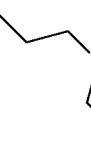 |  | 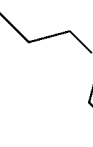 | 702.5 | 8.0 |
| 106 | | 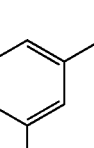 |  | 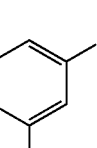 | 676.5 | 7.5 |
| 107 | | 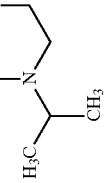 |  | 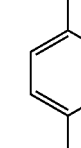 | 692.5 | 9.0 |

-continued

| Examples | R1 | R2 | R3 | R4 | [M + H]⁺ | rt (min) |
|---|---|---|---|---|---|---|
| 108 | H | 3,5-dichlorobenzyl-X₂ | 3,5-dimethylbenzyl-X₃ | X₄-(CH₂)₃-N(CH₃)-CH₂CH₂-phenyl | 645.4 | 9.5 |
| 109 | H | 2-methyl-4-methylbenzyl-X₂ | 3,5-dimethylbenzyl-X₃ | X₄-(CH₂)₃-N(CH₃)-CH₂CH₂-phenyl | 605.5 | 9.2 |
| 110 | isobutyl-X₁ | isobutyl-X₂ | X₃-CH₂-C(=O)-(2-methoxyphenyl) | X₄-(CH₂)₃-N(CH₃)-CH₂CH₂-phenyl | 629.0 | 9.4 |
| 111 | isobutyl-X₁ | isobutyl-X₂ | X₃-CH₂-C(=O)-(4-pyrrolidinylphenyl) | X₄-(CH₂)₃-N(CH₃)-CH₂CH₂-phenyl | 668.0 | 9.8 |

| Examples | R1 | R2 | R3 | R4 | [M+H]+ | rt (min) |
|---|---|---|---|---|---|---|
| 112 | isobutyl-X1 | isobutyl-X2 | 2,4-dimethoxyphenacyl-X3 | phenethyl-N(CH3)-butyl-X4 | 659.0 | 9.4 |
| 113 | isobutyl-X1 | isobutyl-X2 | adamantyl ketone-X3 | phenethyl-N(CH3)-butyl-X4 | 657.0 | 10.4 |
| 114 | isobutyl-X1 | isobutyl-X2 | 3,4,5-trimethoxyphenacyl-X3 | phenethyl-N(CH3)-butyl-X4 | 689.0 | 9.3 |
| 115 | isobutyl-X1 | isobutyl-X2 | 2-bromophenacyl-X3 | phenethyl-N(CH3)-butyl-X4 | 676.8 | 9.5 |

| Examples | R1 | R2 | R3 | R4 | [M + H]⁺ | rt (min) |
|---|---|---|---|---|---|---|
| 116 | isobutyl-X₁ | isobutyl-X₂ | phenylpropanoyl-X₃ | X₄-(CH₂)₃-N(CH₃)-CH₂CH₂-phenyl | 626.9 | 9.7 |
| 117 | isobutyl-X₁ | isobutyl-X₂ | benzofuran-2-yl-C(O)CH₂-X₃ | X₄-(CH₂)₃-N(CH₃)-CH₂CH₂-phenyl | 638.9 | 9.5 |
| 118 | isobutyl-X₁ | isobutyl-X₂ | benzothiophen-2-yl-C(O)CH₂-X₃ | X₄-(CH₂)₃-N(CH₃)-CH₂CH₂-phenyl | 654.9 | 9.7 |
| 119 | H | 4-(N,N-diethylamino)phenyl-X₂ | adamantyl-C(O)CH₂-X₃ | X₄-(CH₂)₃-N(CH₃)-CH₂CH₂-phenyl | 692.9 | 8.3 |

-continued
| Examples | R1 | R2 | R3 | R4 | [M + H]⁺ | rt (min) |
|---|---|---|---|---|---|---|
| 120 | H |  | 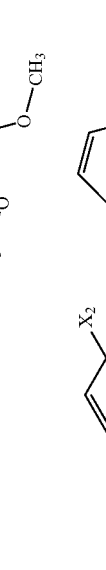 | 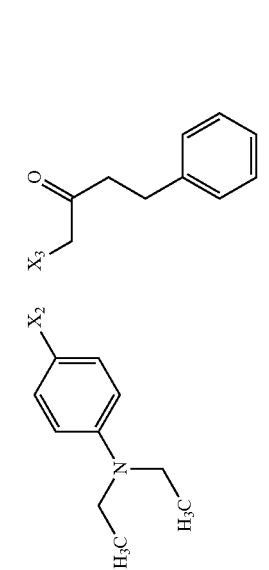 | 723.8 | 7.7 |
| 121 | H |  | 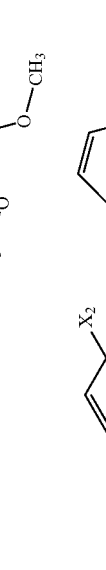 | 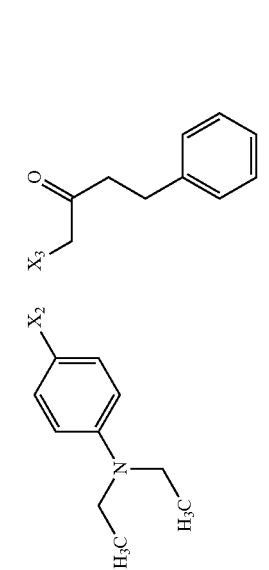 | 711.7 | 7.8 |
| 122 | H |  | 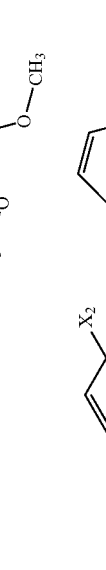 | 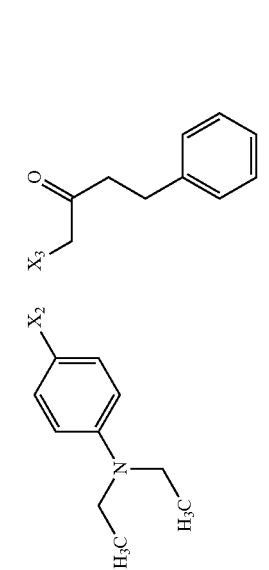 | 661.9 | 7.9 |
| 123 | H |  | 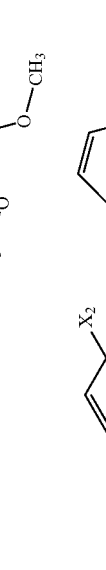 | 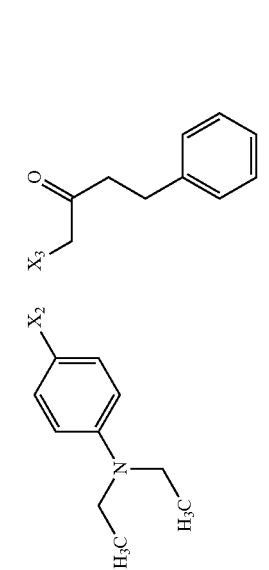 | 673.9 | 7.8 |

-continued
| Examples | R1 | R2 | R3 | R4 | [M + H]+ | rt (min) |
|---|---|---|---|---|---|---|
| 124 | H |  |  |  | 689.9 | 8.0 |
| 125 |  |  |  |  | 629.9 | 8.9 |
| 126 |  | 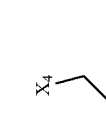 |  | 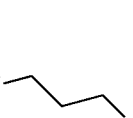 | 669.0 | 9.3 |
| 127 |  |  | 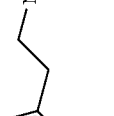 | 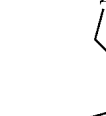 | 659.9 | 8.9 |

-continued

| Examples | R1 | R2 | R3 | R4 | [M + H]+ | rt (min) |
|---|---|---|---|---|---|---|
| 128 | isobutyl-X₁ | X₂-isobutyl | adamantyl-C(O)-CH₂-X₃ | X₄-(CH₂)₃-N(CH₃)-CH₂CH₂-(2-pyridyl) | 658.0 | 9.9 |
| 129 | isobutyl-X₁ | X₂-isobutyl | 3,4,5-trimethoxyphenyl-C(O)-CH₂-X₃ | X₄-(CH₂)₃-N(CH₃)-CH₂CH₂-(2-pyridyl) | 690.0 | 8.8 |
| 130 | isobutyl-X₁ | X₂-isobutyl | 2-bromophenyl-C(O)-CH₂-X₃ | X₄-(CH₂)₃-N(CH₃)-CH₂CH₂-(2-pyridyl) | 677.8 | 9.1 |
| 131 | isobutyl-X₁ | X₂-isobutyl | X₃-CH₂-C(O)-CH₂CH₂-phenyl | X₄-(CH₂)₃-N(CH₃)-CH₂CH₂-(2-pyridyl) | 628.0 | 9.1 |

| Examples | R1 | R2 | R3 | R4 | [M+H]⁺ | rt (min) |
|---|---|---|---|---|---|---|
| 132 | isobutyl-X₁ | isobutyl-X₂ | benzofuran-2-yl-C(O)-CH₂-X₃ | X₄-(CH₂)₃-N(CH₃)-CH₂CH₂-(pyridin-2-yl) | 640.0 | 9.1 |
| 133 | isobutyl-X₁ | isobutyl-X₂ | benzothiophen-2-yl-C(O)-CH₂-X₃ | X₄-(CH₂)₃-N(CH₃)-CH₂CH₂-(pyridin-2-yl) | 655.9 | 9.3 |
| 134 | H | 2-methoxy-4-methylphenyl-X₂ | 3,5-dimethylbenzyl-X₃ | X₄-(CH₂)₃-N(CH₃)-CH₂CH₂-phenyl | 607.0 | 9.8 |
| 135 | H | 3-(methylthio)phenyl-X₂ | 3,5-dimethylbenzyl-X₃ | X₄-(CH₂)₃-N(CH₃)-CH₂CH₂-phenyl | 609.0 | 9.6 |

-continued
| Examples | R1 | R2 | R3 | R4 | [M + H]⁺ | rt (min) |
|---|---|---|---|---|---|---|
| 136 | H | 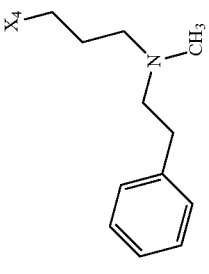 | 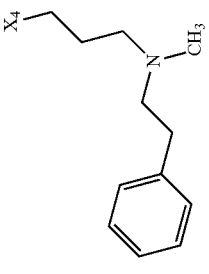 | 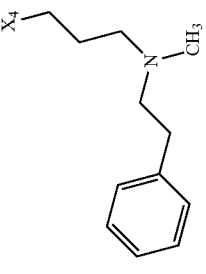 | 619.0 | 10.1 |
| 137 | H | 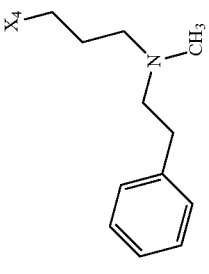 | 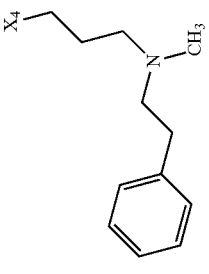 | 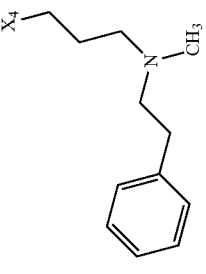 | 621.0 | 9.1 |
| 138 | H | 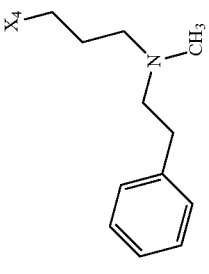 | 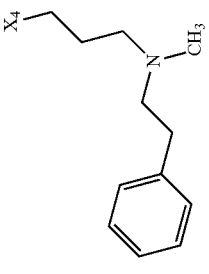 | 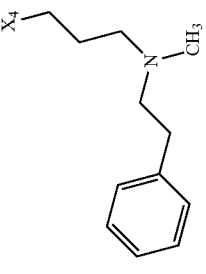 | 639.0 | 10.0 |
| 139 | H | 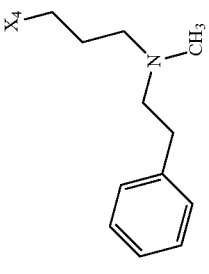 | 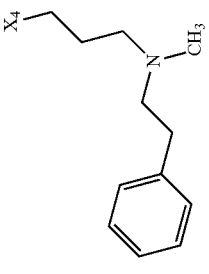 | 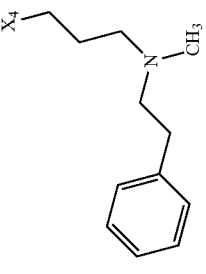 | 653.0 | 9.1 |

| Examples | R1 | R2 | R3 | R4 | [M+H]⁺ | rt (min) |
|---|---|---|---|---|---|---|
| 140 | H | 5-indolyl-X₂ | 3,5-dimethylbenzyl-X₃ | X₄-(CH₂)₄-N(CH₃)-CH₂CH₂-phenyl | 602.0 | 9.0 |
| 141 | H | 4-(NHC(O)CH₃)phenyl-X₂ | 3,5-dimethylbenzyl-X₃ | X₄-(CH₂)₄-N(CH₃)-CH₂CH₂-phenyl | 620.0 | 8.6 |
| 142 | H | 2-methyl-4-bromo-phenyl-X₂ | 3,5-dimethylbenzyl-X₃ | X₄-(CH₂)₄-N(CH₃)-CH₂CH₂-phenyl | 654.9 | 10.0 |
| 143 | H | 4-(N(SO₂-4-methylphenyl))phenyl-X₂ | 3,5-dimethylbenzyl-X₃ | X₄-(CH₂)₄-N(CH₃)-CH₂CH₂-phenyl | 731.9 | 9.4 |

-continued
| Examples | R1 | R2 | R3 | R4 | [M + H]⁺ | rt (min) |
|---|---|---|---|---|---|---|
| 144 | H |  | 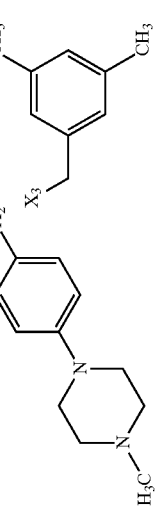 | 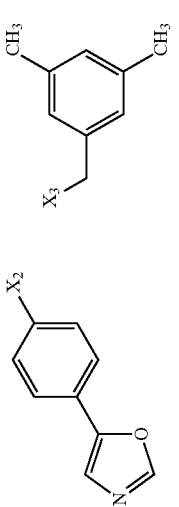 | 661.1 | 7.9 |
| 145 | H | 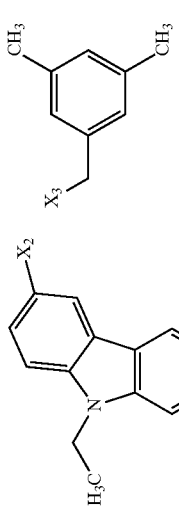 | | 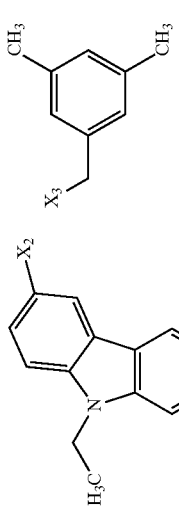 | 630.0 | 9.1 |
| 146 | H | 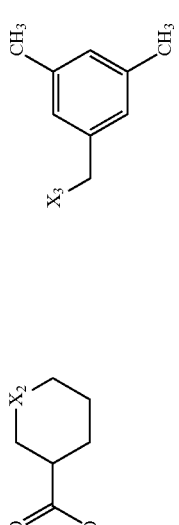 | | 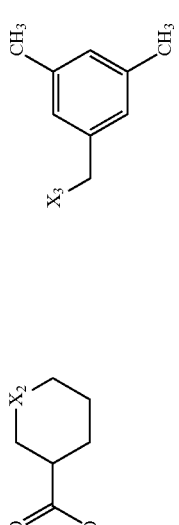 | 680.0 | 10.1 |
| 147 | | 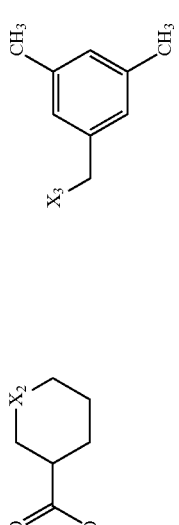 | | | 626.9 | 9.2 |

| Examples | R1 | R2 | R3 | R4 | [M + H]+ | rt (min) |
|---|---|---|---|---|---|---|
| 148 | | 3-(diethylcarbamoyl)cyclohexyl (X2) | 3,5-dimethylbenzyl (X3) | N-methyl-N-(2-phenylethyl)aminobutyl (X4) | 653.9 | 8.8 |
| 149 | H | 1-benzylpiperidin-4-yl (X2) | 3,5-dimethylbenzyl (X3) | N-methyl-N-(2-phenylethyl)aminobutyl (X4) | 660.0 | 8.0 |
| 150 | | 4-(2-methoxyphenyl)piperazin-1-yl (X2) | 3,5-dimethylbenzyl (X3) | N-methyl-N-(2-phenylethyl)aminobutyl (X4) | 662.0 | 9.2 |
| 151 | | 6,7-dimethoxy-1,2,3,4-tetrahydroisoquinolin-2-yl (X2) | 3,5-dimethylbenzyl (X3) | N-methyl-N-(2-phenylethyl)aminobutyl (X4) | 662.9 | 9.1 |

-continued
| Examples | R1 | R2 | R3 | R4 | [M + H]⁺ | rt (min) |
|---|---|---|---|---|---|---|
| 152 | | 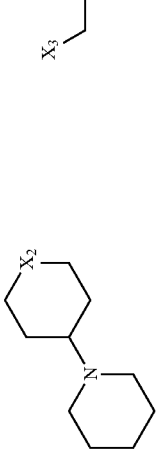 |  | 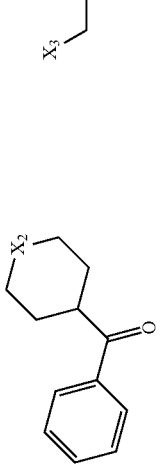 | 638.0 | 7.8 |
| 153 | | 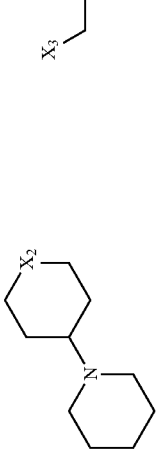 |  | 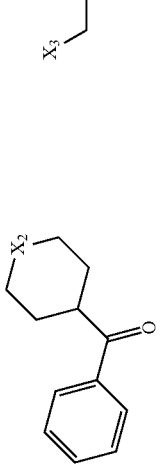 | 658.9 | 9.3 |
| 154 | | 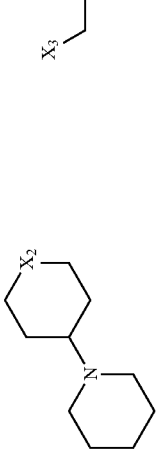 |  | 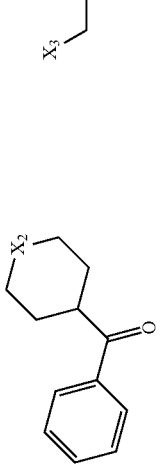 | 689.9 | 9.3 |
| 155 | | 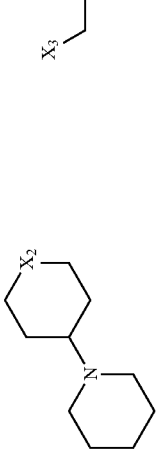 |  | 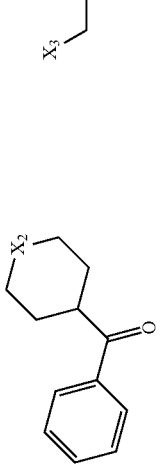 | 633.0 | 7.8 |

| Examples | R1 | R2 | R3 | R4 | [M+H]⁺ | rt (min) |
|---|---|---|---|---|---|---|
| 156 | H | pyrrolidine-(CH₂)₃-X₂ | 3,5-dimethylbenzyl-X₃ | PhCH₂CH₂N(CH₃)(CH₂)₃-X₄ | 598.0 | 7.8 |
| 157 | | morpholine-C(O)CH₂-piperazine-X₂ | 3,5-dimethylbenzyl-X₃ | PhCH₂CH₂N(CH₃)(CH₂)₃-X₄ | 683.0 | 7.8 |
| 158 | | thiophene-CH₂CH₂-piperazine-X₂ | 3,5-dimethylbenzyl-X₃ | PhCH₂CH₂N(CH₃)(CH₂)₃-X₄ | 666.0 | 8.1 |
| 159 | | PhCH₂CH₂-homopiperazine-X₂ | 3,5-dimethylbenzyl-X₃ | PhCH₂CH₂N(CH₃)(CH₂)₃-X₄ | 674.0 | 8.2 |

-continued
| Examples | R1 | R2 | R3 | R4 | [M + H]⁺ | rt (min) |
|---|---|---|---|---|---|---|
| 160 |  | 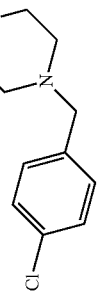 | 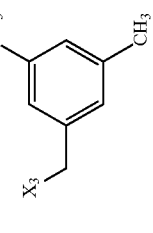 | 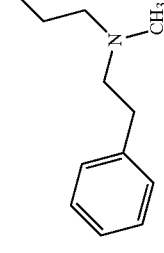 | 679.9 | 8.2 |
| 161 |  | 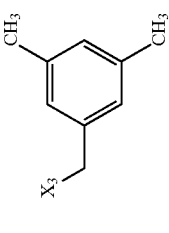 | 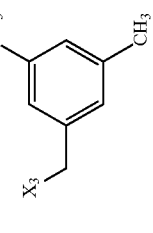 | 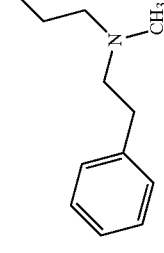 | 660.0 | 8.2 |
| 162 | H | 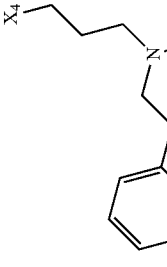 | 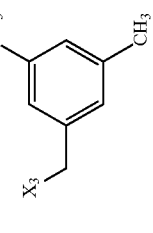 | 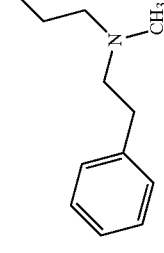 | 586.0 | 7.8 |
| 163 |  | 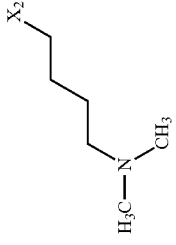 | 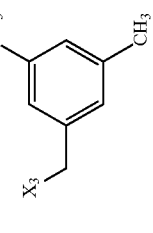 | 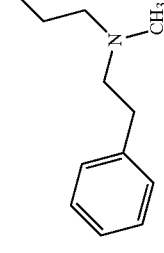 | 666.0 | 8.4 |

-continued

| Examples | R1 | R2 | R3 | R4 | [M+H]⁺ | rt (min) |
|---|---|---|---|---|---|---|
| 164 | | X₂-piperidine-N-(CH₂)₃-pyrrolidine | 3,5-dimethylbenzyl-X₃ | X₄-(CH₂)₃-N(CH₃)-CH₂CH₂-phenyl | 667.0 | 7.5 |
| 165 | | X₂-piperidine-N-cyclopentyl | 3,5-dimethylbenzyl-X₃ | X₄-(CH₂)₃-N(CH₃)-CH₂CH₂-phenyl | 624.0 | 7.9 |
| 166 | | X₂-piperidine-N-pyrazinyl | 3,5-dimethylbenzyl-X₃ | X₄-(CH₂)₃-N(CH₃)-CH₂CH₂-phenyl | 633.9 | 8.7 |
| 167 | H₃C-CH(CH₂-X₁)-CH₃ | H₃C-CH(CH₃)-CH₂-X₂ | X₂-CH₂-(2-phenylsulfonylmethyl)phenyl | X₄-(CH₂)₃-N(CH₃)-CH₂CH₂-phenyl | 725.0 | 9.5 |

-continued

| Examples | R1 | R2 | R3 | R4 | [M + H]⁺ | rt (min) |
|---|---|---|---|---|---|---|
| 168 | X₁-CH₂-CH(CH₃)-CH₃ (isobutyl) | (CH₃)₂CH-CH₂-X₂ | X₂-CH₂-(anthraquinon-2-yl) | X₄-(CH₂)₃-N(CH₃)-CH₂CH₂-phenyl | 700.9 | 9.8 |
| 169 | X₁-CH₂-CH(CH₃)-CH₃ | (CH₃)₂CH-CH₂-X₂ | X₃-CH₂-(2-methylphenyl) | X₄-(CH₂)₃-N(CH₃)-CH₂CH₂-phenyl | 585.0 | 9.5 |
| 170 | X₁-CH₂-CH(CH₃)-CH₃ | (CH₃)₂CH-CH₂-X₂ | X₃-CH₂-(4-benzoylphenyl) | X₄-(CH₂)₃-N(CH₃)-CH₂CH₂-phenyl | 674.9 | 9.7 |

-continued

| Examples | R1 | R2 | R3 | R4 | [M + H]⁺ | rt (min) |
|---|---|---|---|---|---|---|
| 171 | (isobutyl-X₁) | (isobutyl-X₂) | 2-bromobenzyl-X₃ | X₄-(CH₂)₃-N(CH₃)-(CH₂)₂-phenyl | 648.8 | 9.7 |
| 172 | (isobutyl-X₁) | (isobutyl-X₂) | 2-(phenylsulfonylmethyl)benzyl-X₂ | X₄-(CH₂)₃-N(CH₃)-(CH₂)₂-(2-pyridyl) | 726.0 | 9.1 |
| 173 | (isobutyl-X₁) | (isobutyl-X₂) | anthraquinonyl-CH₂-X₂ | X₄-(CH₂)₃-N(CH₃)-(CH₂)₂-(2-pyridyl) | 701.9 | 9.4 |
| 174 | (isobutyl-X₁) | (isobutyl-X₂) | 2-methylbenzyl-X₃ | X₄-(CH₂)₃-N(CH₃)-(CH₂)₂-(2-pyridyl) | 585.9 | 9.1 |

-continued
| Examples | R1 | R2 | R3 | R4 | [M + H]+ | rt (min) |
|---|---|---|---|---|---|---|
| 175 |  |  | 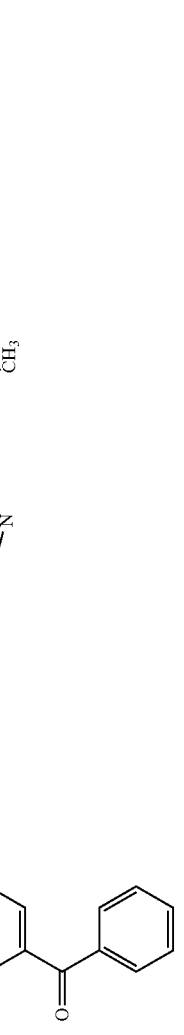 | 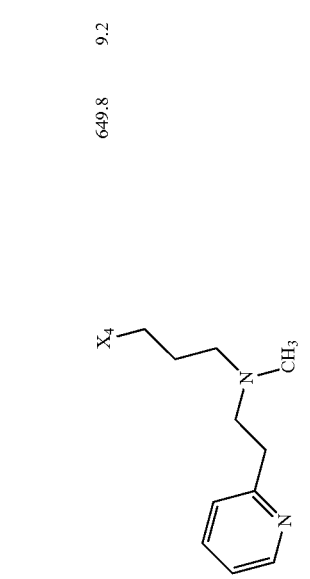 | 675.9 | 9.3 |
| 176 |  |  | 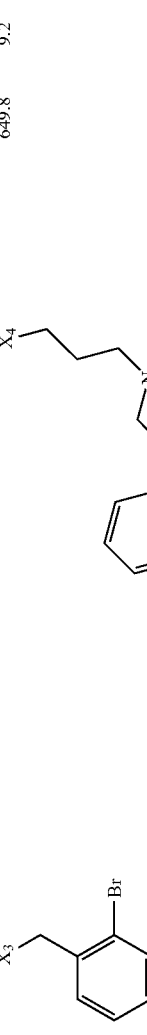 | 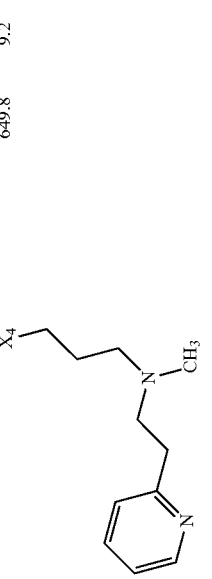 | 649.8 | 9.2 |
| 177 |  |  |  | 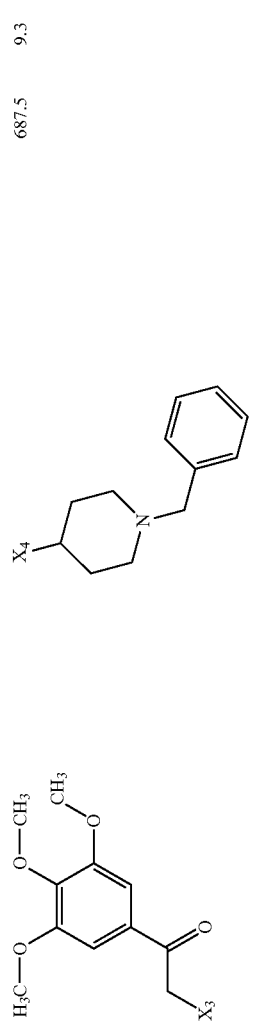 | 687.5 | 9.3 |

| Examples | R1 | R2 | R3 | R4 | [M + H]+ | rt (min) |
|---|---|---|---|---|---|---|
| 178 | isobutyl-X₁ | X₂-isobutyl | 3,4,5-trimethoxyphenacyl-X₃ | X₄-(CH₂)₂-piperazine-N-benzyl | 716.5 | 9.3 |
| 179 | isobutyl-X₁ | X₂-isobutyl | 3,4,5-trimethoxyphenacyl-X₃ | X₄-(CH₂)₃-N(CH₃)-benzyl | 675.5 | 9.3 |
| 180 | isobutyl-X₁ | X₂-isobutyl | 3,4,5-trimethoxyphenacyl-X₃ | X₄-(CH₂)₃-N(CH₃)-CH₂-pyridin-3-yl | 676.5 | 8.8 |

-continued

| Examples | R1 | R2 | R3 | R4 | [M + H]+ | rt (min) |
|---|---|---|---|---|---|---|
| 181 | isobutyl-X1 | isobutyl-X2 | adamantyl-C(O)-CH2-X3 | X4-piperidine-N-benzyl | 655.5 | 10.4 |
| 182 | isobutyl-X1 | isobutyl-X2 | adamantyl-C(O)-CH2-X3 | X4-CH2CH2-piperazine-N-benzyl | 684.5 | 10.4 |
| 183 | isobutyl-X1 | isobutyl-X2 | adamantyl-C(O)-CH2-X3 | X4-(CH2)3-N(CH3)-benzyl | 643.5 | 10.4 |

-continued
| Examples | R1 | R2 | R3 | R4 | [M + H]+ | rt (min) |
|---|---|---|---|---|---|---|
| 184 | 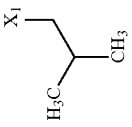 | 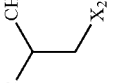 | 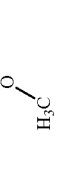 |  | 662.5 | 8.9 |
| 185 | | 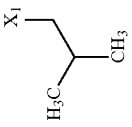 | 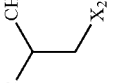 | 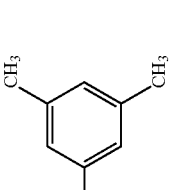 | 569.5 | 9.1 |
| 186 | H |  | 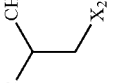 | 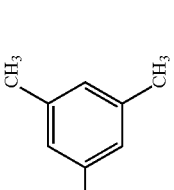 | 571.5 | 9.3 |
| 187 | |  | 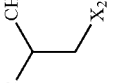 | 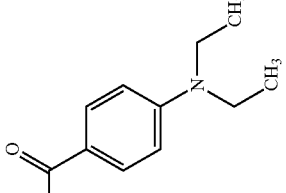 | 696.3 | 7.8 |

| Examples | R1 | R2 | R3 | R4 | [M+H]⁺ | rt (min) |
|---|---|---|---|---|---|---|
| 188 | | ethyl piperazine-1-carboxylate (X₂) | 4-(diethylamino)phenyl ketone with X₂ | pyridin-2-yl ethyl-N-methyl-butyl (X₄) | 700.3 | 8.7 |
| 189 | | 1-cyclopentylpiperidine (X₂) | 3-bromobenzyl (X₃) | pyridin-2-yl ethyl-N-methyl-butyl (X₄) | 674.2 | 7.6 |
| 190 | | ethyl piperazine-1-carboxylate (X₂) | 3-bromobenzyl (X₃) | pyridin-2-yl ethyl-N-methyl-butyl (X₄) | 679.1 | 8.4 |
| 191 | H | cycloheptyl (X₂) | 3-bromobenzyl (X₃) | pyridin-2-yl ethyl-N-methyl-butyl (X₄) | 634.2 | 9.5 |

-continued

| Examples | R1 | R2 | R3 | R4 | [M + H]⁺ | rt (min) |
|---|---|---|---|---|---|---|
| 192 |  | piperidine-3-carboxamide N,N-diethyl with X₂ | 3-Br benzyl with X₃ | 2-(pyridin-2-yl)ethyl-N-methyl-butyl with X₄ | 705.2 | 8.6 |
| 193 |  | 4-(3-chlorophenyl)piperazine with X₂ | 3-Br benzyl with X₃ | 2-(pyridin-2-yl)ethyl-N-methyl-butyl with X₄ | 717.1 | 9.9 |
| 194 | H | 1-(ethoxycarbonyl)piperidin-4-yl with X₂ | 3-Br benzyl with X₃ | 2-(pyridin-2-yl)ethyl-N-methyl-butyl with X₄ | 693.2 | 8.8 |
| 195 |  | 4-(piperidin-1-yl)piperidine with X₂ | 3-Br benzyl with X₃ | 2-(pyridin-2-yl)ethyl-N-methyl-butyl with X₄ | 689.2 | 7.8 |

-continued
| Examples | R1 | R2 | R3 | R4 | [M + H]+ | rt (min) |
|---|---|---|---|---|---|---|
| 196 | | 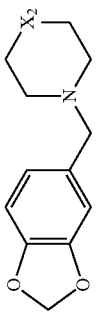 | 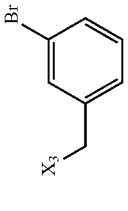 | 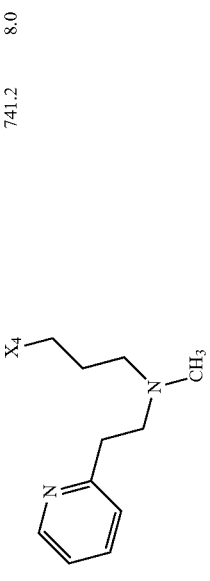 | 741.2 | 8.0 |
| 197 | | 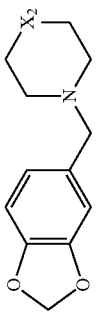 | 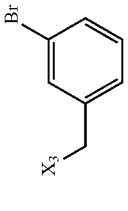 | 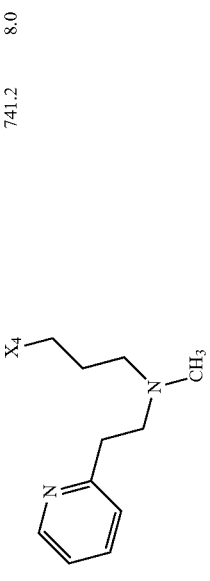 | 654.2 | 9.4 |
| 198 | 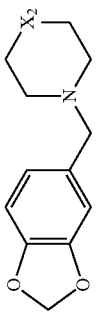 | 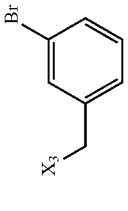 | 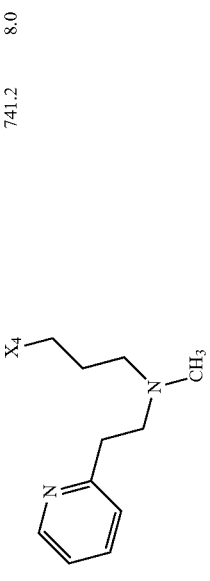 | 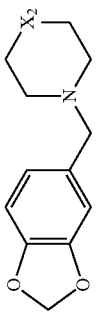 | 692.4 | 8.4 |
| 199 | 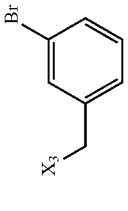 | H | 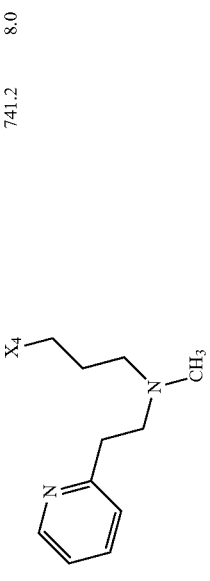 | | 629.1 | 7.9 |

| Examples | R1 | R2 | R3 | R4 | [M + H]+ | rt (min) |
|---|---|---|---|---|---|---|
| 200 |  | X1-piperazine-N-(4-methoxyphenyl) | 3-Br-benzyl-X3 | 2-(pyridin-2-yl)ethyl-N(CH3)-butyl-X4 | 713.2 | 9.0 |
| 201 | X1-(CH2)3-N(CH2CH3)2 | H | 3-Br-benzyl-X3 | 2-(pyridin-2-yl)ethyl-N(CH3)-butyl-X4 | 651.2 | 7.8 |
| 202 | 2,6-dimethylbenzyl-X1 | H | 3-Br-benzyl-X3 | 2-(pyridin-2-yl)ethyl-N(CH3)-butyl-X4 | 656.2 | 9.5 |
| 203 |  | X1-piperazine-N-(CH2)3-N(CH3)2 | 3-Br-benzyl-X3 | 2-(pyridin-2-yl)ethyl-N(CH3)-butyl-X4 | 720.3 | 7.5 |

-continued

| Examples | R1 | R2 | R3 | R4 | [M+H]+ | rt (min) |
|---|---|---|---|---|---|---|
| 204 | | piperazine-N-(CH2)3-CH3 with X1 | 3-Br-benzyl-X3 | X4-(CH2)3-N(CH3)-(CH2)2-(2-pyridyl) | 663.2 | 7.9 |
| 205 | | piperazine-N-(2-pyrimidyl) with X1 | 3-Br-benzyl-X3 | X4-(CH2)3-N(CH3)-(CH2)2-(2-pyridyl) | 685.2 | 8.5 |
| 206 | | piperidine-N-cyclohexyl with X1 | 3-Br-benzyl-X3 | X4-(CH2)3-N(CH3)-(CH2)2-(2-pyridyl) | 689.3 | 8.0 |
| 207 | cycloheptyl-X1 | H | X3-CH2-C(O)-(4-(N(CH2CH3)2)phenyl) | X4-(CH2)3-N(CH3)-(CH2)2-phenyl | 654.3 | 10.1 |

| Examples | R1 | R2 | R3 | R4 | [M + H]$^+$ | rt (min) |
|---|---|---|---|---|---|---|
| 208 | 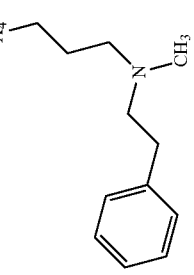 | 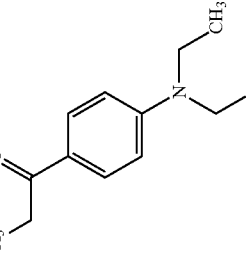 | 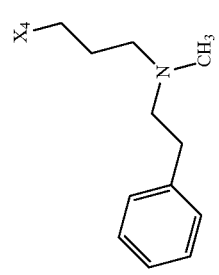 | 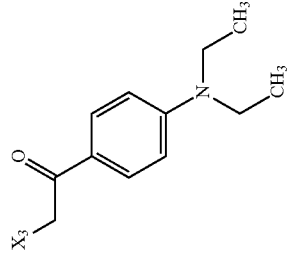 | 725.3 | 9.3 |
| 209 | 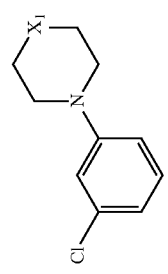 | 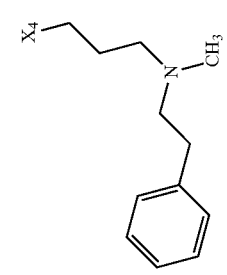 | 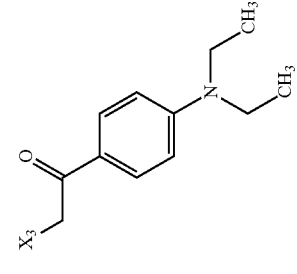 | | 737.3 | 10.4 |
| 210 | 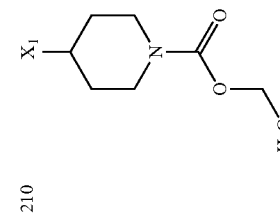 | H | | | 713.4 | 9.4 |

| Examples | R1 | R2 | R3 | R4 | [M + H]⁺ | rt (min) |
|---|---|---|---|---|---|---|
| 211 | | piperidin-1-yl-cyclohexyl-X₂ | X₃-C(O)-CH₂-C₆H₄-N(CH₂CH₃)₂ | X₄-(CH₂)₃-N(CH₃)-CH₂CH₂-C₆H₅ | 709.4 | 8.3 |
| 212 | | X₁-CH₂-(benzo[1,3]dioxol-5-yl)piperazine | X₃-C(O)-CH₂-C₆H₄-N(CH₂CH₃)₂ | X₄-(CH₂)₃-N(CH₃)-CH₂CH₂-C₆H₅ | 761.3 | 8.54 |
| 213 | | X₁-CH₂-(1,2,3,4-tetrahydroisoquinolin-2-yl) | X₃-C(O)-CH₂-C₆H₄-N(CH₂CH₃)₂ | X₄-(CH₂)₃-N(CH₃)-CH₂CH₂-C₆H₅ | 674.3 | 9.9 |

-continued

| Examples | R1 | R2 | R3 | R4 | [M + H]⁺ | rt (min) |
|---|---|---|---|---|---|---|
| 214 | X₁—CH₂-(2-pyridyl) | H | X₃—C(O)-C₆H₄-N(CH₂CH₃)₂ (para) | X₄—(CH₂)₃—N(CH₃)—CH₂CH₂-phenyl | 649.3 | 8.5 |
| 215 | | 4-(4-methoxyphenyl)piperazin-1-yl (X₁) | X₃—C(O)-C₆H₄-N(CH₂CH₃)₂ (para) | X₄—(CH₂)₃—N(CH₃)—CH₂CH₂-phenyl | 733.3 | 9.5 |
| 216 | X₁—(CH₂)₃—N(CH₂CH₃)₂ | H | X₃—C(O)-C₆H₄-N(CH₂CH₃)₂ (para) | X₄—(CH₂)₃—N(CH₃)—CH₂CH₂-phenyl | 671.3 | 8.3 |

-continued

| Examples | R1 | R2 | R3 | R4 | [M + H]⁺ | rt (min) |
|---|---|---|---|---|---|---|
| 217 | | H | | | 676.3 | 10.1 |
| 218 | | | | | 740.4 | 7.9 |
| 219 | | | | | 683.3 | 8.4 |

-continued
| Examples | R1 R2 | R3 | R4 | [M + H]⁺ | rt (min) |
|---|---|---|---|---|---|
| 220 | 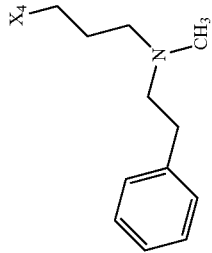 | 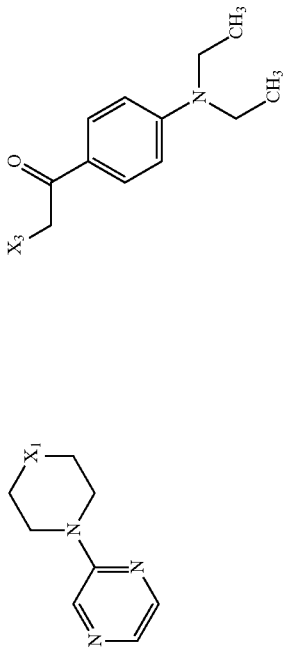 | 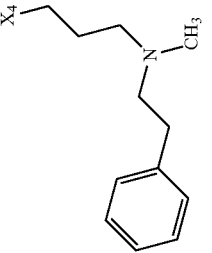 | 705.3 | 9.2 |
| 221 |  | 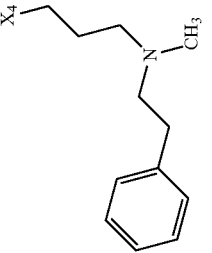 | 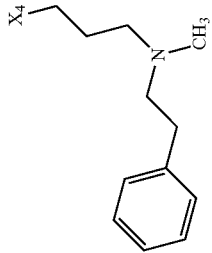 | 709.4 | 8.5 |
| 222 | 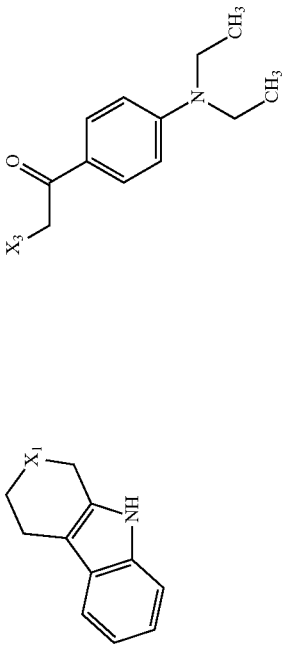 | 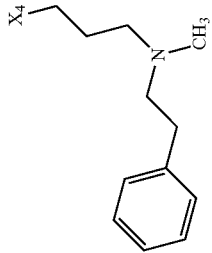 | 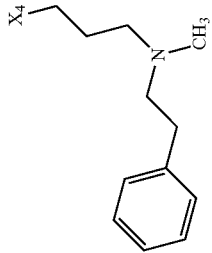 | 713.3 | 10.0 |

| Examples | R1 | R2 | R3 | R4 | [M + H]⁺ | rt (min) |
|---|---|---|---|---|---|---|
| 223 | (spiro indane-piperidine with X₁) | | (3-bromobenzyl with X₃) | (X₄-propyl-N(CH₃)-ethyl-pyridin-2-yl) | 708.2 | 10.0 |
| 224 | (X₁-ethyl-piperidine) | H | (X₃-CH₂-C(O)-4-(N,N-diethylamino)phenyl) | (X₄-propyl-N(CH₃)-ethyl-phenyl) | 669.4 | 8.2 |
| 225 | (X₁-CH₂-2,6-dimethoxyphenyl) | H | (X₃-CH₂-C(O)-4-(N,N-diethylamino)phenyl) | (X₄-propyl-N(CH₃)-ethyl-phenyl) | 708.3 | 9.6 |

-continued

| Examples | R1 | R2 | R3 | R4 | [M + H]+ | rt (min) |
|---|---|---|---|---|---|---|
| 226 | 2-pyridyl-CH2CH2-X1 | H | X3-CH2-C(O)-C6H4-N(CH2CH3)2 | X4-(CH2)3-N(CH3)-CH2CH2-C6H5 | 663.3 | 8.1 |
| 227 | (CH3)3C-CH(CH2-X1)-CH2-N(CH3)2 | H | X3-CH2-C(O)-C6H4-N(CH2CH3)2 | X4-(CH2)3-N(CH3)-CH2CH2-C6H5 | 671.4 | 8.2 |
| 228 | 2-Cl-C6H4-CH2CH2-X1 | H | X3-CH2-C(O)-C6H4-N(CH2CH3)2 | X4-(CH2)3-N(CH3)-CH2CH2-C6H5 | 696.3 | 9.8 |

-continued

| Examples | R1 | R2 | R3 | R4 | [M + H]⁺ | rt (min) |
|---|---|---|---|---|---|---|
| 229 | adamantyl-CH₂-X₁ | H | X₃-C(O)-C₆H₄-N(CH₂CH₃)₂ (para) | X₄-(CH₂)₃-N(CH₃)-CH₂CH₂-phenyl | 706.4 | 10.3 |
| 230 | H₃C-(CH₂)₂-X₁ | H₃C-CH(X₂)- | X₃-CH₂-C₆H₄-Br (meta) | X₄-(CH₂)₃-N(CH₃)-CH₂CH₂-(2-pyridyl) | 622.2 | 9.3 |
| 231 | (CH₃)(H₃C)CH-CH₂-X₁ | (CH₃)(H₃C)CH-CH₂-X₂ | X₃-CH₂-C₆H₄-Br (meta) | X₄-(CH₂)₄-N(CH₃)-CH₂CH₂-(2-pyridyl) | 678.2 | 10.4 |
| 232 | (H₃C)(H₃C)N-CH₂CH₂-X₁ | H | X₃-C(O)-CH₂-(3,4,5-trimethoxyphenyl) | X₄-(CH₂)₄-N(CH₃)-CH₂CH₂-(2-pyridyl) | 649.3 | 7.3 |

-continued
| Examples | R1 | R2 | R3 | R4 | [M + H]+ | rt (min) |
|---|---|---|---|---|---|---|
| 233 | 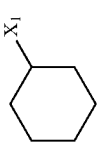 | H |  |  | 660.3 | 8.5 |
| 234 | |  |  | 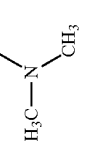 | 660.4 | 7.3 |
| 235 | 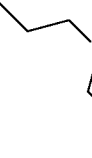 | H | 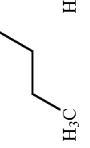 |  | 663.4 | 7.3 |
| 236 |  | H | | | 690.5 | 9.2 |

-continued

| Examples | R1 | R2 | R3 | R4 | [M + H]⁺ | rt (min) |
|---|---|---|---|---|---|---|
| 237 | (piperidine-piperidine attached via X₁) | piperidine-X₁ | X₃–C(O)–(3,4,5-trimethoxyphenyl) | X₄–(CH₂)₃–N(CH₃)–CH₂CH₂–(2-pyridyl) | 729.5 | 7.4 |
| 238 | morpholine-CH₂CH₂–X₁ | H | X₃–C(O)–(3,4,5-trimethoxyphenyl) | X₄–(CH₂)₃–N(CH₃)–CH₂CH₂–(2-pyridyl) | 691.4 | 7.4 |
| 239 | 4-aminophenyl-X₁ | H | X₃–C(O)–(3,4,5-trimethoxyphenyl) | X₄–(CH₂)₃–N(CH₃)–CH₂CH₂–(2-pyridyl) | 669.4 | 7.5 |
| 240 | imidazol-1-yl-(CH₂)₃–X₁ | H | X₃–C(O)–(3,4,5-trimethoxyphenyl) | X₄–(CH₂)₃–N(CH₃)–CH₂CH₂–(2-pyridyl) | 686.4 | 7.4 |

-continued

| Examples | R1 | R2 | R3 | R4 | [M + H]+ | rt (min) |
|---|---|---|---|---|---|---|
| 241 | X₁–CH₂CH₂CH₂–NH₂ | H | X₃–CH₂–C(=O)–(3,4,5-trimethoxyphenyl) | X₄–(CH₂)₃–N(CH₃)–CH₂CH₂-(2-pyridyl) | 621.3 | 7.3 |
| 242 | X₁–CH₂CH₂–(pyrrolidin-1-yl) | H | X₃–CH₂–C(=O)–(3,4,5-trimethoxyphenyl) | X₄–(CH₂)₃–N(CH₃)–CH₂CH₂-(2-pyridyl) | 675.4 | 7.4 |
| 243 | X₁–(CH₂)₅–NH₂ | H | X₃–CH₂–C(=O)–(3,4,5-trimethoxyphenyl) | X₄–(CH₂)₃–N(CH₃)–CH₂CH₂-(2-pyridyl) | 663.4 | 7.4 |
| 244 | X₁–CH₂–CH(CH₃)–CH₃ | H | X₃–CH₂–C(=O)–(3,4,5-trimethoxyphenyl) | X₄–(CH₂)₃–N(CH₃)–CH₂CH₂-(2-pyridyl) | 634.4 | 8.2 |

-continued

| Examples | R1 | R2 | R3 | R4 | [M + H]⁺ | rt (min) |
|---|---|---|---|---|---|---|
| 245 | (CH₃)(H₃C)N-CH₂CH₂CH₂CH₂-X₁ | H | X₃-C(O)-(3,4,5-trimethoxyphenyl) | X₄-CH₂CH₂CH₂-N(CH₃)-CH₂CH₂-(2-pyridyl) | 677.4 | 7.4 |
| 246 | X₁-CH₂-C(CH₃)₂-CH₂-N(CH₃)₂ | H | X₃-C(O)-(3,4,5-trimethoxyphenyl) | X₄-CH₂CH₂CH₂-N(CH₃)-CH₂CH₂-(2-pyridyl) | 691.4 | 7.4 |
| 247 | X₁-CH₂CH₂-CH(CH₃)-CH₃ | (H₃C)(CH₃)N-CH₂CH₂-X₂ | X₃-C(O)-(3,4,5-trimethoxyphenyl) | X₄-CH₂CH₂CH₂-N(CH₃)-CH₂CH₂-(2-pyridyl) | 718.6 | 9.5 |
| 248 | X₁-CH₂-CH₃ | (H₃C)(CH₃)N-CH₂CH₂-X₂ | X₃-C(O)-(3,4,5-trimethoxyphenyl) | X₄-CH₂CH₂CH₂-N(CH₃)-CH₂CH₂-(2-pyridyl) | 677.5 | 7.4 |

| Examples | R1 | R2 | R3 | R4 | [M + H]+ | rt (min) |
|---|---|---|---|---|---|---|
| 249 | isobutyl-X1 | X2-CH2-CH(CH3)2 | 3,4,5-trimethoxyphenyl-C(=O)-CH2-X3 | X4-CH2-NH-C(=O)-O-C(CH3)3 | 657.4 | 11.4 |
| 250 | isobutyl-X1 | X2-CH2-CH(CH3)2 | 3,4,5-trimethoxyphenyl-C(=O)-CH2-X3 | X4-(CH2)4-NH-C(=O)-O-C(CH3)3 | 685.4 | 11.7 |
| 251 | isobutyl-X1 | X2-CH2-CH(CH3)2 | 3,4,5-trimethoxyphenyl-C(=O)-CH2-X3 | X4-CH2-NH2 | 557.3 | 8.6 |
| 252 | isobutyl-X1 | X2-CH2-CH(CH3)2 | 3,4,5-trimethoxyphenyl-C(=O)-CH2-X3 | X4-(CH2)4-NH2 | 585.3 | 8.8 |

| Examples | R1 | R2 | R3 | R4 | [M+H]⁺ | rt (min) |
|---|---|---|---|---|---|---|
| 253 | | | | | 617.2 | 12.4 |
| 254 | | | | | 617.4 | 7.2 |
| 255 | | | | | 617.4 | 7.1 |
| 256 | | | | | 568.4 | 8.4 |

-continued

| Examples | R1 | R2 | R3 | R4 | [M + H]+ | rt (min) |
|---|---|---|---|---|---|---|
| 257 | isobutyl (H3C-CH(CH3)-CH2-X1) | H3C-CH(CH3)-CH2-X2 | 3-methylphenyl-CH2-X3 | X4-(CH2)3-N(CH3)-CH2CH2-phenyl | 568.3 | 7.8 |
| 258 | isobutyl | H3C-CH(CH3)-CH2-X2 | 3,5-dimethoxyphenyl-X3 | X4-(CH2)3-N(CH3)-CH2CH2-phenyl | 600.4 | 7.8 |
| 259 | H | 4-(N,N-diethylamino)phenyl-X2 | 3,5-dimethoxyphenyl-X3 | X4-(CH2)3-N(CH3)-CH2CH2-phenyl | 747.5 | 6.7 |
| 260 | isobutyl | H3C-CH(CH3)-CH2-X2 | 3,5-dimethoxyphenyl-X3 | X4-(CH2)3-N(CH3)-CH2CH2-(2-pyridyl) | 601.4 | 7.4 |

-continued

| Examples | R1 | R2 | R3 | R4 | [M + H]⁺ | rt (min) |
|---|---|---|---|---|---|---|
| 261 | H₃C-CH(CH₃)-CH₂-X₁ | X₂-CH₂-CH(CH₃)-CH₃ | 3-Cl-C₆H₄-X₃ | X₄-(CH₂)₃-N(CH₃)-CH₂CH₂-C₆H₅ | 574.4 | 8.3 |
| 262 | H₃C-CH(CH₃)-CH₂-X₁ | X₂-CH₂-CH(CH₃)-CH₃ | 1-naphthyl-X₃ | X₄-(CH₂)₃-N(CH₃)-CH₂CH₂-C₆H₅ | 590.4 | 8.2 |
| 263 | H₃C-CH(CH₃)-CH₂-X₁ | X₂-CH₂-CH(CH₃)-CH₃ | 3-OMe-4-NO₂-C₆H₃-X₃ | X₄-(CH₂)₃-N(CH₃)-CH₂CH₂-C₆H₅ | 615.4 | 8.6 |
| 264 | H₃C-CH(CH₃)-CH₂-X₁ | X₂-CH₂-CH(CH₃)-CH₃ | 2,3-diMe-C₆H₃-X₃ | X₄-(CH₂)₃-N(CH₃)-CH₂CH₂-C₆H₅ | 568.5 | 8.1 |

-continued

| Examples | R1 | R2 | R3 | R4 | [M + H]⁺ | rt (min) |
|---|---|---|---|---|---|---|
| 265 | H₃C–CH(CH₃)–CH₂–X₁ | X₂–CH₂–CH(CH₃)–CH₃ | 4-(H₃C–C(=O))–C₆H₄–X₃ | X₄–(CH₂)₃–N(CH₃)–CH₂CH₂–C₆H₅ | 582.4 | 8.0 |
| 266 | H₃C–CH(CH₃)–CH₂–X₁ | X₂–CH₂–CH(CH₃)–CH₃ | 4-(H₃C–CH(CH₃))–C₆H₄–X₃ | X₄–(CH₂)₃–N(CH₃)–CH₂CH₂–C₆H₅ | 582.5 | 8.5 |
| 267 | H₃C–CH(CH₃)–CH₂–X₁ | X₂–CH₂–CH(CH₃)–CH₃ | 2,6-difluorophenyl–X₃ | X₄–(CH₂)₃–N(CH₃)–CH₂CH₂–C₆H₅ | 576.4 | 8.1 |
| 268 | H₃C–CH(CH₃)–CH₂–X₁ | X₂–CH₂–CH(CH₃)–CH₃ | 3-NC–C₆H₄–X₃ | X₄–(CH₂)₃–N(CH₃)–CH₂CH₂–C₆H₅ | 565.4 | 8.1 |

| Examples | R1 | R2 | R3 | R4 | [M + H]⁺ | rt (min) |
|---|---|---|---|---|---|---|
| 269 | H₃C-CH(CH₃)-CH₂-X₁ | X₂-CH₂-CH(CH₃)-CH₃ | benzo[1,3]dioxol-5-yl-X₃ | X₄-(CH₂)₃-N(CH₃)-CH₂CH₂-Ph | 584.4 | 8.0 |
| 270 | H₃C-CH(CH₃)-CH₂-X₁ | X₂-CH₂-CH(CH₃)-CH₃ | indan-5-yl-X₃ | X₄-(CH₂)₃-N(CH₃)-CH₂CH₂-Ph | 580.5 | 8.3 |
| 271 | H₃C-CH(CH₃)-CH₂-X₁ | X₂-CH₂-CH(CH₃)-CH₃ | 4-phenoxyphenyl-X₃ | X₄-(CH₂)₃-N(CH₃)-CH₂CH₂-Ph | 632.4 | 8.6 |
| 272 | H₃C-CH(CH₃)-CH₂-X₁ | X₂-CH₂-CH(CH₃)-CH₃ | 4-bromo-3-methylphenyl-X₃ | X₄-(CH₂)₃-N(CH₃)-CH₂CH₂-Ph | 632.4 | 8.5 |

| Examples | R1 | R2 | R3 | R4 | [M+H]⁺ | rt (min) |
|---|---|---|---|---|---|---|
| 273 | H | 4-X₂-C₆H₄-N(CH₃)CH₂CH₃ | 3-Cl-C₆H₄-X₃ | X₄-(CH₂)₄-N(CH₃)-CH₂CH₂-C₆H₅ | 609.3 | 7.0 |
| 274 | H | 4-X₂-C₆H₄-N(CH₃)CH₂CH₃ | 1-naphthyl-X₃ | X₄-(CH₂)₄-N(CH₃)-CH₂CH₂-C₆H₅ | 625.4 | 7.0 |
| 275 | H | 4-X₂-C₆H₄-N(CH₃)CH₂CH₃ | 2-OMe-4-NO₂-C₆H₃-X₃ | X₄-(CH₂)₄-N(CH₃)-CH₂CH₂-C₆H₅ | 650.4 | 7.2 |
| 276 | H | 4-X₂-C₆H₄-N(CH₃)CH₂CH₃ | 2,3-diMe-C₆H₃-X₃ | X₄-(CH₂)₄-N(CH₃)-CH₂CH₂-C₆H₅ | 603.4 | 6.9 |

| Examples | R1 | R2 | R3 | R4 | [M + H]⁺ | rt (min) |
|---|---|---|---|---|---|---|
| 277 | H | 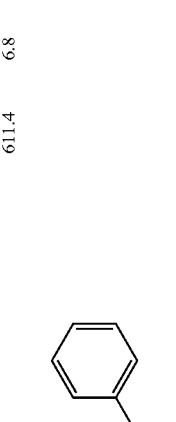 | 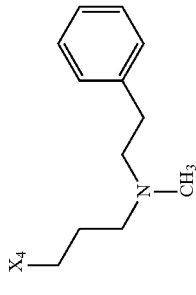 | 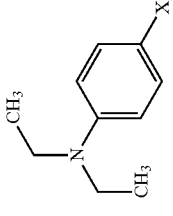 | 617.4 | 6.8 |
| 278 | H | 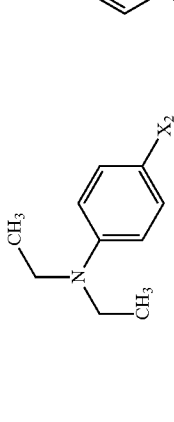 | 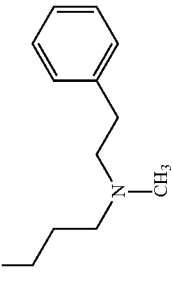 | 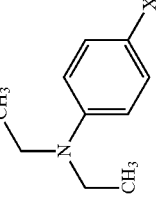 | 617.4 | 7.2 |
| 279 | H | 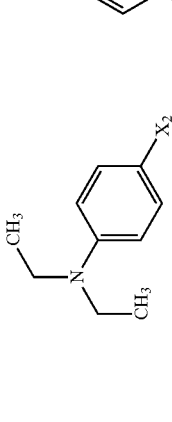 | 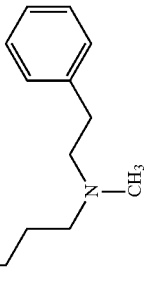 |  | 611.4 | 6.8 |
| 280 | H | 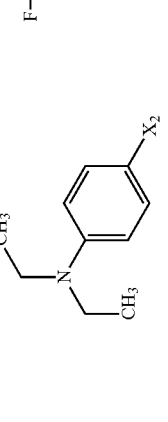 | 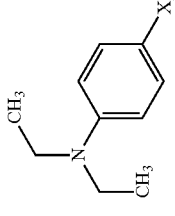 |  | 600.4 | 6.9 |

| Examples | R1 | R2 | R3 | R4 | [M + H]+ | rt (min) |
|---|---|---|---|---|---|---|
| 281 | H | | | | 619.3 | 6.7 |
| 282 | H | | | | 615.4 | 7.0 |
| 283 | H | | | | 667.4 | 7.3 |
| 284 | H | | | | 667.3 | 7.2 |

-continued

| Examples | R1 | R2 | R3 | R4 | [M + H]⁺ | rt (min) |
|---|---|---|---|---|---|---|
| 285 | H₃C-CH(CH₃)-CH₂-X₁ | X₂-CH₂-CH(CH₃)-CH₃ | 3-chlorophenyl (X₃) | 2-(pyridin-2-yl)ethyl-N(CH₃)-(CH₂)₃-X₄ | 575.4 | 7.6 |
| 286 | H₃C-CH(CH₃)-CH₂-X₁ | X₂-CH₂-CH(CH₃)-CH₃ | naphthalen-1-yl (X₃) | 2-(pyridin-2-yl)ethyl-N(CH₃)-(CH₂)₃-X₄ | 591.4 | 7.5 |
| 287 | H₃C-CH(CH₃)-CH₂-X₁ | X₂-CH₂-CH(CH₃)-CH₃ | 2-methoxy-4-nitrophenyl (X₃) | 2-(pyridin-2-yl)ethyl-N(CH₃)-(CH₂)₃-X₄ | 616.4 | 7.9 |
| 288 | H₃C-CH(CH₃)-CH₂-X₁ | X₂-CH₂-CH(CH₃)-CH₃ | 2,6-dimethylphenyl (X₃) | 2-(pyridin-2-yl)ethyl-N(CH₃)-(CH₂)₃-X₄ | 569.4 | 7.4 |

-continued

| Examples | R1 | R2 | R3 | R4 | [M+H]⁺ | rt (min) |
|---|---|---|---|---|---|---|
| 289 | H₃C-CH(CH₃)-CH₂-X₁ | X₂-CH₂-CH(CH₃)-CH₃ | 4-acetylphenyl-X₃ | 2-pyridyl-CH₂CH₂-N(CH₃)-(CH₂)₃-X₄ | 583.4 | 7.4 |
| 290 | H₃C-CH(CH₃)-CH₂-X₁ | X₂-CH₂-CH(CH₃)-CH₃ | 4-(1-hydroxyethyl)phenyl-X₃ | 2-pyridyl-CH₂CH₂-N(CH₃)-(CH₂)₃-X₄ | 583.4 | 7.8 |
| 291 | H₃C-CH(CH₃)-CH₂-X₁ | X₂-CH₂-CH(CH₃)-CH₃ | 2,6-difluorophenyl-X₃ | 2-pyridyl-CH₂CH₂-N(CH₃)-(CH₂)₃-X₄ | 577.4 | 7.4 |
| 292 | H₃C-CH(CH₃)-CH₂-X₁ | X₂-CH₂-CH(CH₃)-CH₃ | 3-cyanophenyl-X₃ | 2-pyridyl-CH₂CH₂-N(CH₃)-(CH₂)₃-X₄ | 566.4 | 7.5 |

| Examples | R1 | R2 | R3 | R4 | [M + H]⁺ | rt (min) |
|---|---|---|---|---|---|---|
| 293 | H₃C-CH(CH₃)-CH₂-X₁ | X₂-CH₂-CH(CH₃)-CH₃ | benzo[1,3]dioxol-5-yl-X₃ | 2-(pyridin-2-yl)ethyl-N(CH₃)-(CH₂)₃-X₄ | 583.3 | 7.3 |
| 294 | H₃C-CH(CH₃)-CH₂-X₁ | X₂-CH₂-CH(CH₃)-CH₃ | indan-5-yl-X₃ | 2-(pyridin-2-yl)ethyl-N(CH₃)-(CH₂)₃-X₄ | 581.4 | 7.6 |
| 295 | H₃C-CH(CH₃)-CH₂-X₁ | X₂-CH₂-CH(CH₃)-CH₃ | 4-phenoxyphenyl-X₃ | 2-(pyridin-2-yl)ethyl-N(CH₃)-(CH₂)₃-X₄ | 633.3 | 7.9 |
| 296 | H₃C-CH(CH₃)-CH₂-X₁ | X₂-CH₂-CH(CH₃)-CH₃ | 4-bromo-3-methylphenyl-X₃ | 2-(pyridin-2-yl)ethyl-N(CH₃)-(CH₂)₃-X₄ | 633.2 | 7.8 |

-continued
| Examples | R1 | R2 | R3 | R4 | [M + H]⁺ | rt (min) |
|---|---|---|---|---|---|---|
| 297 | 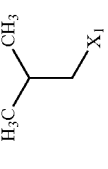 | 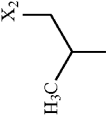 | 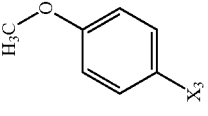 | 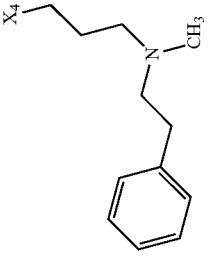 | 570.1 | 7.9 |
| 298 | 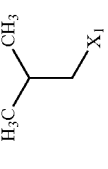 | 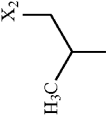 | 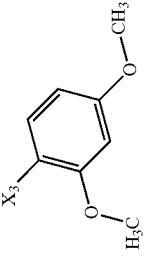 | 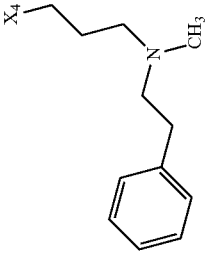 | 600.1 | 7.9 |
| 299 | 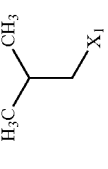 | 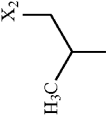 | 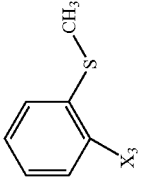 | 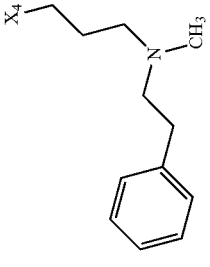 | 586.1 | 8.0 |
| 300 | 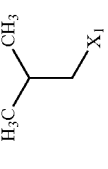 | 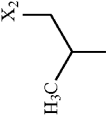 | 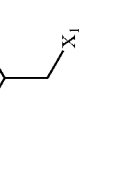 | 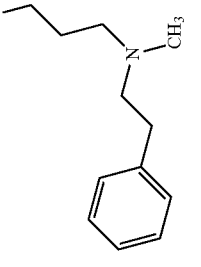 | 604.1 | 8.4 |

-continued

| Examples | R1 | R2 | R3 | R4 | [M+H]⁺ | rt (min) |
|---|---|---|---|---|---|---|
| 301 | H₃C-CH(CH₃)-CH₂-X₁ | X₂-CH₂-CH(CH₃)-CH₃ | 4-(N(CH₃)₂)-C₆H₄-X₃ | X₄-(CH₂)₃-N(CH₃)-CH₂CH₂-C₆H₅ | 583.2 | 7.9 |
| 302 | H₃C-CH(CH₃)-CH₂-X₁ | X₂-CH₂-CH(CH₃)-CH₃ | 2,5-dimethoxyphenyl-X₃ | X₄-(CH₂)₃-N(CH₃)-CH₂CH₂-C₆H₅ | 600.1 | 8.0 |
| 303 | H₃C-CH(CH₃)-CH₂-X₁ | X₂-CH₂-CH(CH₃)-CH₃ | 3-(SCH₃)-C₆H₄-X₃ | X₄-(CH₂)₃-N(CH₃)-CH₂CH₂-C₆H₅ | 586.1 | 8.3 |
| 304 | X₁-CH₂-CH(CH₃)-CH₃ | H₃C-CH(CH₃)-CH₂-X₂ | 2-(OCH₃)-C₆H₄-X₃ | X₄-(CH₂)₃-N(CH₃)-CH₂CH₂-C₆H₅ | 570.1 | 7.9 |

-continued

| Examples | R1 | R2 | R3 | R4 | [M + H]⁺ | rt (min) |
|---|---|---|---|---|---|---|
| 305 | (CH₃)₂CHCH₂-X₁ | X₂-CH₂CH(CH₃)₂ | 3-methoxyphenyl-X₃ | X₄-(CH₂)₃-N(CH₃)-CH₂CH₂-phenyl | 570.1 | 8.1 |
| 306 | (CH₃)₂CHCH₂-X₁ | X₂-CH₂CH(CH₃)₂ | 4-(2-methoxyethoxy)phenyl-X₃ | X₄-(CH₂)₃-N(CH₃)-CH₂CH₂-phenyl | 584.1 | 8.0 |
| 307 | (CH₃)₂CHCH₂-X₁ | X₂-CH₂CH(CH₃)₂ | 4-methoxyphenyl-X₃ | X₄-(CH₂)₃-N(CH₃)-CH₂CH₂-phenyl | 571.1 | 7.6 |
| 308 | X₁-CH₂CH(CH₃)₂ | CH₃CH(CH₂-X₂)- | 2,4-dimethoxyphenyl-X₃ | 2-pyridyl-CH₂CH₂-N(CH₃)-(CH₂)₃-X₄ | 601.1 | 7.6 |

-continued
| Examples | R1 | R2 | R3 | R4 | [M + H]$^+$ | rt (min) |
|---|---|---|---|---|---|---|
| 309 |  | 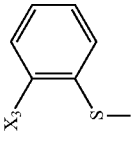 | 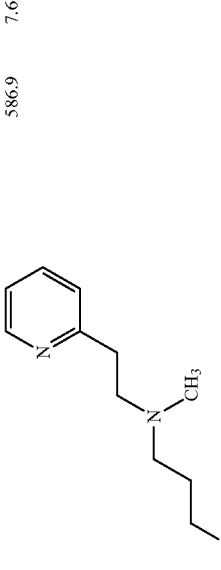 |  | 586.9 | 7.6 |
| 310 | 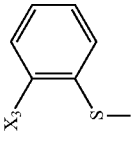 | 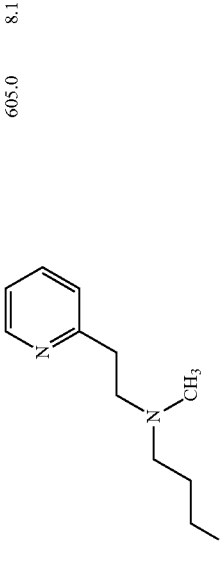 |  | 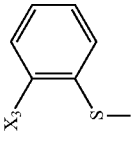 | 605.0 | 8.1 |
| 311 | 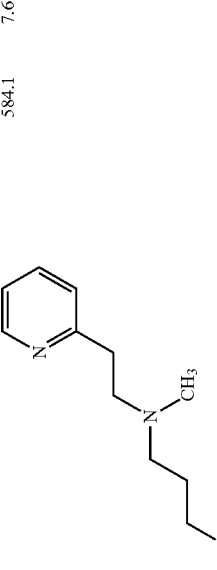 |  | 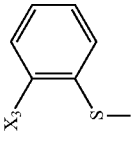 | 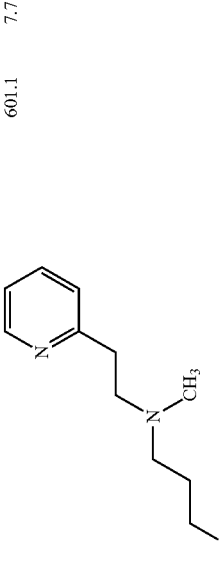 | 584.1 | 7.6 |
| 312 | | | | | 601.1 | 7.7 |

| Examples | R1 | R2 | R3 | R4 | [M+H]⁺ | rt (min) |
|---|---|---|---|---|---|---|
| 313 | H₃C-CH(CH₃)-CH₂-X₁ | X₂-CH₂-CH(CH₃)-CH₃ | 3-(SCH₃)-C₆H₄-X₃ | pyridin-2-yl-CH₂CH₂-N(CH₃)-(CH₂)₃-X₄ | 587.0 | 7.9 |
| 314 | X₁-CH₂-CH(CH₃)-CH₃ | CH₃-CH(CH₃)-CH₂-X₂ | 2-(OCH₃)-C₆H₄-X₃ | pyridin-2-yl-CH₂CH₂-N(CH₃)-(CH₂)₃-X₄ | 571.1 | 7.6 |
| 315 | H₃C-CH(CH₃)-CH₂-X₁ | X₂-CH₂-CH(CH₃)-CH₃ | 3-(OCH₃)-C₆H₄-X₃ | pyridin-2-yl-CH₂CH₂-N(CH₃)-(CH₂)₃-X₄ | 571.1 | 7.7 |
| 316 | H₃C-CH(CH₃)-CH₂-X₁ | CH₃-CH(CH₃)-CH₂-X₂ | 4-(OCH₃)-C₆H₄-O-X₃ | pyridin-2-yl-CH₂CH₂-N(CH₃)-(CH₂)₃-X₄ | 585.1 | 7.7 |

-continued
| Examples | R1 | R2 | R3 | R4 | [M + H]+ | rt (min) |
|---|---|---|---|---|---|---|
| 317 | H | 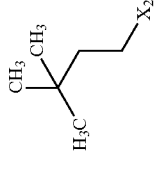 |  |  | 540.4 | 8.1 |
| 318 | |  |  |  | 593.2 | 7.4 |
| 319 | |  |  |  | 597.2 | 7.9 |
| 320 | |  |  |  | 626.2 | 8.7 |

-continued

| Examples | R1 | R2 | R3 | R4 | [M + H]⁺ | rt (min) |
|---|---|---|---|---|---|---|
| 321 | | thiolane-X₂ | 3,5-dimethylphenyl-X₃ | X₄-(CH₂)₃-N(CH₃)-CH₂CH₂-phenyl | 528.2 | 8.0 |
| 322 | H | cycloheptyl-X₂ | 3,5-dimethylphenyl-X₃ | X₄-(CH₂)₃-N(CH₂CH₃)-CH₂CH₂-phenyl | 552.2 | 8.6 |
| 323 | | piperidinyl-X₂ with C(O)N(CH₂CH₃)₂ | 3,5-dimethylphenyl-X₃ | X₄-(CH₂)₃-N(CH₂CH₃)-CH₂CH₂-phenyl | 623.3 | 8.1 |
| 324 | | piperazinyl-X₂ with 3-chlorophenyl | 3,5-dimethylphenyl-X₃ | X₄-(CH₂)₃-N(CH₂CH₃)-CH₂CH₂-phenyl | 635.2 | 8.8 |

| Examples | R1 | R2 | R3 | R4 | [M + H]⁺ | rt (min) |
|---|---|---|---|---|---|---|
| 325 | H | 4-piperidine N-C(O)OCH₂CH₃ (X₂) | 3,5-dimethylphenyl (X₃) | -(CH₂)₃-N(CH₃)-CH₂CH₂-phenyl (X₄) | 611.2 | 8.2 |
| 326 | | 4-(piperidin-1-yl)piperidine (X₂) | 3,5-dimethylphenyl (X₃) | -(CH₂)₃-N(CH₃)-CH₂CH₂-phenyl (X₄) | 607.0 | 7.6 |
| 327 | | 4-(benzo[d][1,3]dioxol-5-ylmethyl)piperazine (X₂) | 3,5-dimethylphenyl (X₃) | -(CH₂)₃-N(CH₃)-CH₂CH₂-phenyl (X₄) | 659.2 | 7.8 |

-continued

| Examples | R1 | R2 | R3 | R4 | [M + H]+ | rt (min) |
|---|---|---|---|---|---|---|
| 328 |  | X2-tetrahydroisoquinoline | X3-3,5-dimethylphenyl | X4-(CH2)3-N(CH3)-CH2CH2-phenyl | 572.2 | 8.5 |
| 329 | H | X2-CH2-pyridin-2-yl | X3-3,5-dimethylphenyl | X4-(CH2)3-N(CH3)-CH2CH2-phenyl | 547.2 | 7.7 |
| 330 |  | X2-(4-(4-methoxyphenyl)piperazin-1-yl) | X3-3,5-dimethylphenyl | X4-(CH2)3-N(CH3)-CH2CH2-phenyl | 631.2 | 8.4 |
| 331 | H | X2-(CH2)3-N(CH2CH3)2 | X3-3,5-dimethylphenyl | X4-(CH2)3-N(CH3)-CH2CH2-phenyl | 569.2 | 7.6 |

| Examples | R1 | R2 | R3 | R4 | [M + H]+ | rt (min) |
|---|---|---|---|---|---|---|
| 332 | H |  | 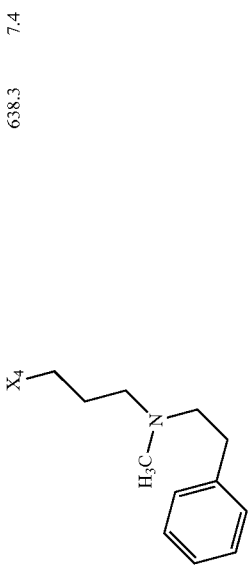 | 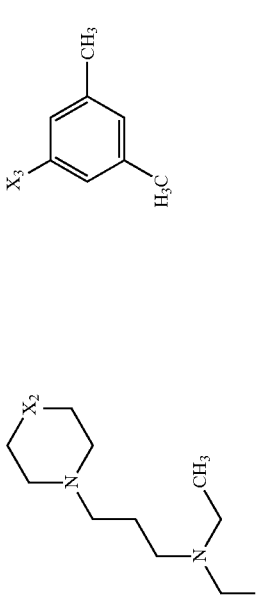 | 574.2 | 8.6 |
| 333 | | 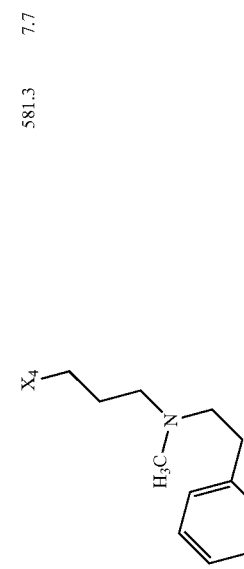 | 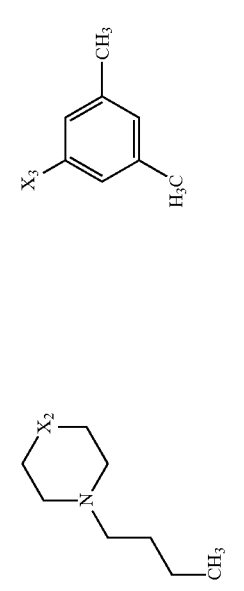 |  | 638.3 | 7.4 |
| 334 | |  |  |  | 581.3 | 7.7 |

| Examples | R1 | R2 | R3 | R4 | [M + H]+ | rt (min) |
|---|---|---|---|---|---|---|
| 335 | | X2-(piperazine)-pyrazine | 3,5-dimethylphenyl-X3 | X4-(CH2)3-N(CH3)-CH2CH2-phenyl | 603.2 | 8.0 |
| 336 | | X2-piperidine | 3,5-dimethylphenyl-X3 | X4-(CH2)3-N(CH3)-CH2CH2-phenyl | 607.3 | 7.7 |
| 337 | | X2-cycloheptyl | 3,5-dimethoxyphenyl-X3 | X4-(CH2)3-N(CH3)-CH2CH2-(2-pyridyl) | 585.2 | 8.18 |
| 338 | H | X2-piperidinyl-C(O)-N(CH2CH3)2 | 3,5-dimethoxyphenyl-X3 | X4-(CH2)3-N(CH3)-CH2CH2-(2-pyridyl) | 656.3 | 7.2 |

-continued
| Examples | R1 | R2 | R3 | R4 | [M + H]+ | rt (min) |
|---|---|---|---|---|---|---|
| 339 | |  | 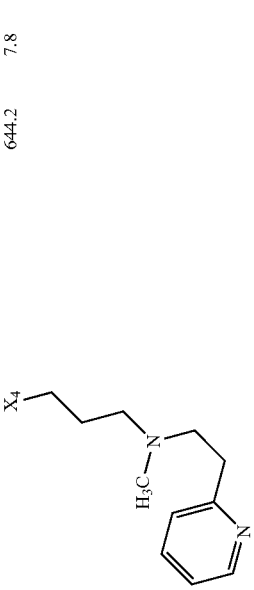 | 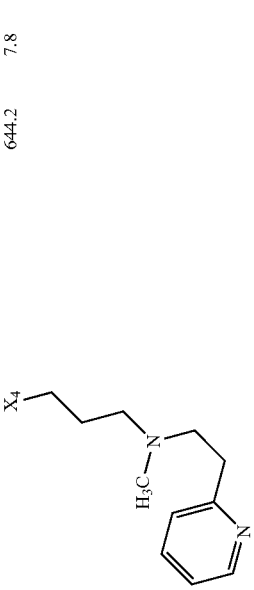 | 668.2 | 8.4 |
| 340 | H | 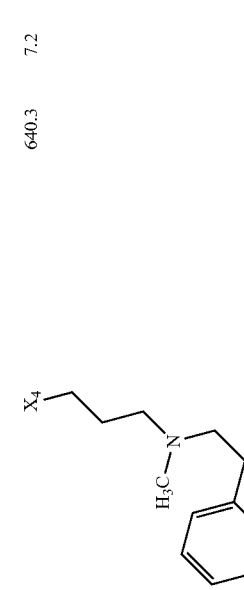 | 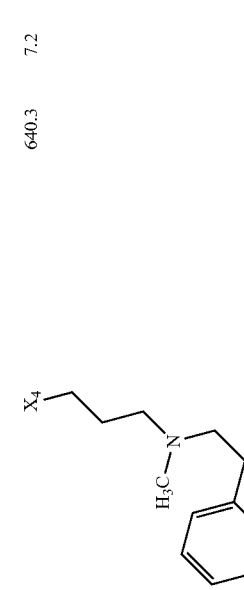 |  | 644.2 | 7.8 |
| 341 | | | | | 640.3 | 7.2 |

| Examples | R1 | R2 | R3 | R4 | [M + H]⁺ | rt (min) |
|---|---|---|---|---|---|---|
| 342 | | 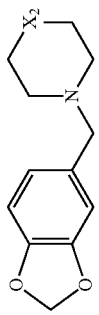 | 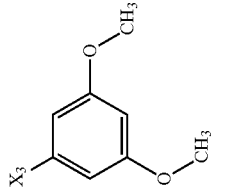 | 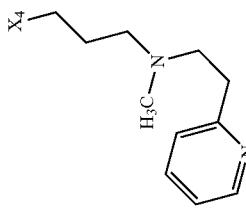 | 692.2 | 7.5 |
| 343 | | 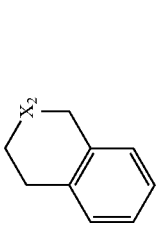 | 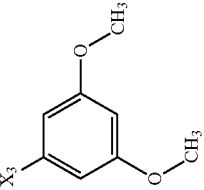 | 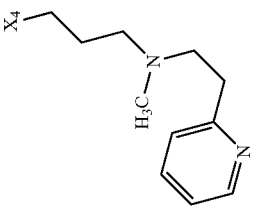 | 605.2 | 8.1 |
| 344 | H | 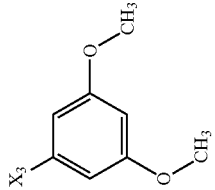 | 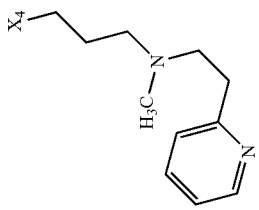 | | 580.2 | 7.3 |

-continued

| Examples | R1 | R2 | R3 | R4 | [M + H]⁺ | rt (min) |
|---|---|---|---|---|---|---|
| 345 | | | | | 664.2 | 8.0 |
| 346 | H | | | | 602.3 | 7.2 |
| 347 | H | | | | 607.2 | 8.21 |

-continued

| Examples | R1 | R2 | R3 | R4 | [M + H]⁺ | rt (min) |
|---|---|---|---|---|---|---|
| 348 | | X₂-morpholine-N-(CH₂)₃-N(CH₃)(CH₂CH₃) | 3,5-dimethoxyphenyl-X₃ | X₄-(CH₂)₃-N(CH₃)-CH₂CH₂-(2-pyridyl) | 671.3 | 7.1 |
| 349 | | X₂-morpholine-N-(CH₂)₃-CH₃ | 3,5-dimethoxyphenyl-X₃ | X₄-(CH₂)₃-N(CH₃)-CH₂CH₂-(2-pyridyl) | 614.3 | 7.3 |
| 350 | | X₂-morpholine-N-(2-pyrazinyl) | 3,5-dimethoxyphenyl-X₃ | X₄-(CH₂)₃-N(CH₃)-CH₂CH₂-(2-pyridyl) | 636.2 | 7.6 |

-continued

| Examples | R1 | R2 | R3 | R4 | [M + H]⁺ | rt (min) |
|---|---|---|---|---|---|---|
| 351 | | piperidine-X₂ on N, cyclohexyl on N | 3,5-dimethoxyphenyl-X₃ | X₄-(CH₂)₃-N(CH₃)-(CH₂)₂-(2-pyridyl) | 640.3 | 7.4 |
| 352 | | 4-methylcyclohexyl-X₂ | 3,5-dimethylphenyl-X₃ | X₄-(CH₂)₃-N(CH₃)-(CH₂)₂-(2-pyridyl) | 538.2 | 8.2 |
| 353 | H | X₂-(CH₂)₂-N(CH₂CH₃)₂ | 3,5-dimethylphenyl-X₃ | X₄-(CH₂)₃-N(CH₃)-(CH₂)₂-phenyl | 555.3 | 7.5 |
| 354 | H | X₂-(CH₂)₂-(1-methylpyrrolidin-2-yl) | 3,5-dimethylphenyl-X₃ | X₄-(CH₂)₃-N(CH₃)-(CH₂)₂-phenyl | 567.3 | 7.4 |

-continued

| Examples | R1 | R2 | R3 | R4 | [M + H]⁺ | rt (min) |
|---|---|---|---|---|---|---|
| 355 | H | (3,4-dimethoxyphenethyl)-X₂ | 3,5-dimethylphenyl-X₃ | H₃C-N(CH₂CH₂Ph)(CH₂CH₂CH₂-X₄) | 620.3 | 8.1 |
| 356 | H | (pyridin-4-ylmethyl)-X₂ | 3,5-dimethylphenyl-X₃ | H₃C-N(CH₂CH₂Ph)(CH₂CH₂CH₂-X₄) | 547.3 | 7.4 |
| 357 | H | [4-(pyridin-2-yl)piperazin-1-yl]-X₂ | 3,5-dimethylphenyl-X₃ | H₃C-N(CH₂CH₂Ph)(CH₂CH₂CH₂-X₄) | 602.3 | 7.5 |
| 358 | H | [3-(imidazol-1-yl)propyl]-X₂ | 3,5-dimethylphenyl-X₃ | H₃C-N(CH₂CH₂Ph)(CH₂CH₂CH₂-X₄) | 564.3 | 7.4 |

-continued
| Examples | R1 | R2 | R3 | R4 | [M + H]⁺ | rt (min) |
|---|---|---|---|---|---|---|
| 359 | H |  | 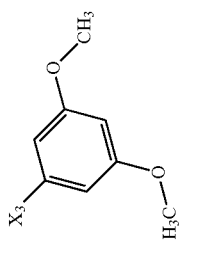 | 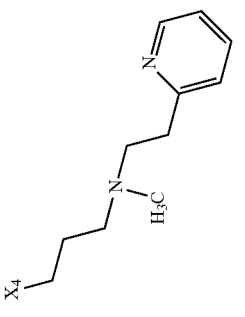 | 614.2 | 8.5 |
| 360 | H | 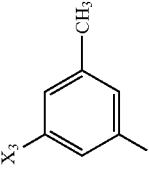 | 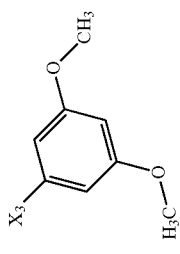 | 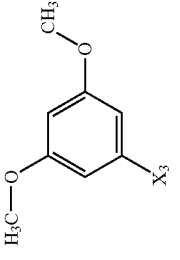 | 619.3 | 8.1 |
| 361 | | 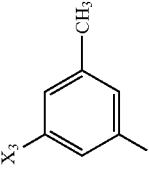 | 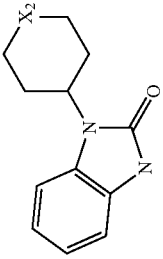 | 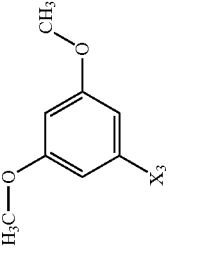 | 689.3 | 7.6 |
| 362 | | 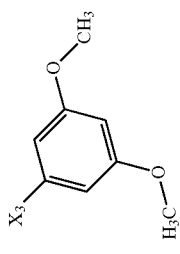 | 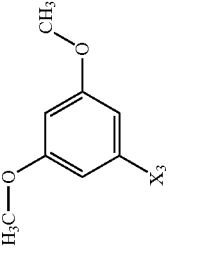 | | 652.3 | 7.5 |

-continued
| Examples | R1 | R2 | R3 | R4 | [M + H]+ | rt (min) |
|---|---|---|---|---|---|---|
| 363 | H | 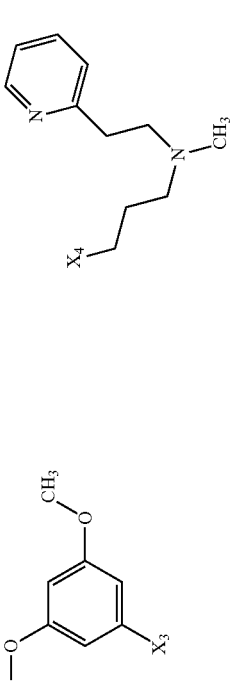 | 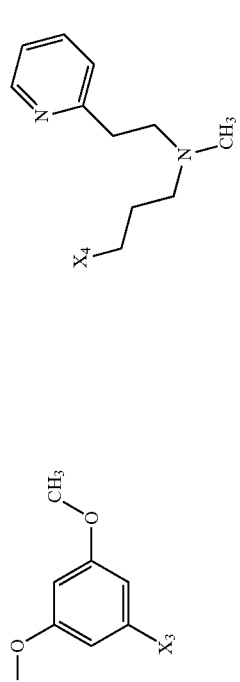 | 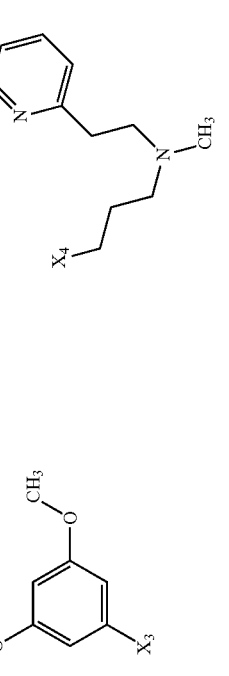 | 648.3 | 7.3 |
| 364 | H | 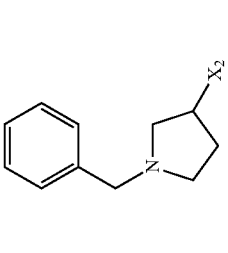 | 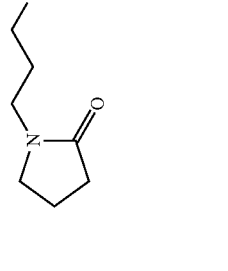 | 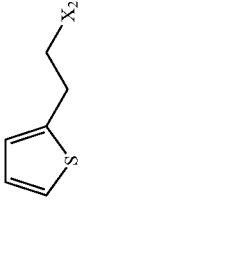 | 614.3 | 7.3 |
| 365 | H |  |  |  | 599.2 | 7.9 |
| 366 | H | 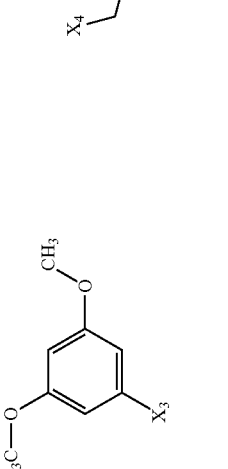 | 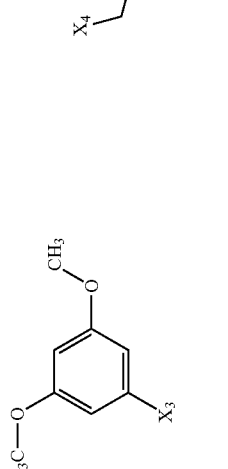 | 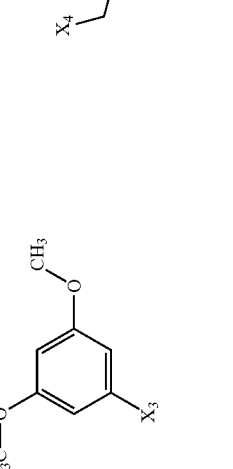 | 605.3 | 8.0 |

| Examples | R1 | R2 | R3 | R4 | [M + H]⁺ | rt (min) |
|---|---|---|---|---|---|---|
| 367 | | spiro piperidine-phenyl pyrrolidinone with X₂ | 3,5-dimethylphenyl with X₃ | N-methyl-N-phenethyl aminopropyl with X₄ | 670.4 | 8.1 |
| 368 | isobutyl with X₁ | 2-methylpropyl with X₂ | 3,4,5-trimethoxybenzyl with X₃ | N-methyl-N-(2-pyridin-2-ylethyl)aminobutyl with X₄ | 645.5 | 8.0 |
| 369 | isobutyl with X₁ | 2-methylpropyl with X₂ | 3,4-dimethoxyphenethyl with X₃ | N-methyl-N-(2-pyridin-2-ylethyl)aminobutyl with X₄ | 629.5 | 8.0 |
| 370 | isobutyl with X₁ | 2-methylpropyl with X₂ | 3,4,5-trimethoxyphenyl with X₃ | N-methyl-N-(2-pyridin-2-ylethyl)aminobutyl with X₄ | 631.3 | 7.9 |

-continued
| Examples | R1 | R2 | R3 | R4 | [M + H]⁺ | rt (min) |
|---|---|---|---|---|---|---|
| 371 |  | 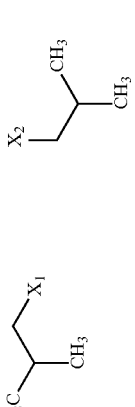 | 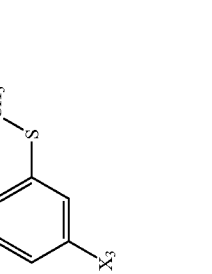 | 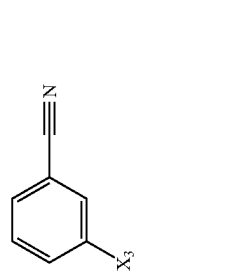 | 584.5 | 8.5 |
| 372 |  | 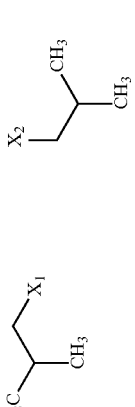 | 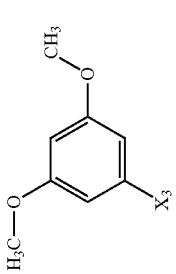 | 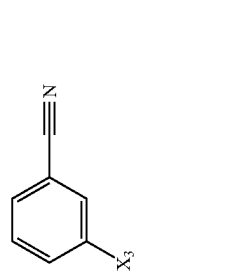 | 598.5 | 8.4 |
| 373 |  | 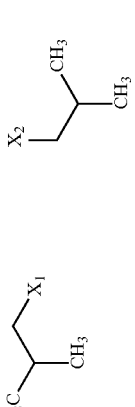 | 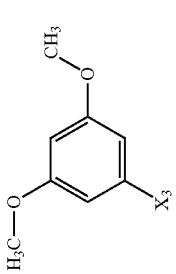 | 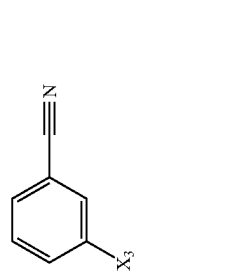 | 628.5 | 8.2 |
| 374 |  | 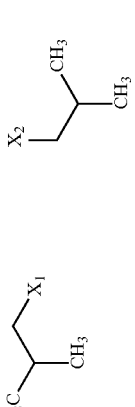 | 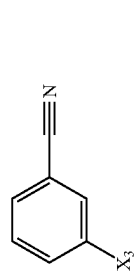 | 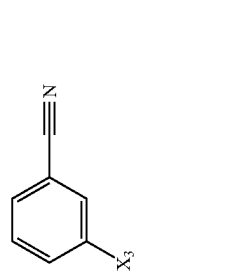 | 563.5 | 8.7 |

-continued

| Examples | R1 | R2 | R3 | R4 | [M + H]⁺ | rt (min) |
|---|---|---|---|---|---|---|
| 375 | isobutyl-X₁ | X₂-isobutyl | 3-(methylthio)phenyl-X₃ | X₄-CH₂CH₂-N-piperazine-N-benzyl | 613.5 | 8.3 |
| 376 | isobutyl-X₁ | X₂-isobutyl | 3,5-dimethoxyphenyl-X₃ | X₄-CH₂CH₂-N-piperazine-N-benzyl | 627.6 | 8.3 |
| 377 | isobutyl-X₁ | X₂-isobutyl | 3,4,5-trimethoxyphenyl-X₃ | X₄-CH₂CH₂-N-piperazine-N-benzyl | 657.6 | 8.1 |

| Examples | R1 | R2 | R3 | R4 | [M+H]+ | rt (min) |
|---|---|---|---|---|---|---|
| 378 | X₁-CH₂-CH(CH₃)-CH₃ | X₂-CH₂-CH(CH₃)-CH₃ | 3-cyanophenyl-X₃ | X₄-CH₂CH₂-N(piperazine)-N-CH₂-phenyl | 592.5 | 8.4 |
| 379 | X₁-CH₂-CH(CH₃)-CH₃ | X₂-CH₂-CH(CH₃)-CH₃ | 3-(methylthio)phenyl-X₃ | X₄-(CH₂)₃-N(CH₃)-CH₂-phenyl | 572.5 | 8.4 |
| 380 | X₁-CH₂-CH(CH₃)-CH₃ | X₂-CH₂-CH(CH₃)-CH₃ | 3,5-dimethoxyphenyl-X₃ | X₄-(CH₂)₃-N(CH₃)-CH₂-phenyl | 586.5 | 8.3 |
| 381 | X₁-CH₂-CH(CH₃)-CH₃ | X₂-CH₂-CH(CH₃)-CH₃ | 3,4,5-trimethoxyphenyl-X₃ | X₄-(CH₂)₃-N(CH₃)-CH₂-phenyl | 616.5 | 8.1 |

-continued
| Examples | R1 | R2 | R3 | R4 | [M + H]+ | rt (min) |
|---|---|---|---|---|---|---|
| 382 | 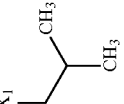 |  |  |  | 551.5 | 8.6 |
| 383 |  |  |  |  | 573.4 | 8.0 |
| 384 | 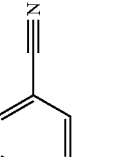 | 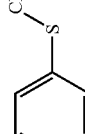 |  | 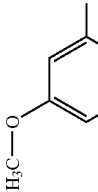 | 587.5 | 8.0 |
| 385 |  |  |  |  | 617.5 | 7.8 |

-continued
| Examples | R1 | R2 | R3 | R4 | [M + H]+ | rt (min) |
|---|---|---|---|---|---|---|
| 386 |  |  | 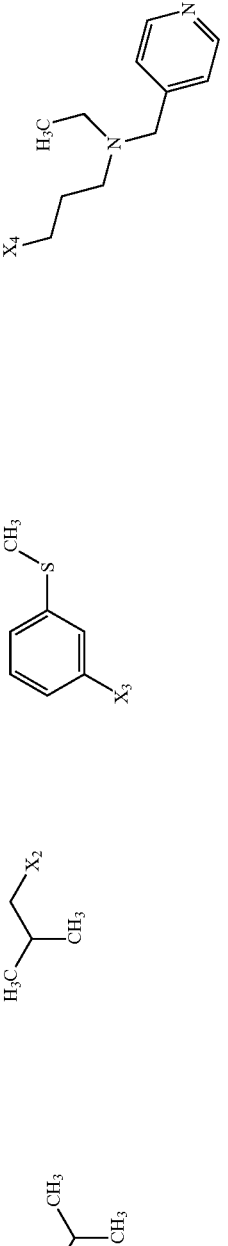 | 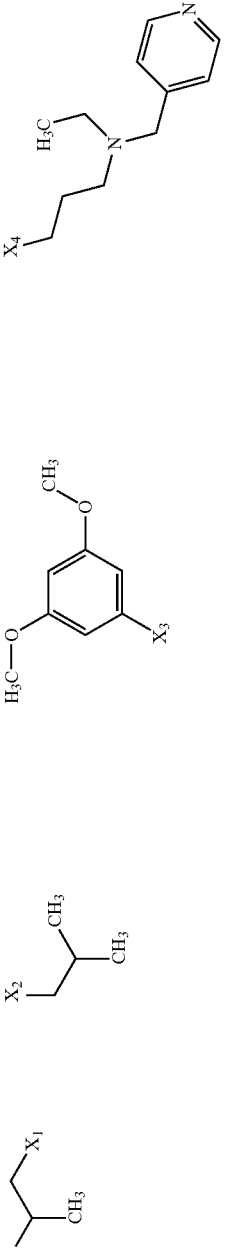 | 552.5 | 8.1 |
| 387 | 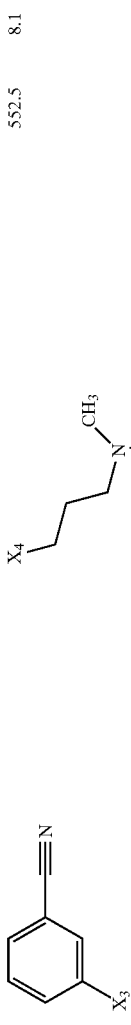 | 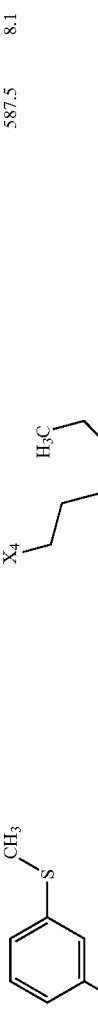 |  | 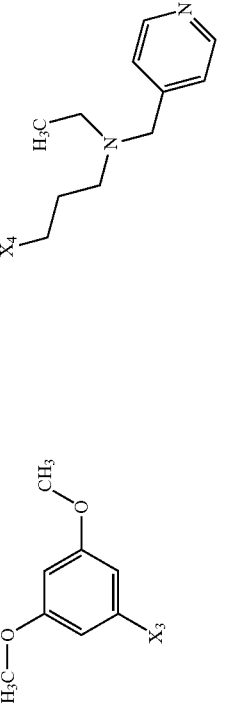 | 587.5 | 8.1 |
| 388 | 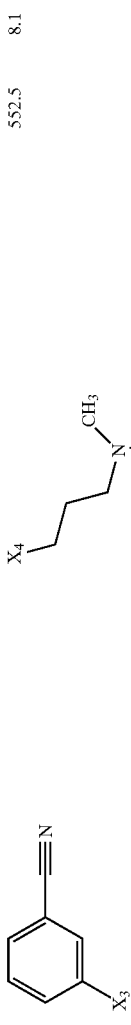 | 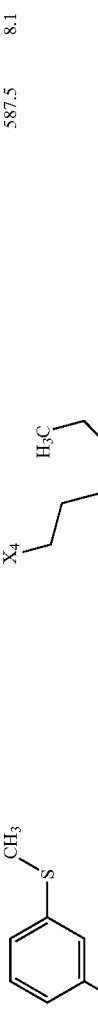 |  | 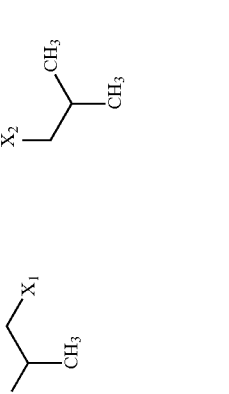 | 601.5 | 8.0 |
| 389 | 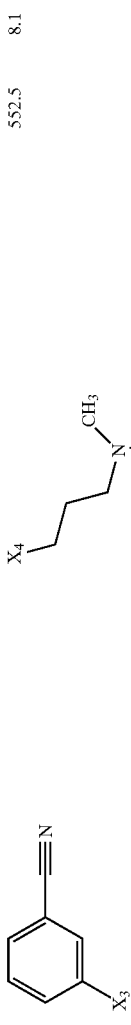 | 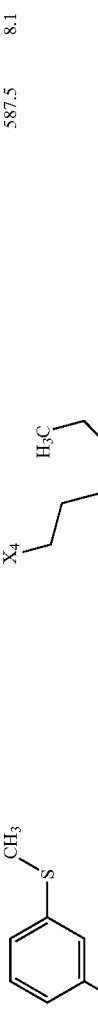 |  | 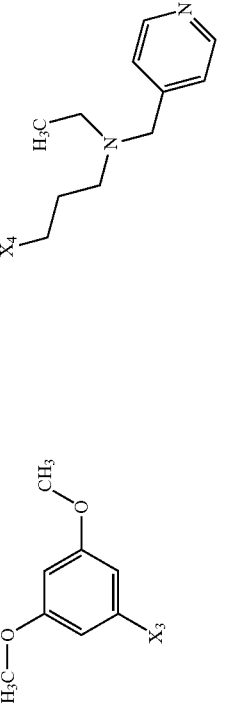 | 631.5 | 7.9 |

-continued

| Examples | R1 | R2 | R3 | R4 | [M + H]⁺ | rt (min) |
|---|---|---|---|---|---|---|
| 390 | | | | | 566.5 | 8.2 |
| 391 | | | | | 599.4 | 8.9 |
| 392 | | | | | 626.4 | 9.3 |
| 393 | | | | | 598.3 | 9.0 |

| Examples | R1 | R2 | R3 | R4 | [M+H]+ | rt (min) |
|---|---|---|---|---|---|---|
| 394 | isobutyl-X1 | X2-isobutyl | 2-Cl-4-X2-5-OCH3-phenyl-OCH3 | X4-(CH2)3-N(CH3)-CH2CH2-(2-pyridyl) | 635.5 | 8.1 |
| 395 | isobutyl-X1 | X2-isobutyl | X3-benzodioxane | X4-(CH2)3-N(CH3)-CH2CH2-(2-pyridyl) | 599.4 | 7.9 |
| 396 | isobutyl-X1 | X2-isobutyl | 2-OCH3-4-X2-5-OCH3-Cl-phenyl | X4-(CH2)3-N(CH3)-CH2CH2-(2-pyridyl) | 635.4 | 8.0 |
| 397 | X1-isobutyl | isobutyl-X2 | X3-C(O)-2-Cl-phenyl | X4-(CH2)3-N(CH3)-CH2CH2-(2-pyridyl) | 603.4 | 8.9 |

| Examples | R1 | R2 | R3 | R4 | [M + H]+ | rt (min) |
|---|---|---|---|---|---|---|
| 398 | H3C-CH(CH3)-X1 | H3C-CH(CH3)-X1 | X3-C(O)-(3-Cl-C6H4) | X4-(CH2)3-N(CH3)-CH2CH2-(2-pyridyl) | 603.4 | 9.3 |
| 399 | H3C-CH(CH3)-X1 | X2-CH2-CH(CH3)- | X3-C(O)-(4-Cl-C6H4) | X4-(CH2)3-N(CH3)-CH2CH2-(2-pyridyl) | 603.4 | 9.3 |
| 400 | H3C-CH(CH3)-X1 | X2-CH2-CH(CH3)- | X3-C(O)-(4-NO2-C6H4) | X4-(CH2)3-N(CH3)-CH2CH2-(2-pyridyl) | 614.4 | 9.1 |
| 401 | H3C-CH(CH3)-X1 | X2-CH2-CH(CH3)- | X3-C(O)-(2-CH3-C6H4) | X4-(CH2)3-N(CH3)-CH2CH2-(2-pyridyl) | 583.5 | 8.9 |

-continued
| Examples | R1 | R2 | R3 | R4 | [M + H]⁺ | rt (min) |
|---|---|---|---|---|---|---|
| 402 |  |  |  |  | 583.5 | 9.1 |
| 403 |  |  |  |  | 583.5 | 9.1 |
| 404 |  |  |  |  | 569.4 | 8.9 |
| 405 |  |  |  |  | 556.4 | 7.6 |

-continued

| Examples | R1 | R2 | R3 | R4 | [M + H]+ | rt (min) |
|---|---|---|---|---|---|---|
| 406 | isobutyl-X1 | H3C-CH(CH3)-CH2-X2 | 3,4-dimethoxyphenyl-X3 | X4-(CH2)3-N(CH3)-CH2CH2-(2-pyridyl) | 601.4 | 7.8 |
| 407 | isobutyl-X1 | X2-CH2-CH(CH3)-CH3 | 3,4,5-trimethoxybenzoyl-X3 | X4-(CH2)3-N(CH3)-CH2CH2-(2-pyridyl) | 659.5 | 8.8 |
| 408 | X1-CH2-CH(CH3)-CH3 | X2-CH2-CH(CH3)-CH3 | 3,5-dimethoxyphenyl-X3 | X4-piperidin-4-yl | 508.4 | 7.9 |
| 409 | isobutyl-X1 | X2-CH2-CH(CH3)-CH3 | 3,4,5-trimethoxyphenyl-X3 | X4-piperidin-4-yl | 538.4 | 7.8 |
| 410 | isobutyl-X1 | X2-CH2-CH(CH3)-CH3 | 3,5-dimethoxyphenyl-X3 | X4-CH2CH2-piperazinyl | 537.4 | 7.9 |

-continued

| Examples | R1 | R2 | R3 | R4 | [M + H]⁺ | rt (min) |
|---|---|---|---|---|---|---|
| 411 | X₁-CH(CH₃)-CH₃ | H₃C-CH(CH₃)-CH₂-X₂ | 3,4,5-trimethoxyphenyl-X₃ | X₄-CH₂CH₂-piperazinyl | 567.4 | 7.8 |
| 412 | X₁-CH(CH₃)-CH₃ | H₃C-CH(CH₃)-CH₂-X₂ | 3-aminomethylphenyl-X₃ (NH₂) | X₄-CH₂CH₂-piperazinyl | 506.4 | 7.3 |
| 413 | H₃C-CH(CH₃)-CH₂-X₁ | X₂-CH₂-CH(CH₃)-CH₃ | 3,5-dimethoxyphenyl-X₃ | X₄-(CH₂)₃-N(H)CH₃ | 496.4 | 7.9 |
| 414 | X₁-CH(CH₃)-CH₃ | H₃C-CH(CH₃)-CH₂-X₂ | 3,4,5-trimethoxyphenyl-X₃ | X₄-(CH₂)₃-N(H)CH₃ | 526.4 | 7.8 |
| 415 | X₁-CH(CH₃)-CH₃ | H₃C-CH(CH₃)-CH₂-X₂ | 3-aminomethylphenyl-X₃ (NH₂) | X₄-(CH₂)₃-N(H)CH₃ | 465.4 | 7.3 |

| Examples | R1 | R2 | R3 | R4 | [M + H]⁺ | rt (min) |
|---|---|---|---|---|---|---|
| 416 | 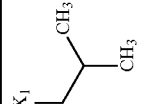 | 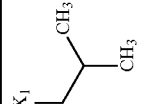 | 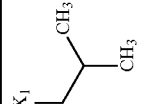 | 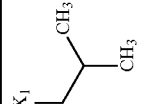 | 498.3 | 7.7 |
| 417 | 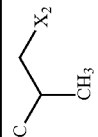 | 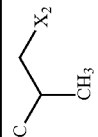 | 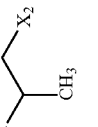 | 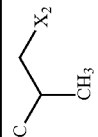 | 526.3 | 7.8 |
| 418 | 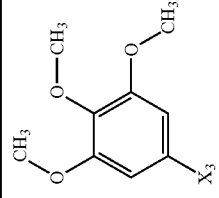 | 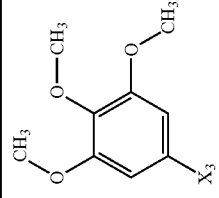 | 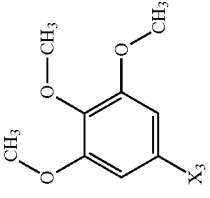 | 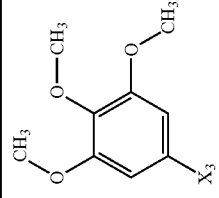 | 631.4 | 7.5 |
| 419 | 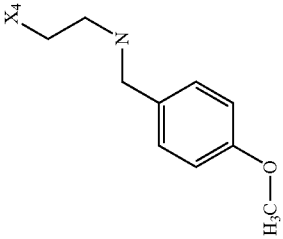 | 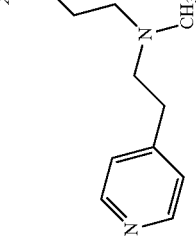 | 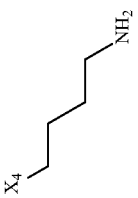 | 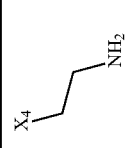 | 618.5 | 8.2 |

-continued
| Examples | R1 | R2 | R3 | R4 | [M + H]⁺ | rt (min) |
|---|---|---|---|---|---|---|
| 420 |  |  | 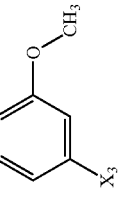 |  | 594.4 | 8.1 |
| 421 |  |  | 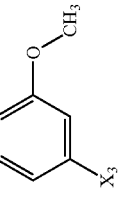 |  | 594.5 | 8.3 |
| 422 |  |  | 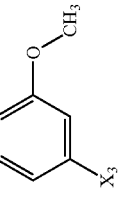 |  | 589.4 | 7.8 |
| 423 |  |  | 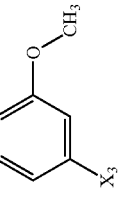 |  | 588.4 | 8.2 |

-continued

| Examples | R1 | R2 | R3 | R4 | [M + H]⁺ | rt (min) |
|---|---|---|---|---|---|---|
| 424 | | | | | 632.4 | 8.2 |
| 425 | | | | | 568.4 | 8.1 |
| 426 | | | | | 631.5 | 8.2 |
| 427 | | | | | 580.5 | 8.2 |

| Examples | R1 | R2 | R3 | R4 | [M + H]+ | rt (min) |
|---|---|---|---|---|---|---|
| 428 |  | 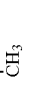 |  |  | 596.5 | 8.0 |
| 429 | 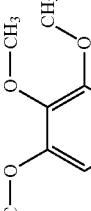 |  |  |  | 659.6 | 8.1 |
| 430 |  |  |  |  | 655.5 | 8.1 |

| Examples | R1 | R2 | R3 | R4 | [M + H]+ | rt (min) |
|---|---|---|---|---|---|---|
| 431 | (isobutyl-X1) | (isobutyl-X2) | 3,4,5-trimethoxyphenyl-X3 | X4-(CH2)4-N(CH2-cyclopentyl) | 608.6 | 8.1 |
| 432 | (isobutyl-X1) | (isobutyl-X2) | 3,4,5-trimethoxyphenyl-X3 | X4-CH2-CH2-N-CH2-CH(OH)-phenyl | 618.5 | 8.1 |
| 433 | (isobutyl-X1) | (isobutyl-X2) | 3,4,5-trimethoxyphenyl-X3 | X4-CH2-CH2-N-CH2-CH(OH)-CH2OH | 572.4 | 7.7 |
| 434 | (isobutyl-X1) | (isobutyl-X2) | 3,4,5-trimethoxyphenyl-X3 | X4-CH2-CH2-N-CH2-CH(OH)-CH2-O-phenyl | 648.5 | 8.3 |

-continued

| Examples | R1 | R2 | R3 | R4 | [M+H]⁺ | rt (min) |
|---|---|---|---|---|---|---|
| 435 | isobutyl-X₁ | X₂-isobutyl | 3,4,5-trimethoxyphenyl-X₃ | X₄-CH₂CH₂-N(CH₂CH(OH)CH₂-O-CH₂-furan) | 652.5 | 8.1 |
| 436 | isobutyl-X₁ | X₂-isobutyl | 3,4,5-trimethoxyphenyl-X₃ | X₄-(CH₂)₄-N-benzyl | 616.4 | 8.0 |
| 437 | isobutyl-X₁ | X₂-isobutyl | 3,4,5-trimethoxyphenyl-X₃ | X₄-(CH₂)₄-N-benzyl | 644.4 | 8.2 |

-continued

| Examples | R1 | R2 | R3 | R4 | [M + H]+ | rt (min) |
|---|---|---|---|---|---|---|
| 438 | H3C-CH(CH3)-CH2-X1 | X2-CH2-CH(CH3)-CH3 | 3,4,5-trimethoxyphenyl-X3 | X4-(CH2)4-N(H)-CH2-(2-chlorophenyl) | 650.4 | 8.1 |
| 439 | H3C-CH(CH3)-CH2-X1 | X2-CH2-CH(CH3)-CH3 | 3,4,5-trimethoxyphenyl-X3 | X4-(CH2)4-N(H)-CH2-(3-cyanophenyl) | 641.4 | 8.0 |
| 440 | H3C-CH(CH3)-CH2-X1 | X2-CH2-CH(CH3)-CH3 | 3,4,5-trimethoxyphenyl-X3 | X4-(CH2)4-N(H)-CH2-(4-bromophenyl) | 694.3 | 8.2 |

-continued

| Examples | R1 | R2 | R3 | R4 | [M + H]⁺ | rt (min) |
|---|---|---|---|---|---|---|
| 441 | H₃C-CH(CH₃)-CH₂-X₁ | X₂-CH₂-CH(CH₃)-CH₃ | 3,4,5-trimethoxyphenyl-X₃ | X₄-(CH₂)₄-N(H)-CH₂-(2-thienyl) | 622.3 | 8.0 |
| 442 | H₃C-CH(CH₃)-CH₂-X₁ | X₂-CH₂-CH(CH₃)-CH₃ | 3,4,5-trimethoxyphenyl-X₃ | X₄-(CH₂)₄-N(H)-CH₂-cyclohexyl | 622.5 | 8.2 |
| 443 | H₃C-CH(CH₃)-CH₂-X₁ | X₂-CH₂-CH(CH₃)-CH₃ | 3,4,5-trimethoxyphenyl-X₃ | X₄-(CH₂)₄-N(H)-(CH₂)₃-CH₃ | 582.4 | 8.0 |

-continued

| Examples | R1 | R2 | R3 | R4 | [M + H]⁺ | rt (min) |
|---|---|---|---|---|---|---|
| 444 | (isobutyl-X₁) | (isobutyl-X₂) | 3,4,5-trimethoxyphenyl-X₃ | X₄-(CH₂)₄-N(CH₂CH₂CH₃)- (butyl chain to N with propyl) | 624.4 | 8.3 |
| 445 | (isobutyl-X₁) | (isobutyl-X₂) | 3,4,5-trimethoxyphenyl-X₃ | X₄-(CH₂)₃-NH-C(=O)-O-C(CH₃)₃ | 612.4 | 9.2 |
| 446 | (isobutyl-X₁) | (isobutyl-X₂) | 3,4,5-trimethoxyphenyl-X₃ | X₄-(CH₂)₃-NH₂ | 512.2 | 7.7 |
| 447 | (isobutyl-X₁) | (isobutyl-X₂) | 3,4,5-trimethoxyphenyl-X₃ | X₄-(CH₂)₃-N(H)-CH₂-C₆H₅ | 602.4 | 8.0 |

-continued
| Examples | R1 | R2 | R3 | R4 | [M + H]⁺ | rt (min) |
|---|---|---|---|---|---|---|
| 448 | 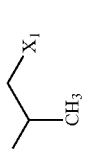 | 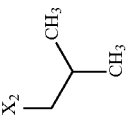 | 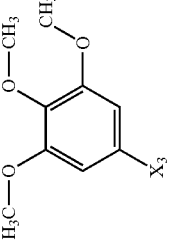 | 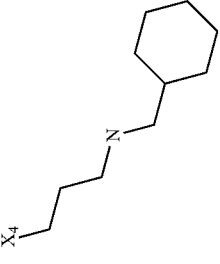 | 608.4 | 8.1 |
| 449 | 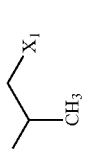 | 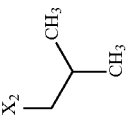 | 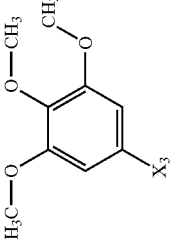 | 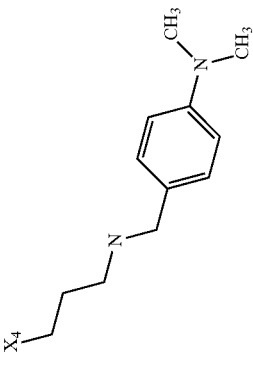 | 645.4 | 8.0 |
| 450 | 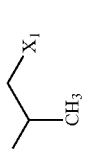 | 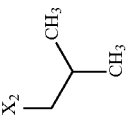 | 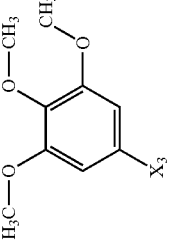 | 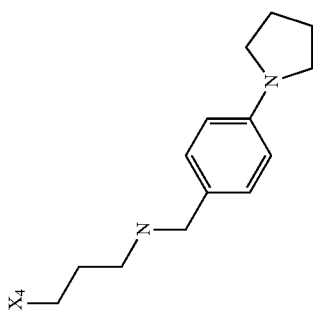 | 671.5 | 8.3 |

-continued

| Examples | R1 | R2 | R3 | R4 | [M + H]⁺ | rt (min) |
|---|---|---|---|---|---|---|
| 451 | *isobutyl-X₁* | *X₂-CH(CH₃)-CH(CH₃)-* | 3,4,5-trimethoxyphenyl-X₃ | X₄-(CH₂)₃-N(CH₂-)-[4-(N,N-diethylamino)-2-hydroxyphenyl] | 687.5 | 8.3 |
| 452 | *isobutyl-X₁* | *X₂-CH₂-CH(CH₃)-* | 3,5-dimethoxyphenyl-X₃ | X₄-(CH₂)₃-NH-CH₂-C(CH₃)₃ | 552.3 | 8.3 |
| 453 | *isobutyl-X₁* | *X₂-CH₂-CH(CH₃)-* | 3,4-dimethoxyphenyl-X₃ | X₄-(CH₂)₃-NH-CH₂-C(CH₃)₃ | 552.3 | 8.0 |
| 454 | *isobutyl-X₁* | *X₂-CH₂-CH(CH₃)-* | 3-(methylthio)phenyl-X₃ | X₄-(CH₂)₃-NH-CH₂-C(CH₃)₃ | 538.3 | 8.4 |

| Examples | R1 | R2 | R3 | R4 | [M+H]+ | rt (min) |
|---|---|---|---|---|---|---|
| 455 | H3C-CH(CH3)-CH2-X1 | X2-CH2-CH(CH3)-CH3 | 3,4-dichlorophenyl-X3 | X4-(CH2)3-NH-CH2-C(CH3)3 | 560.2 | 9.1 |
| 456 | H3C-CH(CH3)-CH2-X1 | X2-CH2-CH(CH3)-CH3 | 3,4,5-trimethoxyphenyl-X3 | X4-(CH2)3-NH-CH2-cyclopentyl | 594.4 | 8.1 |
| 457 | H3C-CH(CH3)-CH2-X1 | X2-CH2-CH(CH3)-CH3 | 3,4,5-trimethoxyphenyl-X3 | X4-(CH2)4-NH-CH2-(4-(OC(CH3)2CH3)phenyl) | 674.5 | 8.4 |
| 458 | H3C-CH(CH3)-CH2-X1 | X2-CH2-CH(CH3)-CH3 | 3,4,5-trimethoxyphenyl-X3 | X4-(CH2)3-NH-CH2-(2-pyridyl) | 603.4 | 7.9 |

| Examples | R1 | R2 | R3 | R4 | [M + H]⁺ | rt (min) |
|---|---|---|---|---|---|---|
| 459 | (isobutyl-X₁) | (isobutyl-X₂) | 3,4,5-trimethoxyphenyl-X₃ | X₄-(CH₂)₃-NH-CH₂-(pyridin-3-yl) | 603.4 | 7.8 |
| 460 | (isobutyl-X₁) | (isobutyl-X₂) | 3,4,5-trimethoxyphenyl-X₃ | X₄-(CH₂)₃-NH-CH₂-(pyridin-4-yl) | 603.4 | 7.7 |
| 461 | (isobutyl-X₁) | (isobutyl-X₂) | 3,4,5-trimethoxyphenyl-X₃ | X₄-(CH₂)₃-NH-CH₂CH₃ | 554.4 | 7.9 |
| 462 | (isobutyl-X₁) | (isobutyl-X₂) | 3,4,5-trimethoxyphenyl-X₃ | X₄-(CH₂)₃-NH-(CH₂)₂-CH₃ | 568.4 | 8.0 |

-continued

| Examples | R1 | R2 | R3 | R4 | [M + H]⁺ | rt (min) |
|---|---|---|---|---|---|---|
| 463 | H₃C-CH(CH₃)-CH₂-X₁ | H₃C-CH(CH₃)-CH₂-X₂ | 3,4,5-trimethoxyphenyl-X₃ | X₄-CH₂CH₂CH₂-NH-CH₂CH₂CH₂-S-CH₃ | 600.3 | 8.0 |
| 464 | H₃C-CH(CH₃)-CH₂-X₁ | H₃C-CH(CH₃)-CH₂-X₂ | 3,4,5-trimethoxyphenyl-X₃ | X₄-CH₂CH₂CH₂-NH-CH₂CH₂-CH(CH₃)-CH₃ | 582.4 | 8.1 |
| 465 | H₃C-CH(CH₃)-CH₂-X₁ | H₃C-CH(CH₃)-CH₂-X₂ | 3,4,5-trimethoxyphenyl-X₃ | X₄-CH₂CH₂CH₂-NH-CH₂CH₂-C(CH₃)₂-CH₃ | 596.4 | 8.2 |
| 466 | H₃C-CH(CH₃)-CH₂-X₁ | H₃C-CH(CH₃)-CH₂-X₂ | 3,4,5-trimethoxyphenyl-X₃ | X₄-CH₂CH₂CH₂-NH-CH₂-C(CH₃)(Cl)-CH₃ | 582.4 | 8.1 |

| Examples | R1 | R2 | R3 | R4 | [M + H]+ | rt (min) |
|---|---|---|---|---|---|---|
| 467 | H3C-CH(CH3)-CH2-X1 | H3C-CH(CH3)-CH2-X2 | 3,4,5-trimethoxyphenyl-X3 | X4-(CH2)3-NH-CH2-cyclopropyl | 566.3 | 7.9 |
| 468 | H3C-CH(CH3)-CH2-X1 | H3C-CH(CH3)-CH2-X2 | 3,4,5-trimethoxyphenyl-X3 | X4-(CH2)3-NH-CH2-(cyclohex-3-enyl) | 606.4 | 8.2 |
| 469 | H3C-CH(CH3)-CH2-X1 | H3C-CH(CH3)-CH2-X2 | 3,4,5-trimethoxyphenyl-X3 | X4-(CH2)3-NH-CH2-CH(CH3)-CH2-CH3 | 582.4 | 8.1 |
| 470 | H3C-CH(CH3)-CH2-X1 | H3C-CH(CH3)-CH2-X2 | 3,4,5-trimethoxyphenyl-X3 | X4-(CH2)3-NH-CH2-CH(CH2CH3)-CH2-CH3 | 596.4 | 8.2 |

-continued
| Examples | R1 | R2 | R3 | R4 | [M+H]+ | rt (min) |
|---|---|---|---|---|---|---|
| 471 |  |  | 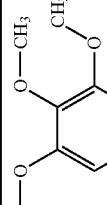 |  | 0.0 | 0.0 |
| 472 |  |  | 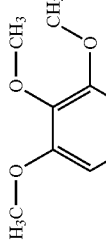 |  | 568.4 | 8.0 |
| 473 |  |  | 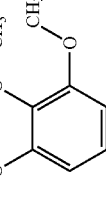 |  | 582.3 | 7.8 |
| 474 |  |  | 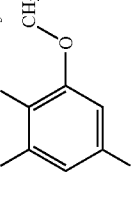 |  | 595.4 | 7.8 |

-continued

| Examples | R1 | R2 | R3 | R4 | [M + H]⁺ | rt (min) |
|---|---|---|---|---|---|---|
| 475 | H₃C-CH(CH₃)-CH₂-X₁ | H₃C-CH(CH₃)-CH₂-X₂ | 3,4,5-trimethoxyphenyl-X₃ | X₄-(CH₂)₃-(2-methylpiperidin-1-yl) | 594.4 | 7.9 |
| 476 | H₃C-CH(CH₃)-CH₂-X₁ | H₃C-CH(CH₃)-CH₂-X₂ | 3,4,5-trimethoxyphenyl-X₃ | X₄-(CH₂)₃-(pyrrolidin-1-yl) | 566.3 | 7.8 |
| 477 | H₃C-CH(CH₃)-CH₂-X₁ | H₃C-CH(CH₃)-CH₂-X₂ | 3,4,5-trimethoxyphenyl-X₃ | X₄-(CH₂)₃-NH-cyclohexyl | 580.3 | 7.9 |
| 478 | H₃C-CH(CH₃)-CH₂-X₁ | H₃C-CH(CH₃)-CH₂-X₂ | 3,4,5-trimethoxyphenyl-X₃ | X₄-(CH₂)₃-NH-cyclohexyl | 594.4 | 8.1 |

| Examples | R1 | R2 | R3 | R4 | [M + H]+ | rt (min) |
|---|---|---|---|---|---|---|
| 479 | | | | | 612.4 | 8.0 |
| 480 | | | | | 616.4 | 8.2 |
| 481 | | | | | 618.4 | 7.9 |

-continued

| Examples | R1 | R2 | R3 | R4 | [M+H]⁺ | rt (min) |
|---|---|---|---|---|---|---|
| 482 | H₃C-CH(CH₃)-CH₂-X₁ | H₃C-CH(CH₃)-CH₂-X₂ | 3,4,5-trimethoxyphenyl-X₃ | X₄-(CH₂)₃-NH-CH₂-(4-methoxyphenyl) | 632.4 | 8.1 |
| 483 | H₃C-CH(CH₃)-CH₂-X₁ | H₃C-CH(CH₃)-CH₂-X₂ | 3,4,5-trimethoxyphenyl-X₃ | X₄-(CH₂)₃-NH-CH₂-(4-bromophenyl) | 680.3 | 8.3 |
| 484 | H₃C-CH(CH₃)-CH₂-X₁ | H₃C-CH(CH₃)-CH₂-X₂ | 3,4,5-trimethoxyphenyl-X₃ | X₄-(CH₂)₃-NH-CH₂-(3,4,5-trimethoxyphenyl) | 692.4 | 8.1 |

-continued

| Examples | R1 | R2 | R3 | R4 | [M+H]+ | rt (min) |
|---|---|---|---|---|---|---|
| 485 | H3C-CH(CH3)-CH2-X1 | X2-CH2-CH(CH3)-CH3 | 3,4,5-trimethoxyphenyl-X3 | X4-(CH2)3-NH-CH2-C(CH3)=CH-CH3 | 580.3 | 8.1 |
| 486 | H3C-CH(CH3)-CH2-X1 | X2-CH2-CH(CH3)-CH3 | 3,4,5-trimethoxyphenyl-X3 | X4-(CH2)3-NH-CH2-(benzo[1,3]dioxol-5-yl) | 646.4 | 8.1 |
| 487 | H3C-CH(CH3)-CH2-X1 | X2-CH2-CH(CH3)-CH3 | 3,4,5-trimethoxyphenyl-X3 | X4-(CH2)3-NH-CH2-(3,4-dimethoxyphenyl) | 662.4 | 8.0 |

-continued

| Examples | R1 | R2 | R3 | R4 | [M + H]⁺ | rt (min) |
|---|---|---|---|---|---|---|
| 488 | | | | | 658.5 | 8.5 |
| 489 | | | | | 659.4 | 7.9 |
| 490 | | | | | 627.4 | 8.1 |

-continued

| Examples | R1 | R2 | R3 | R4 | [M + H]+ | rt (min) |
|---|---|---|---|---|---|---|
| 491 | H3C-CH(CH3)-CH2-X1 | X2-CH2-CH(CH3)-CH3 | 3,4,5-trimethoxyphenyl-X3 | X4-(CH2)3-NH-CH2-(cyclopropyl-COOCH2CH3) | 638.4 | 8.0 |
| 492 | H3C-CH(CH3)-CH2-X1 | X2-CH2-CH(CH3)-CH3 | 3,4,5-trimethoxyphenyl-X3 | X4-(CH2)3-NH-(CH2)2-CH=CH2 | 580.4 | 8.0 |
| 493 | H3C-CH(CH3)-CH2-X1 | X2-CH2-CH(CH3)-CH3 | 3,4,5-trimethoxyphenyl-X3 | X4-(CH2)3-NH-CH2-C(CH3)2-S-S-CH3 | 646.4 | 8.2 |

-continued

| Examples | R1 | R2 | R3 | R4 | [M + H]⁺ | rt (min) |
|---|---|---|---|---|---|---|
| 494 | H₃C-CH(CH₃)-CH₂-X₁ | X₂-CH₂-CH(CH₃)-CH₃ | 3,4,5-trimethoxyphenyl-X₃ | X₄-(CH₂)₃-NH-CH(CH₃)-CH₂-C(CH₃)₃ | 638.5 | 8.7 |
| 495 | H₃C-CH(CH₃)-CH₂-X₁ | X₂-CH₂-CH(CH₃)-CH₃ | 3,4,5-trimethoxyphenyl-X₃ | X₄-(CH₂)₃-NH-CH(CH₃)-SCH₃ | 614.4 | 8.1 |
| 496 | H₃C-CH(CH₃)-CH₂-X₁ | X₂-CH₂-CH(CH₃)-CH₃ | 3,4,5-trimethoxyphenyl-X₃ | X₄-(CH₂)₃-NH-CH₂-(2-naphthyl) | 652.4 | 8.3 |

-continued

| Examples | R1 | R2 | R3 | R4 | [M + H]+ | rt (min) |
|---|---|---|---|---|---|---|
| 497 | H3C-CH(CH3)-CH2-X1 | H3C-CH(CH3)-CH2-X2 | 3,4,5-trimethoxyphenyl-X3 | X4-(CH2)3-NH-CH2-(4-chlorophenyl) | 636.4 | 8.2 |
| 498 | H3C-CH(CH3)-CH2-X1 | H3C-CH(CH3)-CH2-X2 | 3,4,5-trimethoxyphenyl-X3 | X4-(CH2)3-NH-CH2-(2,5-dimethylphenyl) | 630.4 | 8.3 |
| 499 | H3C-CH(CH3)-CH2-X1 | H3C-CH(CH3)-CH2-X2 | 3,4,5-trimethoxyphenyl-X3 | X4-(CH2)3-NH-CH2-(2,3-dihydro-1,4-benzodioxin-6-yl) | 660.4 | 8.1 |

-continued

| Examples | R1 | R2 | R3 | R4 | [M + H]⁺ | rt (min) |
|---|---|---|---|---|---|---|
| 500 | (isobutyl with X₁) | (isobutyl with X₂) | 3,4,5-trimethoxyphenyl-X₃ | X₄-(CH₂)₃-NH-CH₂-(2,4-dimethoxyphenyl) | 662.4 | 8.2 |
| 501 | (isobutyl with X₁) | (isobutyl with X₂) | 3,4,5-trimethoxyphenyl-X₃ | X₄-(CH₂)₃-NH-CH(CH₃)-CH₂-phenyl | 644.4 | 8.4 |
| 502 | (isobutyl with X₁) | (isobutyl with X₂) | 3,4,5-trimethoxyphenyl-X₃ | X₄-(CH₂)₃-NH-CH₂-C(CH₃)₂-CH₂-CH=CH₂ | 608.4 | 8.2 |

| Examples | R1 | R2 | R3 | R4 | [M+H]+ | rt (min) |
|---|---|---|---|---|---|---|
| 503 | (isobutyl-X1) | (isobutyl-X2) | 3,4,5-trimethoxyphenyl-X3 | X4-(CH2)3-NH-CH2-(4-methylphenyl) | 616.4 | 8.2 |
| 504 | (isobutyl-X1) | (isobutyl-X2) | 3,4,5-trimethoxyphenyl-X3 | X4-(CH2)3-NH-CH2-(3,4-dimethylphenyl) | 630.4 | 8.3 |
| 505 | (isobutyl-X1) | (isobutyl-X2) | 3,4,5-trimethoxyphenyl-X3 | X4-CH(CH3)-NH-CH(CH3)2 | 554.4 | 7.8 |

-continued

| Examples | R1 | R2 | R3 | R4 | [M+H]⁺ | rt (min) |
|---|---|---|---|---|---|---|
| 506 | | | | | 672.4 | 8.6 |
| 507 | | | | | 584.4 | 7.9 |
| 508 | | | | | 568.3 | 7.9 |
| 509 | | | | | 596.4 | 8.1 |

| Examples | R1 | R2 | R3 | R4 | [M + H]+ | rt (min) |
|---|---|---|---|---|---|---|
| 510 | (isobutyl-X₁) | (isobutyl-X₂) | (3,4,5-trimethoxyphenyl-X₃) | X₄-(CH₂)₄-NH-CH(CH₂OH)-C(CH₃)₂- | 612.4 | 8.0 |
| 511 | (isobutyl-X₁) | (isobutyl-X₂) | (3,4,5-trimethoxyphenyl-X₃) | X₄-(CH₂)₄-NH-C(CH₃)₂-CH₂CH₃ | 582.4 | 8.1 |
| 512 | (isobutyl-X₁) | (isobutyl-X₂) | (3,4,5-trimethoxyphenyl-X₃) | X₄-(CH₂)₃-NH-cyclobutyl | 556.3 | 7.9 |
| 513 | (isobutyl-X₁) | (isobutyl-X₂) | (3,4,5-trimethoxyphenyl-X₃) | X₄-(CH₂)₄-NH-CH₂-C(CH₃)(CH₂OH)- | 598.3 | 7.9 |
| 514 | (isobutyl-X₁) | (isobutyl-X₂) | (3,4,5-trimethoxyphenyl-X₃) | X₄-(CH₂)₃-NH-cyclopentyl | 580.4 | 8.0 |

-continued

| Examples | R1 | R2 | R3 | R4 | [M + H]+ | rt (min) |
|---|---|---|---|---|---|---|
| 515 | H3C-CH(CH3)-CH2-X1 | H3C-CH(CH3)-CH2-X2 | 3,4,5-trimethoxyphenyl-X3 | X4-(CH2)3-NH-cyclopropyl | 552.3 | 7.9 |
| 516 | H3C-CH(CH3)-CH2-X1 | H3C-CH(CH3)-CH2-X2 | 3,4,5-trimethoxyphenyl-X3 | X4-(CH2)3-NH-C(CH3)(CH3)-CH2OH | 612.4 | 8.0 |
| 517 | H3C-CH(CH3)-CH2-X1 | H3C-CH(CH3)-CH2-X2 | 3,4,5-trimethoxyphenyl-X3 | X4-(CH2)3-NH-C(CH2CH3)(CH2CH3)-C≡CH | 606.4 | 8.2 |
| 518 | H3C-CH(CH3)-CH2-X1 | H3C-CH(CH3)-CH2-X2 | 3,4,5-trimethoxyphenyl-X3 | X4-(CH2)3-NH-C(CH3)2-C(CH3)3 | 624.4 | 8.4 |

-continued

| Examples | R1 | R2 | R3 | R4 | [M + H]+ | rt (min) |
|---|---|---|---|---|---|---|
| 519 | H3C-CH(CH3)-CH2-X1 | X2-CH2-CH(CH3)-CH3 | 3,4,5-trimethoxyphenyl-X3 | X4-(CH2)3-NH-C(CH3)2-CH2OH (with CH3) | 612.4 | 8.0 |
| 520 | H3C-CH(CH3)-CH2-X1 | X2-CH2-CH(CH3)-CH3 | 3,4,5-trimethoxyphenyl-X3 | X4-(CH2)3-NH-adamantyl | 646.4 | 8.3 |
| 521 | H3C-CH(CH3)-CH2-X1 | X2-CH2-CH(CH3)-CH3 | 3,4,5-trimethoxyphenyl-X3 | X4-(CH2)3-NH-cycloheptyl | 608.4 | 8.2 |

| Examples | R1 | R2 | R3 | R4 | [M+H]⁺ | rt (min) |
|---|---|---|---|---|---|---|
| 522 | | | | | 616.3 | 8.2 |
| 523 | | | | | 630.3 | 8.2 |
| 524 | | | | | 636.4 | 8.5 |
| 525 | | | | | 608.3 | 8.2 |

| Examples | R1 | R2 | R3 | R4 | [M + H]+ | rt (min) |
|---|---|---|---|---|---|---|
| 526 | | | | | 582.3 | 8.1 |
| 527 | | | | | 600.3 | 7.8 |
| 528 | | | | | 610.3 | 8.2 |

-continued

| Examples | R1 | R2 | R3 | R4 | [M + H]⁺ | rt (min) |
|---|---|---|---|---|---|---|
| 529 | H₃C-CH(CH₃)-CH₂-X₁ | H₃C-CH(CH₃)-CH₂-X₂ | 3,4,5-trimethoxyphenyl-X₃ | X₄-(CH₂)₃-NH-CH(CH₃)-CH(CH₃)-CH₃ | 582.3 | 8.1 |
| 530 | H₃C-CH(CH₃)-CH₂-X₁ | H₃C-CH(CH₃)-CH₂-X₂ | 3,4,5-trimethoxyphenyl-X₃ | X₄-(CH₂)₃-NH-CH(CH(CH₃))-CH₂OH | 598.3 | 7.9 |
| 531 | H₃C-CH(CH₃)-CH₂-X₁ | H₃C-CH(CH₃)-CH₂-X₂ | 3,4,5-trimethoxyphenyl-X₃ | X₄-(CH₂)₃-NH-CH(CH₃)-CH₂-O-CH₃ | 584.3 | 7.9 |

-continued

| Examples | R1 | R2 | R3 | R4 | [M + H]⁺ | rt (min) |
|---|---|---|---|---|---|---|
| 532 | H₃C-CH(CH₃)-CH₂-X₁ | X₂-CH₂-CH(CH₃)-CH₃ (H₃C on left) | 3,4,5-trimethoxyphenyl-X₃ | X₄-(CH₂)₃-NH-CH(CH₃)-CH₂OH | 570.2 | 7.8 |
| 533 | H₃C-CH(CH₃)-CH₂-X₁ | X₂-CH₂-CH(CH₃)-CH₃ | 3,4,5-trimethoxyphenyl-X₃ | X₄-(CH₂)₃-NH-CH(CH₃)-CH₂-CH(CH₃)-CH₃ | 596.4 | 8.2 |
| 534 | H₃C-CH(CH₃)-CH₂-X₁ | X₂-CH₂-CH(CH₃)-CH₃ | 3,4,5-trimethoxyphenyl-X₃ | X₄-(CH₂)₃-NH-C(cyclopentyl)(CH₂OH) | 610.3 | 7.9 |

| Examples | R1 | R2 | R3 | R4 | [M + H]+ | rt (min) |
|---|---|---|---|---|---|---|
| 535 | H3C-CH(CH3)-CH2-X1 | H3C-CH(CH3)-CH2-X2 | 2-Cl-4,5-dimethoxyphenyl (X3) | X4-(CH2)3-NH-CH2-C(CH3)3 | 586.3 | 8.4 |
| 536 | H3C-CH(CH3)-CH2-X1 | H3C-CH(CH3)-CH2-X2 | 3-acetylphenyl (X3) | X4-(CH2)3-NH-CH2-C(CH3)3 | 534.3 | 7.6 |
| 537 | H3C-CH(CH3)-CH2-X1 | H3C-CH(CH3)-CH2-X2 | 3-chloro-4-methylphenyl (X3) | X4-(CH2)3-NH-CH2-C(CH3)3 | 540.3 | 7.9 |
| 538 | H3C-CH(CH3)-CH2-X1 | H3C-CH(CH3)-CH2-X2 | 4-chloro-3,5-dimethoxyphenyl (X3) | X4-(CH2)3-NH-CH2-C(CH3)3 | 586.3 | 8.4 |

Pharmacological Study

The antagonist activity of the GnRH of the compounds according to the invention is measured according to the following protocols:

Establishment of a Stable Line Transfected by the Human LHRH Receptor:

The cDNA of the human LHRH receptor is cloned in the EcoRI site in a mammalian expression vector pCDNA3.1 (InVitrogen Inc.). This plasmid construction is transfected using Effectene according to the manufacturers recommendations (Qiagen) in a cell line derived from human embryo kidney, HEK-293 (ATCC) and the selection is carried out in a DMEM medium containing 0.5 mg/ml of geneticin. The cells containing the expression vector for the LHRH receptor are then cloned by limited dilution then multiplied in culture. These cell clones are then tested for the expression of the human LHRH receptor by competitive inhibition tests of the bond and measurement of inositol phosphates.

Cell Culture and Membrane Preparation:

The HEK-293 cells expressing in a stable manner the human LHRH receptor as described above are cultured in a DMEM medium in the presence of 10% foetal calf serum and supplemented by 0.4 mg/ml geneticin (G418, Sigma Chemical Company). The cells are detached from the culture medium with EDTA 0.5 mM and centrifuged at 500 g for 10 minutes at 4° C. The cell pellet is washed with Tris 50 mM, pH 7.4 and centrifuged twice at 500 g for 10 minutes. The cells are finally lysed by sonication then centrifuged at 39000 g for 10 minutes at 4° C. The pellet is resuspended in Tris 50 mM, pH 7.4 and centrifuged at 50000 g for 10 minutes at 4° C. in order to obtain a membrane pellet divided into several aliquots stored at −80° C. before use.

Study of the Affinity for the Human LHRH Receptor:

The affinity of a compound of the invention for the human LHRH receptor is determined by measurement of the inhibition of the bond of [$^{125}$I-Tyr5]-DTrp$^6$-LHRH on human cells transfected by the cDNA of the human LHRH receptor.

The competitive inhibition tests of the bond of [$^{125}$I-Tyr5]-DTrp$^6$-LHRH are carried out in duplicate in polypropylene 96 well plates. The membranes of the HEK-293 cells expressing in a stable manner the human LHRH receptor (20 μg proteins/well) are incubated in the presence of [$^{125}$I-Tyr5]-DTrp$^6$-LHRH (0.2 nM) for 60 minutes at 4° C. in a medium containing Tris/HCl 50 mM pH 7.4, Bacitracin 0.1 mg/ml, BSA 0.1% (1 mg/ml).

The bound [$^{125}$I-Tyr5]-DTrp$^6$-LHRH is separated from the free [$^{125}$I-Tyr5]-DTrp$^6$-LHRH by filtration through filter plates constituted by glass fibre GF/C (Unifilter, Packard) impregnated with polyethylenimine 0.1%, using a FilterMate 96 (Packard). The filters are then washed with Tris/HCl 50 mM buffer at 4° C. for 4 seconds and the radioactivity is counted using a scintillation counter (Packard, Topcount).

The specific bond is calculated after subtracting the non-specific bond (determined in the presence of DTrp$^6$-LHRH 0.1 μM) from the total bond. The data relative to the bond obtained by nonlinear regression analysis and the inhibition constant values (Ki) are determined.

Determination of the agonist or antagonist profile of a compound of the present invention is carried out by the method described below.

Functional Test: Inhibition of the Production of Intracellular Inositol Phosphates HEK-293 cells expressing in a stable manner the human GnRH receptor are cultured at a rate of 200,000 cells per well in a 24-well plate coated with poly-D-lysine (Falcon Biocoat) in a DMEM medium in the presence of 10% foetal calf serum and 0.4 mg/ml geneticin for 24 hours.

The medium is then replaced by DMEM not containing Inositol in the presence of 10% foetal calf serum and 1 μCi/ml of [3H]myo-inositol (Amersham) for 16-18 hours at 37° C.

The cells are washed with DMEM not containing inositol in the presence of 10 mM lithium chloride and incubated for 30 minutes at 37° C.

The production of inositol phosphates is stimulated by the addition of DTrp$^6$-LHRH 0.5 nM over 45 minutes at 37° C.

The antagonist effect of a compound is measured by the simultaneous addition of 6 DTrp$^6$-LHRH 0.5 nM and the compounds to be tested at different increasing concentrations (example: $10^{-10}$ M to $10^{-5}$M).

The reaction medium is eliminated and 1 ml of 0.1 M formic acid is added and incubated for 5 minutes at 4° C.

The plate is then frozen at −80° C. then thawed at ambient temperature.

The inositol phosphates are then separated from all of the intracellular inositols on ion exchange resin (Biorad) by eluting with 1M ammonium formate and 0.1M formic acid.

The quantity of inositol phosphates leaving the column is finally measured in the presence of scintillating liquid.

Results:

The tests carried out according to the protocols described above have allowed it to be shown that the products of general formula (I) defined in the present Application have a good affinity for the LHRH receptor, the inhibition constant K$_i$ on this receptor being below micromolar for certain of the exemplified compounds.

The invention claimed is:

1. A compound of the formula

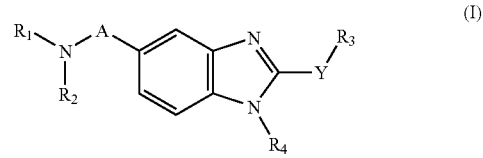

(I)

in racemic, enantiomeric form or any combination of these forms wherein:

A is —CH$_2$— or —C(O)—;

Y is —S— or —NH—;

R$_1$ and R$_2$ are independently selected from the group consisting of hydrogen, (C$_1$-C$_8$)alkyl, (C$_5$-C$_9$)bicycloalkyl optionally substituted by at least one (C$_1$-C$_6$)alkyl, and —(CH$_2$)$_n$—X, X is selected from the group consisting of amino, (C$_1$-C$_6$)alkylamino, di((C$_1$-C$_6$)alkyl)amino, (C$_3$-C$_7$)cycloalkyl, adamantyl, heterocycloalkyl, aryl, aryl-carbonyl, heteroaryl,

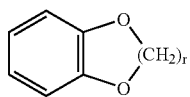 and 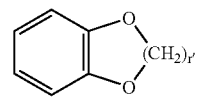

r = 1, 2          r' = 1, 2 the (C$_3$-C$_7$)cycloalkyl, heterocycloalkyl aryl and heteroaryl being optionally substituted by at least one member selected from the group consisting of —(CH$_2$)$_{n'}$—X'—Y', halo, oxo, nitro, cyano, amino, (C$_1$-C$_6$)alkylamino, di((C$_1$-C$_8$)alkyl)amino, hydroxy and N$_3$;

X' is selected from the group consisting of —O—, —S—, —C(O)—, —C(O)—O—, —NH—C(O)—, —NH—SO$_2$— and a covalent bond;

Y' is selected from the group consisting of (C$_1$-C$_6$)alkyl optionally substituted by at least one halo; heteroaryl, aryl and heterocycloalkyl optionally substituted by at least one member selected from the group consisting of (C$_1$-C$_6$)alkyl, (C$_1$-C$_6$)alkoxy, halo, nitro, cyano, amino, CF$_3$, OCF$_3$, hydroxy, N$_3$, (C$_1$-C$_6$)alkylamino and di((C$_1$-C$_8$)alkyl)amino;

n is an integer from 0 to 6 and n' is an integer from 0 to 2;

or R$_1$ and R$_2$ form together with the nitrogen atom to which they are attached, a member selected from the group consisting of heterocycloalkyl, heterobicycloalkyl,

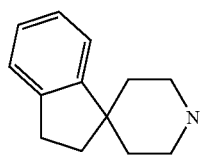
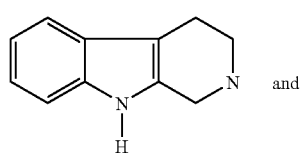
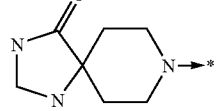
and the member which R$_1$ and R$_2$ together form is optionally substituted by at least one member selected from the group consisting of —(CH$_2$)$_{n''}$—X"—Y", oxo, hydroxy, halo, nitro and cyano;

X" is selected from the group consisting of —O—, —C(O)—, —C(O)—O— and a covalent bond;

Y" is selected from the group consisting of (C$_1$-C$_6$)alkyl, amino, (C$_1$-C$_6$)alkylamino, di((C$_1$-C$_6$)alkyl)amino, (C$_3$-C$_7$)cycloalkyl, heterocycloalkyl, arylalkyl, aryl and heteroaryl optionally substituted by at least one member selected from the group consisting of (C$_1$-C$_6$)alkyl, (C$_1$-C$_6$)alkoxy, (C$_1$-C$_6$)alkyl-carbonyl, halo, hydroxy, nitro, cyano, CF$_3$, OCF$_3$, amino, (C$_1$-C$_6$)alkylamino, di((C$_1$-C$_6$)alkyl)amino),

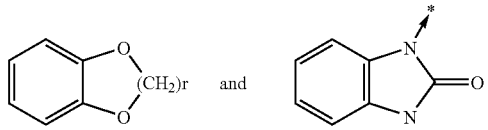

n" is an integer from 0 to 4;

R$_3$ is —(CH$_2$)$_p$—W$_3$—(CH$_2$)$_{p'}$-Z$_3$

W$_3$ is selected from the group consisting of a covalent bond, —CH(OH)— and —C(O)—;

Z$_3$ is selected from the group consisting of (C$_1$-C$_6$)alkyl, adamantly, aryl, a heteroaryl,

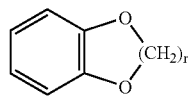
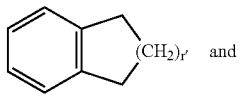
and r = 1, 2  r' = 1.2

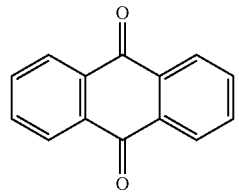

the aryl being optionally substituted by at least one member selected from the group consisting of —(CH$_2$)$_{p''}$—V$_3$—Y$_3$, halo, nitro, cyano, N$_3$, and hydroxy;

V$_3$ is selected from the group consisting of —O—, —S—, —C(O)—, —C(O)—O—, —SO$_2$— and a covalent bond;

Y$_3$ is selected from the group consisting of (C$_1$-C$_6$)alkyl optionally substituted by at least one member selected from the group consisting of halo, amino, (C$_1$-C$_6$)alkylamino, di((C$_1$-C$_6$)alkyl)amino, phenylcarbonylmethyl, heterocycloalkyl and aryl;

p, p' and p" represent are, independently, an integer from 0 to 4;

R$_4$ is —(CH$_2$)$_s$—R"$_4$

R"$_4$ is selected from the group consisting of heterocycloalkyl containing at least one nitrogen atom and optionally substituted by (C$_1$-C$_6$)alkyl or aralkyl; a heteroaryl containing at least one nitrogen atom and optionally substituted by (C$_1$-C$_6$)alkyl; and —NW$_4$W'$_4$ W$_4$ is selected from the group consisting of hydrogen, (C$_1$-C$_8$)alkyl and (C$_3$-C$_7$)cycloalkyl;

W'$_4$ is —(CH$_2$)$_s$-Q$_4$-Z$_4$;

Q$_4$ is selected from the group consisting of a covalent bond, —CH$_2$—CH(OH)—[CH$_2$]$_t$—[O]$_{t'}$—[CH$_2$]$_{t''}$ and —C(O)—O—;

t, t' and t" are, independently, 0 or 1;

Z$_4$ is selected from the group consisting of hydrogen, (C$_1$-C$_8$)alkyl optionally substituted by at least one member selected from the group consisting of (C$_1$-C$_6$)alkoxy, (C$_1$-C$_6$)alkylthio, (C$_1$-C$_6$)alkyldithio, hydroxy; (C$_2$-C$_6$)alkenyl; (C$_2$-C$_6$)alkynyl; (C$_3$-C$_7$)cycloalkyl optionally substituted by at least one member selected from the group consisting of (C$_1$-C$_6$)alkyl, (C$_1$-C$_6$)alkoxy-carbonyl and (C$_1$-C$_6$)hydroxyalkyl; cyclohexene, adamantyl; heteroaryl and aryl optionally substituted by at least one member selected from the group consisting of —(CH$_2$)$_{q''}$—V$_4$—Y$_4$, hydroxy, halo, nitro and cyano;

V$_4$ is selected from the group consisting of —O—, —S—, —NH—C(O)— and a covalent bond;

Y$_4$ is selected from the group consisting of (C$_1$-C$_6$)alkyl optionally substituted by di((C$_1$-C$_6$)alkyl)amino or at least one halo; amino; (C$_1$-C$_6$)alkylamino; di((C$_1$-C$_6$)alkyl)amino; aralkyl and heterocycloalkyl;

q" represents is an integer from 0 to 4;
or $Z_4$ is

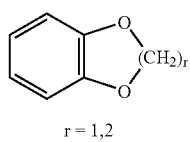

r = 1,2 s and s' are, independently, an integer from 0 to 6; and a pharmaceutically acceptable salt thereof.

2. A compound of claim 1, wherein A is —C(O)—; or a pharmaceutically acceptable salt thereof.

3. A compound of claim 1 wherein cycloalkyl represented by X is cyclohexyl or cycloheptyl,
the heterocycloalkyl represented by X is selected from the group consisting of piperidine, morpholine, pyrrolidine, thiazolidine and tetrahydrothiophene;
the aryl represented by X is selected from the group consisting of phenyl, naphthyl and fluorenyl;
the aryl of the aryl-carbonyl represented by X, is phenyl;
the heteroaryl represented by X is selected from the group consisting of pyridine, imidazole, thiophene, indole, carbazole and isoquinoline;
the heteroaryl represented by Y' is oxazole or imidazole;
the aryl represented by Y' is phenyl;
the heterocycloalkyl represented by Y' is piperazine;
the heterocycloalkyl which $R_1$ and $R_2$ form together with the nitrogen atom to which they are attached, is selected from the group consisting of piperidine, piperazine, diazepane, thiazolidine and morpholine;
the cycloalkyl represented by Y" is cyclopentyl or cyclohexyl;
the heterocycloalkyl represented by Y" is selected from the group consisting of piperidine, pyrrolidine and morpholine;
the arylalkyl and the aryl represented by Y" are respectively benzyl and phenyl;
the heteroaryl represented by Y" is selected from the group consisting of pyridine, pyrazine, furan and thiophene; or a pharmaceutically acceptable salt thereof.

4. A compound of claim 1 wherein
the aryl represented by $Z_3$ is the phenyl or naphthyl;
the heteroaryl represented by $Z_3$ is benzo[b]thiophene or benzo[b]furan;
the heteroaryl represented by $Z_3$ is benzo[b]thiophene or benzo[b]furan;
the heterocycloalkyl and the aryl represented by $Y_3$ are respectively pyrrolidine and phenyl or a pharmaceutically acceptable salt thereof.

5. A compound of claim 1 wherein
the heterocycloalkyl represented by $R''_4$ is selected from the group consisting of piperazine, piperidine, morpholine and pyrrolidine;
the aralkyl which optionally substitutes the heterocycloalkyl represented by $R''_4$ is benzyl;
the heteroaryl represented by $R''_4$ is imidazole;
the ($C_3$-$C_7$)cycloalkyl represented by $Z_4$ is selected from the group consisting of cyclopropyl, cyclobutyl, cyclopentyl, cyclohexyl and cycloheptyl;
the heteroaryl represented by $Z_4$ is selected from the group consisting of pyridine, thiophene, indole and furan;
the aryl represented by $Z_4$ is phenyl or naphthyl;
the aralkyl represented by $Y_4$ is benzyl;
the heterocycloalkyl represented by $Y_4$ is pyrrolidine;
the aralkyl which is substituted on the heterocycloalkyl formed together by $W_4$ and $W'_4$ is benzyl; or a pharmaceutically acceptable salt thereof.

6. A compound of claim 1 wherein A is —C(O)— and $R_1$ and $R_2$ are independently selected from the group consisting of hydrogen, (($C_1$-$C_8$)alkyl and —(CH$_2$)$_n$—X in which
X is selected from the group consisting of amino, di(alkyl)amino, adamentyl, cyclohexyl, cycloheptyl, piperidine, morpholine, pyrrolidine, phenyl, pyridine, imidazole, thiophene, indole, carbazole being optionally substituted by ($C_1$-$C_6$)alkyl,

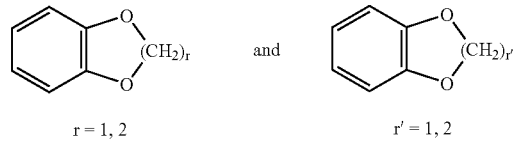

r = 1, 2          r' = 1, 2 the piperidine, pyrrolidine and phenyl being optionally substituted by at least one member selected from the group consisting of —(CH$_2$)$_{n'}$—X'—Y', halo, oxo, amino and di((Ci —$C_8$)alkyl)amino;
X' is selected from the group consisting of —O—, —S—, —C(O)—O—, —NH—C(O)—, —NH—SO$_2$— and a covalent bond;
Y' is selected from the group consisting of ($C_1$-$C_6$)alkyl, oxazole, phenyl optionally substituted by ($C_1$-$C_4$)alkyl or piperazine optionally substituted by ($C_1$-$C_4$)alkyl;
or $R_1$ and $R_2$ form together with the nitrogen atom to which they are attached, a member selected from the group consisting of piperidine, piperazine, diazepane, thiazolidine, morpholine,

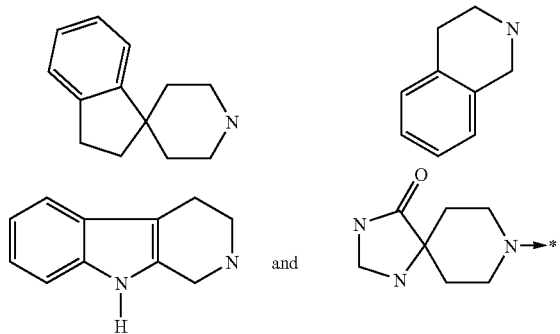

the member formed by $R_1$ and $R_2$ together being optionally substituted by at least one —(CH$_2$)$_{n''}$—X"—Y";

X" is selected from the group consisting of —C(O)—, —C(O)—O— or a covalent bond;
Y" is selected from the group consisting of ($C_1$-$C_6$)alkyl; di(alkyl)amino, cyclopentyl, cyclohexyl, piperidine, pyrrolidine, morpholine, benzyl, pyridine, pyrazine, furan, thiophene, and phenyl optionally substituted by at least one member selected from the group consisting of ($C_1$-$C_6$)alkyl, ($C_1$-$C_6$)alkoxy, ($C_1$-$C_6$)alkyl-carbonyl and halo; or Y"

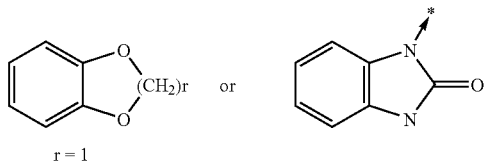

r = 1 or a pharmaceutically acceptable salt thereof.

7. A compound of claim 1 wherein A is —C(O)— and $R_3$ is —$(CH_2)_p$—$W_3$—$(CH_2)_{p'}$-$Z_3$
$W_3$ is selected from the group consisting of a covalent bond, —CH(OH)— and —C(O)—;
$Z_3$ is selected from the group consisting of $(C_1-C_6)$alkyl, phenyl, naphthyl, benzo[b]thiophene, benzo[b]furannyl,

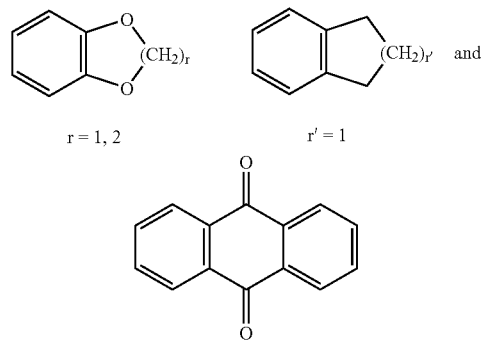

r = 1, 2        r' = 1 the phenyl radical being optionally substituted by at least one member selected from the group consisting of —$(CH_2)_{p''}$—$V_3$—$Y_3$, halo, nitro, cyano;
$V_3$ is —O—, —S—, —C(O)—, —C(O)—O—, —$SO_2$— and a covalent bond;
$Y_3$ is selected from the group consisting of $(C_1-C_6)$alkyl radical optionally substituted by at least one halo; amino; di(($C_1-C_6$)alkyl)amino; phenylcarbonylmethyl; pyrrolidine and phenyl;
p, p' and p" are independently, an integer from 0 to 2; or a pharmaceutically acceptable salt thereof.

8. A compound of A compound of claim 1 wherein A is —C(O)— and $R_4$ is —$(CH_2)_s$—$R''_4$
$R''_4$ is selected from the group consisting of piperidine ring optionally substituted by benzyl, piperazine optionally substituted by benzyl and —$NW_4W'_4$
$W_4$ is hydrogen or $(C_1-C_8)$alkyl;
$W'_4$ is —$(CH_2)_{s'}$-$Q_4$-$Z_4$;
$Q_4$ is selected from the group consisting of a covalent bond, —$CH_2$—CH(OH)—, —$CH_2$—CH(OH)—$CH_2$—O—, —$CH_2$—CH(OH)—$CH_2$—, —$CH_2$—CH(OH)—$CH_2$—O—; $CH_2$ and —C(O)—O—;
$Z_4$ is selected from the group consisting of hydrogen, $(C_1-C_8)$alkyl optionally substituted by $(C_1-C_6)$alkoxy, $(C_1-C_6)$alkylthio, $(C_1-C_6)$alkyldithio, one or two hydroxy; $(C_2-C_6)$alkenyl; $(C_2-C_6)$alkynyl; cyclopropyl optionally substituted by alkoxycarbonyl; cyclobutyl, cyclopentyl optionally substituted by hydroxyalkyl; cyclohexyl optionally substituted by at least one alkyl; cycloheptyl, cyclohexene, adamantyl, pyridine, thiophene, indole, furane, naphthyl; phenyl optionally substituted by at least one member selected from the group consisting of —$(CH_2)_{q''}$—$X_4$—$Y_4$, hydroxy, halo and cyano;
$X_4$ is —O— or a covalent bond;
$Y_4$ is selected from the group consisting of $(C_1-C_6)$alkyl, di(($C_1-C_6$)alkyl)amino and pyrrolidine or a pharmaceutically acceptable salt thereof.

9. A compound of claim 1 wherein A is —C(O)—, Y is —NH— and
$R_1$ and $R_2$ are independently $(C_1-C_8)$alkyl;
$R_3$ is —$(CH_2)_p$—$W_3$—$(CH_2)_{p'}$-$Z_3$
$W_3$ is a covalent bond; $Z_3$ is phenyl substituted by at least one member selected from the group consisting of —$(CH_2)_{p''}$—$V_3$—$Y_3$ and halo;
$V_3$ is —O— or —S—; and $Y_3$ is $(C_1-C_6)$alkyl; p, p' and p" are 0;
$R_4$ is —$(CH_2)_s$—$R''_4$
$R''_4$ is —$NW_4W'_4$
$W_4$ is hydrogen or $(C_1-C_8)$alkyl;
$W'_4$ is —$(CH_2)_{s'}$-$Q_4$-$Z_4$;
$Q_4$ is a covalent bond;
$Z_4$ is selected from the group consisting of hydrogen, $(C_1-C_8)$alkyl, optionally substituted by hydroxy, $(C_3-C_7)$cycloalkyl, heteroaryl, aryl optionally substituted by at least one —$(CH_2)_{q''}$—$V_4$—$Y_4$;
$V_4$ is —O— or a covalent bond;
$Y_4$ is $(C_1-C_6)$alkyl or di(($C_1-C_6$)alkyl)amino;
q" represents is 0; s is an integer from 2 to 4, and s' is an integer from 1 to 2;
or a pharmaceutically acceptable salt thereof.

10. A compound of claim 9, wherein $(C_3-C_7)$cycloalkyl is cyclopentyl or cyclohexyl, the heteroaryl is pyridine and the aryl is phenyl; or a pharmaceutically acceptable salt thereof.

11. A compound of claim 1 wherein A is —C(O)—, Y is sulfur,
$R_1$ and $R_2$ are independently $(C_1-C_8)$alkyl;
$R_3$ is —$(CH_2)_p$—$W_3$—$(CH_2)_{p'}$-$Z_3$
$W_3$ is a covalent bond or —C(O)—; $Z_3$ is phenyl substituted by at least one of —$(CH_2)_{p''}$—$V_3Y_3$ or halo; $V_3$ is —O— or a covalent bond; and $Y_3$ is $(C_1-C_6)$alkyl or di(($C_1-C_6$)alkyl)amino; p is 1, and p' and p" are 0;
$R_4$ is —$(CH_2)_s$—$R''_4$
$R''_4$ is —$NW_4W'_4$
$W_4$ is hydrogen or $(C_1-C_8)$alkyl;
$W'_4$ is —$(CH_2)_{s'}$-$Q_4$-$Z_4$;
$Q_4$ is a covalent bond;
$Z_4$ is selected from the group consisting of hydrogen, $(C_1-C_8)$alkyl, heteroaryl and aryl
s is an integer from 2 to 4, and s' is an integer from 1 to 2, or a pharmaceutically acceptable salt thereof.

12. A compound of claim 11, wherein heteroaryl is pyridine and aryl is phenyl; or a pharmaceutically acceptable salt thereof.

13. A compound of claim 1, wherein A is selected from the group consisting of —$CH_2$—, or Y—NH— and $R_1$ and $R_2$ are independently (($C_1-C_6$)alkyl; $R_3$ is phenyl substituted by at least one $(C_1-C_6)$alkoxy; $R_4$ is —$(CH_2)_s$—$R''_4$; $R''_4$— $NW_4W'_4$; $W_4$ is $(C_1-C_8)$alkyl; $W'_4$—$(CH_2)_{s'}$-$Q_4$-$Z_4$; $Q_4$ is a covalent bond and $Z_4$ is pyridine; or a pharmaceutically acceptable salt thereof.

14. A composition with antagonist activity to Gonadotropin-Releasing hormone comprising an antagonistically effective amount of a compound of claim 1 and a pharmaceutically acceptable carrier.

15. A method of treating women during medically-assisted procreation protocols for endometriosis, fibroma, polycystic ovary syndrome, breast cancer, ovary cancer, endometrium cancer and gonadotropic hypophyseal desensitization comprising administering to women in need thereof an amount of a compound of claim 1 sufficient to treat said condition.

16. A method of treating men for benign prostatic hyperplasia and prostate cancer comprising administering to men in need thereof an amount of a compound of claim 1 sufficient to treat said conditions.

17. A method of treating a youngster for precocious male or female puberty comprising administering to a youngster in need thereof an amount of a compound of claim 13 sufficient to treat said condition.

* * * * *

UNITED STATES PATENT AND TRADEMARK OFFICE
CERTIFICATE OF CORRECTION

| | | |
|---|---|---|
| PATENT NO. | : 7,495,110 B2 | |
| APPLICATION NO. | : 10/499384 | |
| DATED | : February 24, 2009 | |
| INVENTOR(S) | : Lydie Poitout et al. | |

It is certified that error appears in the above-identified patent and that said Letters Patent is hereby corrected as shown below:

Column 350, line 46, delete the text "—CH2— or";

Column 350, line 47, delete "or —NH—";

Column 354, line 4, delete "A is — C(O) — and";

Column 355, line 13, delete "A is — C(O) — and";

Column 355, lines 50-51, delete "A is — C(O) — and";

Column 356, lines 9-10, delete "A is — C(O) —,Y is —NH— and";

Column 356, lines 36-37, delete "A is —C(O) —, Y is sulfur";

Column 356, lines 57-58, delete "A is selected from the group consisting of —CH2—, or Y—NH— and";

Column 353, line 13, cancel the text beginning with "2. A compound of claim 1" and ending "salt thereof.";

Column 357, line 1, cancel the text beginning with "15. A method of treating" and ending "to treat said condition." in column 358, line 6.

Signed and Sealed this
Thirty-first Day of May, 2011

David J. Kappos
*Director of the United States Patent and Trademark Office*